US010735298B2

United States Patent
Chen et al.

(10) Patent No.: US 10,735,298 B2
(45) Date of Patent: Aug. 4, 2020

(54) METHOD, APPARATUS, SERVER AND SYSTEM FOR VITAL SIGN DETECTION AND MONITORING

(71) Applicant: ORIGIN WIRELESS, INC., Greenbelt, MD (US)

(72) Inventors: Chen Chen, Burlingame, CA (US); Feng Zhang, Greenbelt, MD (US); Qinyi Xu, College Park, MD (US); Beibei Wang, Clarksville, MD (US); Chenshu Wu, Greenbelt, MD (US); Hangfang Zhang, Greenbelt, MD (US); Chau-Wai Wong, Raleigh, NC (US); David N. Claffey, Somerville, MA (US); Chun-I Chen, Brookeville, MD (US); Hung-Quoc Duc Lai, Parkville, MD (US); Zhung-Han Wu, College Park, MD (US); Min Wu, Clarksville, MD (US); Yi Han, Ellicott City, MD (US); Oscar Chi-Lim Au, San Jose, CA (US); K. J. Ray Liu, Potomac, MD (US)

(73) Assignee: ORIGIN WIRELESS, INC., Greenbelt, MD (US)

( * ) Notice: Subject to any disclaimer, the term of this patent is extended or adjusted under 35 U.S.C. 154(b) by 0 days.

(21) Appl. No.: 16/200,608

(22) Filed: Nov. 26, 2018

(65) Prior Publication Data
US 2019/0166030 A1    May 30, 2019

Related U.S. Application Data

(60) Continuation-in-part of application No. 15/326,112, filed as application No. PCT/US2015/041037 on Jul.
(Continued)

(51) Int. Cl.
*H04L 12/26* (2006.01)
*H04L 25/49* (2006.01)
(Continued)

(52) U.S. Cl.
CPC ............ *H04L 43/12* (2013.01); *A61B 5/0816* (2013.01); *A61B 5/113* (2013.01); *A61B 5/4806* (2013.01);
(Continued)

(58) Field of Classification Search
CPC combination set(s) only.
See application file for complete search history.

(56) References Cited

U.S. PATENT DOCUMENTS

| | | |
|---|---|---|
| 7,260,532 B2 | 8/2007 | Rees |
| 7,736,314 B2 | 6/2010 | Beach et al. |

(Continued)

FOREIGN PATENT DOCUMENTS

| | | |
|---|---|---|
| EP | 3426137 A1 | 1/2019 |
| WO | 2010/134933 A1 | 11/2010 |

(Continued)

OTHER PUBLICATIONS

Krawczyk, M. and Gerkmann, T., 2012, September. STFT phase improvement for single channel speech enhancement. In IWAENC 2012; International Workshop on Acoustic Signal Enhancement (pp. 1-4). VDE.*

(Continued)

*Primary Examiner* — Zhitong Chen
(74) *Attorney, Agent, or Firm* — Yingxin Xiao

(57) ABSTRACT

Methods, apparatus and systems for detecting and monitoring vital signs and other periodic motions of an object are disclosed. In one example, a system for monitoring object motion in a venue is disclosed. The system comprises a
(Continued)

transmitter, a receiver, and a vital sign estimator. The transmitter is located at a first position in the venue and configured for transmitting a wireless signal through a wireless multipath channel impacted by a pseudo-periodic motion of an object in the venue. The receiver is located at a second position in the venue and configured for: receiving the wireless signal through the wireless multipath channel impacted by the pseudo-periodic motion of the object in the venue, and obtaining at least one time series of channel information (TSCI) of the wireless multipath channel based on the wireless signal. The vital sign estimator is configured for: determining that at least one portion of the at least one TSCI in a current sliding time window is associated with the pseudo-periodic motion of the object in the venue, and computing a current characteristics related to the pseudo-periodic motion of the object in the current sliding time window based on at least one of: the at least one portion of the at least one TSCI in the current sliding time window, at least one portion of the at least one TSCI in a past sliding time window, and a past characteristics related to the pseudo-periodic motion of the object in the past sliding time window.

30 Claims, 33 Drawing Sheets

Related U.S. Application Data

17, 2015, and a continuation-in-part of application No. 14/605,611, filed on Jan. 26, 2015, now Pat. No. 10,168,414, application No. 16/200,608, filed on Nov. 26, 2018, which is a continuation-in-part of application No. 15/584,052, filed on May 2, 2017, now Pat. No. 10,447,094, application No. 16/200,608, filed on Nov. 26, 2018, which is a continuation-in-part of application No. 15/434,813, filed on Feb. 16, 2017, now Pat. No. 10,129,862, application No. 16/200,608, filed on Nov. 26, 2018, which is a continuation-in-part of application No. PCT/US2017/021963, filed on Mar. 10, 2017, application No. 16/200,608, filed on Nov. 26, 2018, which is a continuation-in-part of application No. PCT/US2017/021957, filed on Mar. 10, 2017, application No. 16/200,608, filed on Nov. 26, 2018, which is a continuation-in-part of application No. PCT/US2017/027131, filed on Apr. 12, 2017, application No. 16/200,608, filed on Nov. 26, 2018, which is a continuation-in-part of application No. 15/384,217, filed on Dec. 19, 2016, now Pat. No. 10,440,705, which is a continuation-in-part of application No. 13/706,342, filed on Dec. 5, 2012, now Pat. No. 9,883,511, and a continuation-in-part of application No. 13/969,271, filed on Aug. 16, 2013, now Pat. No. 9,882,675, and a continuation-in-part of application No. 13/969,320, filed on Aug. 16, 2013, now Pat. No. 9,559,874, and a continuation-in-part of application No. 15/041,677, filed on Feb. 11, 2016, now Pat. No. 9,794,156, which is a division of application No. 14/183,648, filed on Feb. 19, 2014, now Pat. No. 9,313,020, said application No. 15/384,217 is a continuation-in-part of application No. 15/200,430, filed on Jul. 1, 2016, now Pat. No. 9,736,002, which is a continuation of application No. 14/262,153, filed on Apr. 25, 2014, now Pat. No. 9,407,306, said application No. 15/384,217 is a continuation-in-part of application No. 15/200,429, filed on Jul. 1, 2016, now Pat. No. 9,781,700, which is a continuation of application No. 14/943,648, filed on Nov. 17, 2015, now Pat. No. 9,402,245, which is a continuation of application No. 14/202,651, filed on Mar. 10, 2014, now Pat. No. 9,226,304, said application No. 15/384,217 is a continuation-in-part of application No. 14/605,611, filed on Nov. 26, 2015, now Pat. No. 10,168,414, said application No. 15/384,217 is a continuation-in-part of application No. 14/615,984, filed on Feb. 6, 2015, now Pat. No. 9,686,054, said application No. 15/384,217 is a continuation-in-part of application No. 15/004,314, filed on Jan. 22, 2016, now Pat. No. 10,014,982, said application No. 15/384,217 is a continuation-in-part of application No. 15/061,059, filed on Mar. 4, 2016, now Pat. No. 10,609,711, said application No. 15/384,217 is a continuation-in-part of application No. PCT/US2015/041037, filed on Jul. 17, 2015, and a continuation-in-part of application No. 14/605,611, filed on Jan. 26, 2015, now Pat. No. 10,168,414, said application No. 15/384,217 is a continuation-in-part of application No. 15/268,477, filed on Sep. 16, 2016, now Pat. No. 9,887,864, and a continuation-in-part of application No. 15/200,429, filed on Jul. 1, 2016, now Pat. No. 9,781,700, said application No. 15/200,429 is a continuation of application No. 14/943,648, filed on Nov. 17, 2015, now Pat. No. 9,402,245, which is a continuation of application No. 14/202,651, filed on Mar. 10, 2014, now Pat. No. 9,226,304, said application No. 15/384,217 is a continuation-in-part of application No. 15/284,496, filed on Oct. 3, 2016, now Pat. No. 10,327,213, said application No. 15/384,217 is a continuation-in-part of application No. PCT/US2016/066015, filed on Dec. 9, 2016, application No. 16/200,608, filed on Nov. 26, 2018, which is a continuation-in-part of application No. PCT/US2017/015909, filed on Jan. 31, 2017, and a continuation-in-part of application No. PCT/US2016/066015, filed on Dec. 9, 2016, application No. 16/200,608, filed on Nov. 26, 2018, which is a continuation-in-part of application No. 15/861,422, filed on Jan. 3, 2018, and a continuation-in-part of application No. 15/873,806, filed on Jan. 17, 2018, now Pat. No. 10,270,642, and a continuation-in-part of application No. 16/101,444, filed on Aug. 11, 2018, now Pat. No. 10,291,461.

(60) Provisional application No. 62/148,019, filed on Apr. 15, 2015, provisional application No. 62/069,090, filed on Oct. 27, 2014, provisional application No. 62/025,795, filed on Jul. 17, 2014, provisional application No. 62/331,278, filed on May 3, 2016, provisional application No. 62/295,970, filed on Feb. 16, 2016, provisional application No. 62/320,965, filed on Apr. 11, 2016, provisional application No. 62/307,081, filed on Mar. 11, 2016, provisional application No. 62/316,850, filed on Apr. 1, 2016, provisional application No. 62/307,172, filed on Mar. 11, 2016, provisional application No. 62/334,110, filed on May 10, 2016, provisional application No. 62/322,575, filed on Apr. 14, 2016, provisional application No. 62/409,796, filed on Oct. 18, 2016, provisional application No. 62/557,117, filed on Sep. 11, 2017, provisional application No. 62/593,826, filed on Dec. 1, 2017, provisional application No. 62/106,395, filed on Jan. 22, 2015, provisional application No. 62/128,574, filed on Mar. 5, 2015, provisional application No. 62/219,315, filed on Sep. 16, 2015, provisional application No. 62/235,958, filed on Oct. 1, 2015, provisional application No. 62/265,155, filed on Dec. 9, 2015, provisional application No. 62/411,504, filed on Oct. 21, 2016, provisional application No. 62/383,235, filed on Sep. 2, 2016, provisional application No. 62/307,081, filed on Mar. 11, 2016, provisional application No. 62/316,850, filed on Apr. 1, 2016, provisional application No. 62/384,060, filed on Sep. 6, 2016, provisional application No. 62/678,207, filed on May 30, 2018, provisional application No. 62/734,224, filed on Sep. 20, 2018, provisional application No. 62/744,093, filed on Oct. 10, 2018, provisional application No. 62/753,017, filed on Oct. 30, 2018.

(51) Int. Cl.

| | | |
|---|---|---|
| *H04L 25/02* | (2006.01) | |
| *H04L 7/04* | (2006.01) | |
| *H04W 56/00* | (2009.01) | |
| *A61B 5/00* | (2006.01) | |
| *A61B 5/08* | (2006.01) | |
| *A61B 5/113* | (2006.01) | |

(52) U.S. Cl.
CPC .......... *H04L 7/042* (2013.01); *H04L 25/0228* (2013.01); *H04L 25/0242* (2013.01); *H04L 25/4902* (2013.01); *H04W 56/001* (2013.01)

(56) References Cited

U.S. PATENT DOCUMENTS

| | | | |
|---|---|---|---|
| 9,035,775 B2 | 5/2015 | Singh et al. | |
| 9,374,245 B2 | 6/2016 | Garrett et al. | |
| 2008/0069250 A1* | 3/2008 | Nee | H04L 25/0212 375/260 |
| 2010/0249630 A1 | 9/2010 | Droitcour et al. | |
| 2011/0309267 A1 | 12/2011 | Cui et al. | |
| 2012/0146796 A1* | 6/2012 | Margon | A61B 5/05 340/573.1 |
| 2012/0253140 A1* | 10/2012 | Addison | A61B 5/4035 600/301 |
| 2013/0331722 A1* | 12/2013 | Rodriguez-Villegas | A61B 5/0022 600/529 |
| 2014/0378809 A1* | 12/2014 | Weitnauer | A61B 5/05 600/407 |
| 2015/0038869 A1* | 2/2015 | Simon | A61B 5/7221 600/544 |
| 2016/0022145 A1 | 1/2016 | Mostov | |
| 2017/0300650 A1 | 10/2017 | Margon | |
| 2018/0183650 A1 | 6/2018 | Zhang et al. | |
| 2018/0351775 A1 | 12/2018 | Zhang et al. | |
| 2019/0007256 A1 | 1/2019 | Chen et al. | |

FOREIGN PATENT DOCUMENTS

| | | |
|---|---|---|
| WO | 2017/156492 A1 | 9/2017 |
| WO | 2017/180698 A1 | 10/2017 |

OTHER PUBLICATIONS

Fadel Adib et al., "Smart homes that monitor breathing and heart rate", in Proceedings of the 33rd Annual ACM Conference on Human Factors in Computing Systems, CHI 2015, pp. 837-846, ACM, 2015, New York, NY, USA.

Heba Abdelnasser et al., "Ubibreathe: A ubiquitous non-invasive WiFi-based breathing estimator", in Proceedings of the 16th ACM International Symposium on Mobile Ad Hoc Networking and Computing, MobiHoc '15, pp. 277-286, ACM, 2015, New York, NY, USA.

Jian Liu et al., "Tracking vital signs during sleep leveraging off-the-shelf WiFi", in Proceedings of the 16th ACM International Symposium on Mobile Ad Hoc Networking and Computing, MobiHoc '15, pp. 267-276, 2015.

Chen Chen et al., "Multi-person breathing rate estimation using time-reversal on WiFi platforms", in 2016 IEEE Global Conference on Signal and Information Processing (GlobalSIP).

Natalia V Riveral et al., "Multitarget estimation of heart and respiration rates using ultra wideband sensors", in Signal Processing Conference, 2006 14th European, Sep. 2006, pp. 1-6.

Chen Chen et al., "TR-BREATH: Time-reversal breathing rate estimation and detection", IEEE Transactions on Biomedical Engineering, Mar. 2018, pp. 489-501, vol. 65, No. 3.

Xuyu Wang et al., "Tensorbeat: Tensor decomposition for monitoring multiperson breathing beats with commodity wifi", ACM Trans. Intell. Syst. Technol., Sep. 2017, pp. 8:1-8:27, vol. 9, No. 1.

Hao Wang et al., "Human respiration detection with commodity wifi devices: Do user location and body orientation matter?", in Proceedings of the 2016 ACM International Joint Conference on Pervasive and Ubiquitous Computing, UbiComp '16, Sep. 12-16, 2016, pp. 25-36, Heidelberg, Germany.

Fusang Zhang et al., "From fresnel diffraction model to fine-grained human respiration sensing with commodity wi-fi devices", Proceedings of the ACM on Interactive, Mobile, Wearable and Ubiquitous Technologies, Mar. 2018, pp. 53:1-53:23, vol. 2, No. 1, Article 53.

Phuc Nguyen et al., "Continuous and finegrained breathing volume monitoring from afar using wireless signals," in INFOCOM 2016—The 35th Annual IEEE International Conference on Computer Communications, IEEE, pp. 1-9, IEEE, 2016.

Peilr Hillyard et al., "Experience: Cross-technology radio respiratory monitoring performance study", in Proceedings of the 24th Annual International Conference on Mobile Computing and Networking (MobiCom 2018), Oct. 29-Nov. 2, 2018, pp. 487-496, New Delhi, India.

Feng Zhang et al., "Wispeed: a statistical electromagnetic approach for device-free indoor speed estimation", IEEE Internet of Things Journal, Jun. 2018, pp. 2163-2177, vol. 5, No. 3.

Zhicheng Yang et al., "Vital sign and sleep monitoring using millimeter wave", ACM Transactions on Sensor Networks, Apr. 2017, pp. 14:1-14:32, vol. 13, No. 2, Article 14.

Ossi Kaltiokallio et al., "Non-invasive respiration rate monitoring using a single cots tx-rx pair", in Proceedings of the 13th international symposium on Information processing in sensor networks, IEEE Press, 2014, pp. 59-70.

Neal Patwari et al., "Breathfinding: A wireless network that monitors and locates breathing in a home", IEEE Journal of Selected Topics in Signal Processing, Feb. 2014, pp. 30-42, vol. 8, No. 1.

Peter Hillyard et al., "Comparing respiratory monitoring performance of commercial wireless devices", arXiv preprint arXiv:1807.06767, 2018.

* cited by examiner

| Edge Index | Current State | Next State | Condition | Output |
|---|---|---|---|---|
| 1 | INIT | INIT | $P = 0$ | $\tilde{b}[i] = 0$ |
| 2 | INIT | VER-Enter | $P > 0$ | $\tilde{b}[i] = 0$ |
| 3 | VER-Enter | INIT | $(P = 0) \cup \left(\tilde{b}[i] < b[i-1] - \Delta b\right) \cup \left(\tilde{b}[i] > b[i-1] + \Delta b\right)$ | $\tilde{b}[i] = 0$ |
| 4 | VER-Enter | VER-Enter | $(P > 0) \cap \left(b[i-1] - \Delta b \leq \tilde{b}[i] \leq b[i-1] + \Delta b\right) \cap (\text{cnt}_1 < \text{TH}_1)$ | $\tilde{b}[i] = 0$ |
| 5 | VER-Enter | PF | $(P > 0) \cap \left(b[i-1] - \Delta b \leq \tilde{b}[i] \leq b[i-1] + \Delta b\right) \cap (\text{cnt}_1 == \text{TH}_1)$ | $\tilde{b}[i] = \tilde{b}[i]$ |
| 6 | PF | PF | $P > 0 \cap \left(\tilde{b}[i-1] - \Delta b \leq \tilde{b}[i] \leq \tilde{b}[i-1] + \Delta b\right)$ | $\tilde{b}[i] = \tilde{b}[i]$ |
| 7 | VER-Exit | PF | $P > 0 \cap \left(\tilde{b} - \Delta b \leq \tilde{b}[i] \leq \tilde{b} + \Delta b\right)$ | $\tilde{b}[i] = \tilde{b}$ |
| 8 | PF | VER-Exit | $P = 0 \cup \left(\tilde{b}[i] < b[i-1] - \Delta b\right) \cup \left(\tilde{b}[i] > b[i-1] + \Delta b\right)$ | $\tilde{b}[i] = \tilde{b}$ |
| 9 | VER-Exit | VER-Exit | $!(\text{Edge 7}) \cap (\text{cnt}_2 < \text{TH}_2)$ | $\tilde{b}[i] = \tilde{b}$ |
| 10 | VER-Exit | INIT | $!(\text{Edge 7}) \cap (\text{cnt}_2 == \text{TH}_2)$ | $\tilde{b}[i] = 0$ |

FIG. 9

METHOD, APPARATUS, SERVER AND SYSTEM FOR VITAL SIGN DETECTION AND MONITORING

CROSS-REFERENCE TO RELATED APPLICATIONS

The present application hereby claims priority to, and incorporates by reference the entirety of the disclosures of, each of the following applications:
(a) U.S. patent application Ser. No. 15/326,112, entitled "WIRELESS POSITIONING SYSTEMS", filed on Jan. 13, 2017,
  (1) which is a national stage entry of PCT patent application PCT/US2015/041037, entitled "WIRELESS POSITIONING SYSETMS", filed on Jul. 17, 2015, published as WO 2016/011433A2 on Jan. 21, 2016,
    a. which claims priority to U.S. Provisional patent application 62/148,019, entitled "WIRELESS POSITIONING SYSTEMS", filed on Apr. 15, 2015,
    b. which is a continuation-in-part of U.S. patent application Ser. No. 14/605,611, entitled "WIRELESS POSITIONING SYSTEMS", filed on Jan. 26, 2015, published as US2016/0018508A1 on Jan. 21, 2016,
      1. which claims priority to U.S. Provisional patent application 62/025,795, entitled "TIME-REVERSAL POSITIONING SYSTEMS", filed on Jul. 17, 2014, and
      2. which claims priority to U.S. Provisional patent application 62/069,090, entitled "TIME-REVERSAL POSITIONING SYSTEMS", filed on Oct. 27, 2014,
(b) U.S. patent application Ser. No. 15/584,052, entitled "METHOD, SYSTEM, AND APPARATUS FOR WIRELESS POWER TRANSMISSION BASED ON POWER WAVEFORMING", filed on May 2, 2017,
  (1) which claims priority to U.S. Provisional patent application 62/331,278, entitled "USING VIRTUAL ANTENNAS FOR POWER WAVEFORMING IN WIRELESS POWER TRANSMISSION SYSTEMS", filed on May 3, 2016,
(c) U.S. patent application Ser. No. 15/434,813, entitled "METHODS, DEVICES, APPARATUS, AND SYSTEMS FOR MEDIUM ACCESS CONTROL IN WIRELESS COMMUNICATION SYSTEMS UTILIZING SPATIAL FOCUSING EFFECT", filed on Feb. 16, 2017,
  (1) which claims priority to U.S. Provisional patent application 62/295,970, entitled "THE IMPACT OF SPATIAL FOCUSING EFFECTS ON MEDIUM ACCESS CONTROL DESIGN FOR 5G", filed on Feb. 16, 2016,
  (2) which claims priority to U.S. Provisional patent application 62/320,965, entitled "OPTIMAL RATE ADAPTATION FOR THROUGHPUT MAXIMIZATION IN TIME REVERSAL DIVISION MULTIPLE ACCESS", filed on Apr. 11, 2016,
(d) PCT patent application PCT/US2017/021963, entitled "METHODS, APPARATUS, SERVERS, AND SYSTEMS FOR VITAL SIGNS DETECTION AND MONITORING", filed on Mar. 10, 2017, published as WO2017/156492A1 on Sep. 14, 2017,
  (1) which claims priority to U.S. Provisional patent application 62/307,081, entitled "TR-BREATH: TIME-REVERSAL BREATHING RATE ESTIMATION AND DETECTION", filed on Mar. 11, 2016,
  (2) which claims priority to U.S. Provisional patent application 62/316,850, entitled "TR-BREATH: TIME-REVERSAL BREATHING RATE ESTIMATION AND DETECTION", filed on Apr. 1, 2016,
(e) PCT patent application PCT/US2017/021957, entitled "METHODS, APPARATUS, SERVERS, AND SYSTEMS FOR HUMAN IDENTIFICATION BASED ON HUMAN RADIO BIOMETRIC INFORMATION", filed on Mar. 10, 2017, published as WO2017/156487A1 on Sep. 14, 2017,
  (1) which claims priority to U.S. Provisional patent application 62/307,172, entitled "RADIO SHOT: THROUGH-THE-WALL HUMAN IDENTIFICATION", filed on Mar. 11, 2016,
  (2) which claims priority to U.S. Provisional patent application 62/334,110, entitled "TIME-REVERSAL TRACKING WITHOUT MAPPING", filed on May 10, 2016,
(f) PCT patent application PCT/US2017/027131, entitled "METHODS, APPARATUS, SERVERS, AND SYSTEMS FOR OBJECT TRACKING", filed on Apr. 12, 2017, published as WO2017/180698A1 on Oct. 19, 2017,
  (1) which claims priority to U.S. Provisional patent application 62/322,575, entitled "TIME-REVERSAL RESONATING EFFECT AND ITS APPLICATION IN WALKING SPEED ESTIMATION", filed on Apr. 14, 2016,
  (2) which claims priority to U.S. Provisional patent application 62/334,110, entitled "TIME-REVERSAL TRACKING WITHOUT MAPPING", filed on May 10, 2016, and
  (3) which claims priority to U.S. Provisional patent application 62/409,796, entitled "METHODS, DEVICES, SERVERS, AND SYSTEMS OF TIME REVERSAL BASED TRACKING", filed on Oct. 18, 2016,
(g) U.S. Provisional patent application 62/557,117, entitled "METHODS, DEVICES, SERVERS, APPARATUS, AND SYSTEMS FOR WIRELESS INTERNET OF THINGS APPLICATIONS", filed on Sep. 11, 2017,
(h) U.S. Provisional patent application 62/593,826, entitled "METHOD, APPARATUS, AND SYSTEM FOR OBJECT TRACKING AND NAVIGATION", filed on Dec. 1, 2017,
(i) U.S. patent application Ser. No. 15/384,217, entitled "METHOD, APPARATUS, SERVER, AND SYSTEMS OF TIME-REVERSAL TECHNOLOGY", filed on Dec. 19, 2016, published as US2017/0188359A1 on Jun. 29, 2017,
  (1) which is a Continuation-in-Part of U.S. patent application Ser. No. 13/706,342, entitled "WAVEFORM DESIGN FOR TIME-REVERSAL SYSTEMS," filed on Dec. 5, 2012, issued as U.S. Pat. No. 9,883,511 on Jan. 30, 2018,
  (2) which is a Continuation-in-Part of U.S. patent application Ser. No. 13/969,271, entitled "TIME-REVERSAL WIRELESS SYSTEMS HAVING ASYMMETRIC ARCHITECTURE", filed on Aug. 16, 2013, published as US2015/0049745A1 on Feb. 19, 2015, issued as U.S. Pat. No. 9,882,675 on Jan. 30, 2018,
  (3) which is a Continuation-in-Part of U.S. patent application Ser. No. 13/969,320, entitled "MULTIUSER TIME-REVERSAL DIVISION MULTIPLE ACCESS UPLINK SYSTEM WITH PARALLEL INTERFERENCE CANCELLATION", filed on Aug. 16, 2013, issued as U.S. Pat. No. 9,559,874 on Jan. 31, 2017,
  (4) which is a Continuation-in-Part of U.S. patent application Ser. No. 15/041,677, entitled "HANDSHAKING PROTOCOL FOR TIME-REVERSAL SYSTEM", filed on Feb. 11, 2016, published as US2016/

0164669A1 on Jun. 9, 2016, issued as U.S. Pat. No. 9,794,156 on Oct. 17, 2017,
(5) which is a Continuation-in-Part of U.S. patent application Ser. No. 15/200,430, entitled "QUADRATURE AMPLITUDE MODULATION FOR TIME-REVERSAL SYSTEMS", filed on Jul. 1, 2016, published as US2016/0315797A1 on Oct. 27, 2016, issued as U.S. Pat. No. 9,736,002 on Aug. 15, 2017,
 a. which is a Continuation of U.S. patent application Ser. No. 14/262,153, entitled "QUADRATURE AMPLITUDE MODULATION FOR TIME-REVERSAL SYSTEMS", filed on Apr. 25, 2014, issued as U.S. Pat. No. 9,407,306 on Aug. 2, 2016,
(6) which is a Continuation-in-Part of U.S. patent application Ser. No. 15/200,429, entitled "TIME-REVERSAL WIRELESS PARADIGM FOR INTERNET OF THINGS", filed on Jul. 1, 2016, issued as U.S. Pat. No. 9,781,700 on Oct. 3, 2017,
 a. which is a Continuation of U.S. patent application Ser. No. 14/943,648, entitled "TIME-REVERSAL WIRELESS PARADIGM FOR INTERNET OF THINGS", filed on Nov. 17, 2015, issued as U.S. Pat. No. 9,402,245 on Jul. 26, 2016,
  1. which is a Continuation of U.S. patent application Ser. No. 14/202,651, entitled "TIME-REVERSAL WIRELESS PARADIGM FOR INTERNET OF THINGS", filed on Mar. 10, 2014, issued as U.S. Pat. No. 9,226,304 on Dec. 29, 2015,
(7) which is a Continuation-in-Part of U.S. patent application Ser. No. 14/605,611, entitled "WIRELESS POSITIONING SYSTEM", filed on Jan. 26, 2015, published as US2016/0018508A1 on Jan. 21, 2016,
 a. which claims priority to U.S. Provisional patent application 62/069,090, entitled "TIME-REVERSAL POSITIONING SYSTEMS", filed on Oct. 27, 2014,
 b. which claims priority to U.S. Provisional patent application 62/025,795, entitled "TIME-REVERSAL POSITIONING SYSTEMS", filed on Jul. 17, 2014,
(8) which is a Continuation-in-Part of U.S. patent application Ser. No. 14/615,984, entitled "JOINT WAVEFORM DESIGN AND INTERFERENCE PRE-CANCELLATION FOR TIME-REVERSAL SYSTEMS", filed on Feb. 6, 2015, issued as U.S. Pat. No. 9,686,054 on Jun. 20, 2017,
 a. which claims priority to U.S. Provisional patent application 62/025,795, entitled "TIME-REVERSAL POSITIONING SYSTEMS", filed on Jul. 17, 2014,
(9) which is a Continuation-in-Part of U.S. patent application Ser. No. 15/004,314, entitled "TIME-REVERSAL TECHNOLOGIES FOR HYBRID WIRELESS NETWORKS", filed on Jan. 22, 2016, issued as U.S. Pat. No. 10,014,982 on Jul. 3, 2018,
 a. which claims priority to U.S. Provisional patent application 62/106,395, entitled "TIME-REVERSAL TECHNOLOGIES FOR HYBRID WIRELESS NETWORKS", filed on Jan. 22, 2015,
(10) which is a Continuation-in-Part of U.S. patent application Ser. No. 15/061,059, entitled "TIME-REVERSAL SCALABILITY FOR HIGH NETWORK DENSIFICATION", filed on Mar. 4, 2016,
 a. which claims priority to U.S. Provisional patent application 62/128,574, entitled "TIME-REVERSAL SCALABILITY FOR HIGH NETWORK DENSIFICATION", filed on Mar. 5, 2015,
(11) which is a Continuation-in-Part of PCT patent application PCT/US2015/041037, entitled "WIRELESS POSITIONING SYSTEMS", filed on Jul. 17, 2015, published as WO2016/011433A2 on Jan. 21, 2016,
 a. which claims priority to U.S. Provisional patent application 62/148,019, entitled "WIRELESS POSITIONING SYSTEMS", filed on Apr. 15, 2015,
 b. which is a continuation-in-part of U.S. patent application Ser. No. 14/605,611, entitled "WIRELESS POSITIONING SYSTEMS", filed on Jan. 26, 2015, published as US2016/0018508A1 on Jan. 21, 2016,
  1. which claims priority to U.S. Provisional patent application 62/025,795 entitled "TIME-REVERSAL POSITIONING SYSTEMS", filed on Jul. 17, 2014, and
  2. which claims priority to U.S. Provisional patent application 62/069,090 entitled "TIME-REVERSAL POSITIONING SYSTEMS", filed on Oct. 27, 2014,
(12) which is a Continuation-in-Part of U.S. patent application Ser. No. 15/268,477, entitled "METHODS, DEVICES AND SYSTEMS OF HETEROGENEOUS TIME-REVERSAL PARADIGM ENABLING DIRECT CONNECTIVITY IN INTERNET OF THINGS", filed on Sep. 16, 2016, issued as U.S. Pat. No. 9,887,864 on Feb. 6, 2018,
 a. which claims priority to U.S. Provisional patent application 62/219,315, entitled "ENABLING DIRECT CONNECTIVITY IN INTERNET OF THINGS: A HETEROGENEOUS TIME-REVERSAL PARADIGM", filed on Sep. 16, 2015,
 b. which is a Continuation-in-part of U.S. patent application Ser. No. 15/200,429, entitled "TIME-REVERSAL WIRELESS PARADIGM FOR INTERNET OF THINGS", filed on Jul. 1, 2016, issued as U.S. Pat. No. 9,781,700 on Oct. 3, 2017,
  1. which is a Continuation of U.S. patent application Ser. No. 14/943,648, entitled "TIME-REVERSAL WIRELESS PARADIGM FOR INTERNET OF THINGS", filed on Nov. 17, 2015, issued as U.S. Pat. No. 9,402,245 on Jul. 26, 2016,
   i. which is a Continuation of U.S. patent application Ser. No. 14/202,651, entitled "TIME-REVERSAL WIRELESS PARADIGM FOR INTERNET OF THINGS", filed on Mar. 10, 2014, issued as U.S. Pat. No. 9,226,304 on Dec. 29, 2015,
(13) which is a Continuation-in-Part of U.S. patent application Ser. No. 15/284,496, entitled "TIME-REVERSAL COMMUNICATION SYSTEMS", filed on Oct. 3, 2016,
 a. which claims priority to U.S. Provisional patent application 62/235,958, entitled "SYMBOL TIMING FOR TIME-REVERSAL SYSTEMS WITH SIGNATURE DESIGN", filed on Oct. 1, 2015,
(14) which is a Continuation-in-Part of
 PCT patent application PCT/US2016/066015, entitled "METHOD, APPARATUS, AND SYSTEMS FOR WIRELESS EVENT DETECTION AND MONITORING", filed on Dec. 9, 2016, published as WO2017/100706A1 on Jun. 15, 2017, whose US national stage entry is 16/060,710, filed on Jun. 8, 2018,
 a. which claims priority to U.S. Provisional patent application 62/265,155, entitled "INDOOR EVENTS DETECTION SYSTEM", filed on Dec. 9, 2015, b. which claims priority to U.S. Provisional patent application 62/411,504, entitled "METHOD, APPARATUS, AND SYSTEM FOR WIRELESS INTERNET OF THINGS APPLICATIONS", filed on Oct. 21, 2016,
c. which claims priority to U.S. Provisional patent application 62/383,235, entitled "TIME REVERSAL MONITORING SYSTEM", filed on Sep. 2, 2016,
d. which claims priority to U.S. Provisional patent application 62/307,081, entitled "TR-BREATH: TIME-REVERSAL BREATHING RATE ESTIMATION AND DETECTION", filed on Mar. 11, 2016,
e. which claims priority to U.S. Provisional patent application 62/316,850, entitled "TR-BREATH: TIME-REVERSAL BREATHING RATE ESTIMATION AND DETECTION", filed on Apr. 1, 2016,
(15) which claims priority to U.S. Provisional patent application 62/331,278, entitled "USING VIRTUAL ANTENNAS FOR POWER WAVEFORMING IN WIRELESS POWER TRANSMISSION SYSTEMS", filed on May 3, 2016,
(16) which claims priority to U.S. Provisional patent application 62/295,970, entitled "THE IMPACT OF SPATIAL FOCUSING EFFECTS ON THE MEDIUM ACCESS CONTROL DESIGN FOR 5G", filed on Feb. 16, 2016,
(17) which claims priority to U.S. Provisional patent application 62/320,965, entitled "OPTIMAL RATE ADAPTATION FOR THROUGHPUT MAXIMIZATION IN TIME REVERSAL DIVISION MULTIPLE ACCESS", filed on Apr. 11, 2016,
(18) which claims priority to U.S. Provisional patent application 62/307,081, entitled "TR-BREATH: TIME-REVERSAL BREATHING RATE ESTIMATION AND DETECTION", filed on Mar. 11, 2016,
(19) which claims priority to U.S. Provisional patent application 62/316,850, entitled "TR-BREATH: TIME-REVERSAL BREATHING RATE ESTIMATION AND DETECTION", filed on Apr. 1, 2016,
(20) which claims priority to U.S. Provisional patent application 62/307,172, entitled "RADIO SHOT: THROUGH-THE-WALL HUMAN IDENTIFICATION", filed on Mar. 11, 2016,
(21) which claims priority to U.S. Provisional patent application 62/322,575, entitled "TIME-REVERSAL RESONATING EFFECT AND ITS APPLICATION IN WALKING SPEED ESTIMATION", filed on Apr. 14, 2016,
(22) which claims priority to U.S. Provisional patent application 62/334,110, entitled "TIME-REVERSAL TRACKING WITHOUT MAPPING", filed on May 10, 2016,
(23) which claims priority to U.S. Provisional patent application 62/409,796, entitled "METHODS, DEVICES, SERVERS, AND SYSTEMS OF TIME REVERSAL BASED TRACKING", filed on Oct. 18, 2016,
(24) which claims priority to U.S. Provisional patent application 62/383,235, entitled "TIME REVERSAL MONITORING SYSTEM", filed on Sep. 2, 2016,
(25) which claims priority to U.S. Provisional patent application 62/384,060, entitled "METHODS, DEVICES, SERVERS, SYSTEMS OF TIME REVERSAL MACHINE PLATFORM FOR BROADBAND WIRELESS APPLICATIONS", filed on Sep. 6, 2016,
(26) which claims priority to U.S. Provisional patent application 62/411,504, entitled "METHOD, APPARATUS, AND SYSTEM FOR WIRELESS INTERNET OF THINGS APPLICATIONS", filed on Oct. 21, 2016,
(j) PCT patent application PCT/US2017/015909, entitled "METHODS, DEVICES, SERVERS, APPARATUS, AND SYSTEMS FOR WIRELESS INTERNET OF THINGS APPLICATIONS", filed on Jan. 31, 2017, published as WO2017/155634A1 on Sep. 14, 2017,
  (1) which claims priority to U.S. Provisional patent application 62/384,060, entitled "METHODS, DEVICES, SERVERS, SYSTEMS OF TIME REVERSAL MACHINE PLATFORM FOR BROADBAND WIRELESS APPLICATIONS", filed on Sep. 6, 2016,
  (2) which claims priority to U.S. Provisional patent application 62/331,278, entitled "USING VERTUAL ANTENNAS FOR POWER WAVEFORMING IN WIRELESS POWER TRANSMISSION SYSTEMS", filed on May 3, 2016,
  (3) which claims priority to U.S. Provisional patent application 62/307,081, entitled "TR-BREATH: TIME-REVERSAL BREATHING RATE ESTIMATION AND DETECTION", filed on Mar. 11, 2016,
  (4) which claims priority to U.S. Provisional patent application 62/316,850, entitled "TR-BREATH: TIME-REVERSAL BREATHING RATE ESTIMATION AND DETECTION", filed on Apr. 1, 2016,
  (5) which claims priority to U.S. Provisional patent application 62/322,575, entitled "TIME-REVERSAL RESONATING EFFECT AND ITS APPLICATION IN WALKING SPEED ESTIMATION", filed on Apr. 14, 2016,
  (6) which claims priority to U.S. Provisional patent application 62/334,110, entitled "TIME-REVERSAL TRACKING WITHOUT MAPPING", filed on May 10, 2016,
  (7) which claims priority to U.S. Provisional patent application 62/409,796, entitled "METHODS, DEVICES, SERVERS, AND SYSTEMS OF TIME REVERSAL BASED TRACKING", filed on Oct. 18, 2016,
  (8) which claims priority to U.S. Provisional patent application 62/383,235, entitled "TIME REVERSAL MONITORING SYSTEM", filed on Sep. 2, 2016,
  (9) which claims priority to U.S. Provisional patent application 62/411,504, entitled "METHOD, APPARATUS, AND SYSTEM FOR WIRELESS INTERNET OF THINGS APPLICATIONS", filed on Oct. 21, 2016,
  (10) which claims priority to U.S. Provisional patent application 62/307,172, entitled "RADIO SHOT: THROUGH-THE-WALL HUMAN IDENTIFICATION", filed on Mar. 11, 2016,
  (11) which claims priority to PCT patent application PCT/US2016/066015, entitled "METHOD, APPARATUS, AND SYSTEMS FOR WIRELESS EVENT DETECTION AND MONITORING", filed on Dec. 9, 2016, published as WO2017/100706A1 on Jun. 15, 2017, whose US national stage entry is U.S. patent application Ser. No. 16/060,710, entitled "METHOD, APPARATUS, AND SYSTEMS FOR WIRELESS EVENT DETECTION AND MONITORING", filed on Jun. 8, 2018,
(k) U.S. Provisional patent application 62/678,207, entitled "METHOD, APPARATUS, AND SYSTEM FOR OBJECT TRACKING AND MOTION MONITORING", filed on May 30, 2018, (l) U.S. patent application Ser. No. 15/861,422, entitled "METHOD, APPARATUS, SERVER, AND SYSTEMS OF TIME-REVERSAL TECHNOLOGY", filed on Jan. 3, 2018,
(m) U.S. patent application Ser. No. 15/873,806, entitled "METHOD, APPARATUS, AND SYSTEM FOR OBJECT TRACKING AND NAVIGATION", filed on Jan. 17, 2018.
(n) U.S. patent application Ser. No. 16/101,444, entitled "METHOD, APPARATUS, AND SYSTEM FOR WIRELESS MOTION MONITORING", filed on Aug. 11, 2018.
(o) U.S. Provisional Patent application 62/734,224, entitled "METHOD, APPARATUS, AND SYSTEM FOR WIRELESS SLEEP MONITORING", filed on Sep. 20, 2018.
(p) U.S. Provisional Patent application 62/744,093, entitled "METHOD, APPARATUS, AND SYSTEM FOR WIRELESS PROXIMITY AND PRESENCE MONITORING", filed on Oct. 10, 2018.
(q) U.S. Provisional Patent application 62/753,017, entitled "METHOD, APPARATUS, AND SYSTEM FOR HUMAN IDENTIFICATION BASED ON HUMAN RADIO BIOMETRIC INFORMATION", filed on Oct. 30, 2018.

TECHNICAL FIELD

The present teaching generally relates to vital sign detection and monitoring. More specifically, the present teaching relates to detecting and monitoring vital signs and other periodic motions of an object based on wireless channel information in a rich-scattering environment.

BACKGROUND

Vital signs are important indicators of a person's health and well-being as well as predictors of acute medical conditions and chronic disease states for a person. Breathing rate is one of the most important vital signs, which can be measured by the number of exhalation and inhalation a person takes per minute. In addition, the breathing pattern may be highly correlated to psychological conditions of a human being, such as stress and anxiety.

Many important human vital signs such as breathing are periodic motions. Most traditional approaches for breathing monitoring are invasive in that they need physical contact of the human bodies. For instance, in hospitals, the patients are required to wear oxygen masks, Nasal cannulas, chest straps, or wearable sensors such as thermistors and pressure sensors. Another example is Polysomnography (PSG) used in sleep medicine, which typically requires a minimum of 22 wire attachments to the patient. These dedicated devices are often costly and bulky, create discomfort to the human bodies, and are limited only to clinical settings. Although these wired medical systems can measure breathing using wearables attached onto human body, such systems are clumsy and uncomfortable. To make it worse, the systems themselves would itself distort the very breathing that need to be monitored—as many patients become anxious or annoyed with all the attached wearables and wires.

Currently existing non-invasive (contact-free) breathing monitoring solutions can be categorized as below.

(1) Radar-based breathing monitoring: Doppler radars are often used in breathing monitoring. They are operated by transmitting a signal and receiving a signal with a Doppler shift due to a periodic motion of objects. The breathing rates can be extracted from the Doppler shift. As a drawback, these systems use high transmission power, rely on sophisticated and expensive hardware, and use extremely large bandwidths. A vital sign monitoring system was disclosed utilizing frequency modulated continuous radar (FMCW). It used Universal Software Radio Peripheral (USRP) as the RF front-end to transmit a frequency-sweeping signal. But the additional cost and complexity of the dedicated hardware limited a large-scale deployment of FMCW radar.

(2) Wireless-sensor based breathing monitoring: The received signal strength (RSS) measurements from 802.15.4 compliant sensors on multiple 802.15.4 channels were also used for breathing detection and breathing rate estimation. Dense deployment of wireless sensors is required in these methods as additional wireless infrastructures. In addition, the specific design of frequency-hopping mechanism is required to support multiple channel measurements.

(3) Wi-Fi-based breathing monitoring: RSS is commonly used in the Wi-Fi-based breathing monitoring due to its availability on most commercial Wi-Fi network interface controllers (NICs). Measurements were also used with Wi-Fi devices for breathing estimation. But this method is accurate only when the users hold the Wi-Fi-enabled devices in close proximity to their chests.

In addition to the drawbacks mentioned above, methods (1) and (2) require design and manufacturing of special devices such as specialized radar devices or sensor network nodes, while method (3) has very low accuracy and sensitivity. A wireless breathing monitoring system was proposed to monitor breathing rate and heart rate based on UWB (ultra-wide band) signal. But the UWB-based system has many limitations such as: it has expensive, untested, uncommon, dedicated, limited edition experimental hardware components; it has a small range due to severe absorption of UWB signals by walls; it works only in a line-of-sight (LOS) condition; and it needs very tedious and laborious deployment of many sensors in practical situations to cover a reasonable area, making installation, maintenance and repair very expensive and labor intensive due to the restrictive LOS operation.

Therefore, there is a need for methods and apparatus for vital sign detection and monitoring to solve the above-mentioned problems and to avoid the above-mentioned drawbacks.

SUMMARY

The present teaching generally relates to periodic motion (e.g. human breathing) detection. More specifically, the present teaching relates to periodic motion detection and monitoring based on time-reversal technology in a rich-scattering wireless environment, such as an indoor environment or urban metropolitan area, enclosed environment, underground environment, open-air venue with barriers such as parking lot, storage, yard, square, forest, cavern, valley, etc.

In one embodiment, a system for monitoring object motion in a venue is disclosed. The system comprises a transmitter, a receiver, and a vital sign estimator. The transmitter is located at a first position in the venue and configured for transmitting a wireless signal through a wireless multipath channel impacted by a pseudo-periodic motion of an object in the venue. The receiver is located at a second position in the venue and configured for: receiving the wireless signal through the wireless multipath channel impacted by the pseudo-periodic motion of the object in the venue, and obtaining at least one time series of channel information (CI) of the wireless multipath channel based on the wireless signal. The vital sign estimator is configured for: determining that at least one portion of the at least one time series of CI (TSCI) in a current sliding time window is associated with the pseudo-periodic motion of the object in the venue, and computing a current characteristics related to the pseudo-periodic motion of the object in the current sliding time window based on at least one of: the at least one portion of the at least one TSCI in the current sliding time window, at least one portion of the at least one TSCI in a past sliding time window, and a past characteristics related to the pseudo-periodic motion of the object in the past sliding time window.

In another embodiment, a method for monitoring object motion in a venue is disclosed. The method comprises: receiving a wireless signal through a wireless multipath channel impacted by a pseudo-periodic motion of an object in the venue; obtaining at least one time series of channel information (CI) of the wireless multipath channel based on the wireless signal; determining that at least one portion of the at least one time series of CI (TSCI) in a current sliding time window is associated with the pseudo-periodic motion of the object in the venue; and computing a current characteristics related to the pseudo-periodic motion of the object in the current sliding time window based on at least one of: the at least one portion of the at least one TSCI in the current sliding time window, at least one portion of the at least one TSCI in a past sliding time window, and a past characteristics related to the pseudo-periodic motion of the object in the past sliding time window.

In yet another embodiment, a receiver of a motion monitoring system is disclosed. The motion monitoring system comprises: a transmitter, the receiver, and a vital sign estimator. The receiver comprises: a wireless circuitry, a processor communicatively coupled with the wireless circuitry, a memory communicatively coupled with the processor, and a set of instructions stored in the memory. The wireless circuitry is configured to receive a wireless signal through a wireless multipath channel impacted by a pseudo-periodic motion of an object in a venue, wherein the wireless signal is transmitted asynchronously by the transmitter. The set of instructions, when executed, causes the processor to obtain at least one time series of channel information (CI) of the wireless multipath channel based on the wireless signal. At least one portion of the at least one time series of CI (TSCI) in a current sliding time window is associated with the pseudo-periodic motion of the object in the venue. The at least one portion of the at least one TSCI in the current sliding time window is to be used by the vital sign estimator to compute a current characteristics related to the pseudo-periodic motion of the object in the current sliding time window based on at least one of: the at least one portion of the at least one TSCI in the current sliding time window, at least one portion of the at least one TSCI in a past sliding time window, and a past characteristics related to the pseudo-periodic motion of the object in the past sliding time window.

In still another embodiment, an estimator of a motion monitoring system is disclosed. The motion monitoring system comprises: a transmitter, a receiver, and the estimator. The estimator comprises: a processor, a memory communicatively coupled with the processor, and a set of instructions stored in the memory. The set of instructions, when executed, causes the processor to perform: obtaining at least one time series of channel information (TSCI) of a wireless multipath channel from a receiver of the motion monitoring system, wherein the receiver extracts the at least one TSCI from a wireless signal received from a transmitter of the motion monitoring system through the wireless multipath channel impacted by a pseudo-periodic motion of an object in a venue, determining that at least one portion of the at least one TSCI in a current sliding time window is associated with the pseudo-periodic motion of the object in the venue, and computing a current characteristics related to the pseudo-periodic motion of the object in the current sliding time window based on at least one of: the at least one portion of the at least one TSCI in the current sliding time window, at least one portion of the at least one TSCI in a past sliding time window, and a past characteristics related to the pseudo-periodic motion of the object in the past sliding time window.

In a different embodiment, a system for monitoring a repeating motion in a venue is disclosed. The system comprises a transmitter, a receiver, and a repeating motion monitor. The transmitter is located at a first position in the venue and configured for transmitting a wireless signal through a wireless multipath channel impacted by the repeating motion of an object in the venue. The receiver is located at a second position in the venue and configured for: receiving the wireless signal through the wireless multipath channel impacted by the repeating motion of the object in the venue, and obtaining a time series of channel information (CI) of the wireless multipath channel based on the wireless signal. The repeating motion monitor is configured for: monitoring a periodic characteristics of the repeating motion of the object based on the time series of CI.

In another embodiment, a method for monitoring a repeating motion in a venue is disclosed. The method comprises: receiving a wireless signal through a wireless multipath channel impacted by the repeating motion of an object in the venue; obtaining a time series of channel information (CI) of the wireless multipath channel based on the wireless signal; and monitoring a periodic characteristics of the repeating motion of the object based on the time series of CI.

In yet another embodiment, a receiver of a motion monitoring system is disclosed. The motion monitoring system comprises: a transmitter, the receiver, and a repeating motion monitor. The receiver comprises: a wireless circuitry, a processor communicatively coupled with the wireless circuitry, a memory communicatively coupled with the processor, and a set of instructions stored in the memory. The wireless circuitry is configured to receive a wireless signal through a wireless multipath channel impacted by a repeating motion of an object in a venue. The wireless signal is transmitted by the transmitter. The set of instructions, when executed, causes the processor to obtain a time series of channel information (CI) of the wireless multipath channel based on the wireless signal. The time series of CI is to be used by a repeating motion monitor of the motion monitoring system to monitor a periodic characteristics of the repeating motion.

In still another embodiment, a monitor of a motion monitoring system is disclosed. The motion monitoring system comprises: a transmitter, a receiver, and the monitor. The monitor comprises: a processor, a memory communicatively coupled with the processor, and a set of instructions stored in the memory. The set of instructions, when executed, causes the processor to perform: obtaining a time series of channel information (CI) of a wireless multipath channel from a receiver of the motion monitoring system, wherein the receiver extracts the time series of CI from a wireless signal received from a transmitter of the motion monitoring system through the wireless multipath channel impacted by a repeating motion of an object in a venue, and monitoring a periodic characteristics of the repeating motion of the object based on the time series of CI.

Other concepts are related to software for implementing the present teaching on detecting and monitoring vital signs and other periodic motions based on wireless channel information in a rich-scattering environment.

Additional novel features will be set forth in part in the description which follows, and in part will become apparent to those skilled in the art upon examination of the following and the accompanying drawings or may be learned by production or operation of the examples. The novel features of the present teachings may be realized and attained by practice or use of various aspects of the methodologies, instrumentalities and combinations set forth in the detailed examples discussed below.

BRIEF DESCRIPTION OF DRAWINGS

The methods, systems, and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings.

FIG. 9 illustrates an exemplary state transition of FSM for single-person breathing monitoring, according to one embodiment of the present teaching.

DETAILED DESCRIPTION

Figure 1:
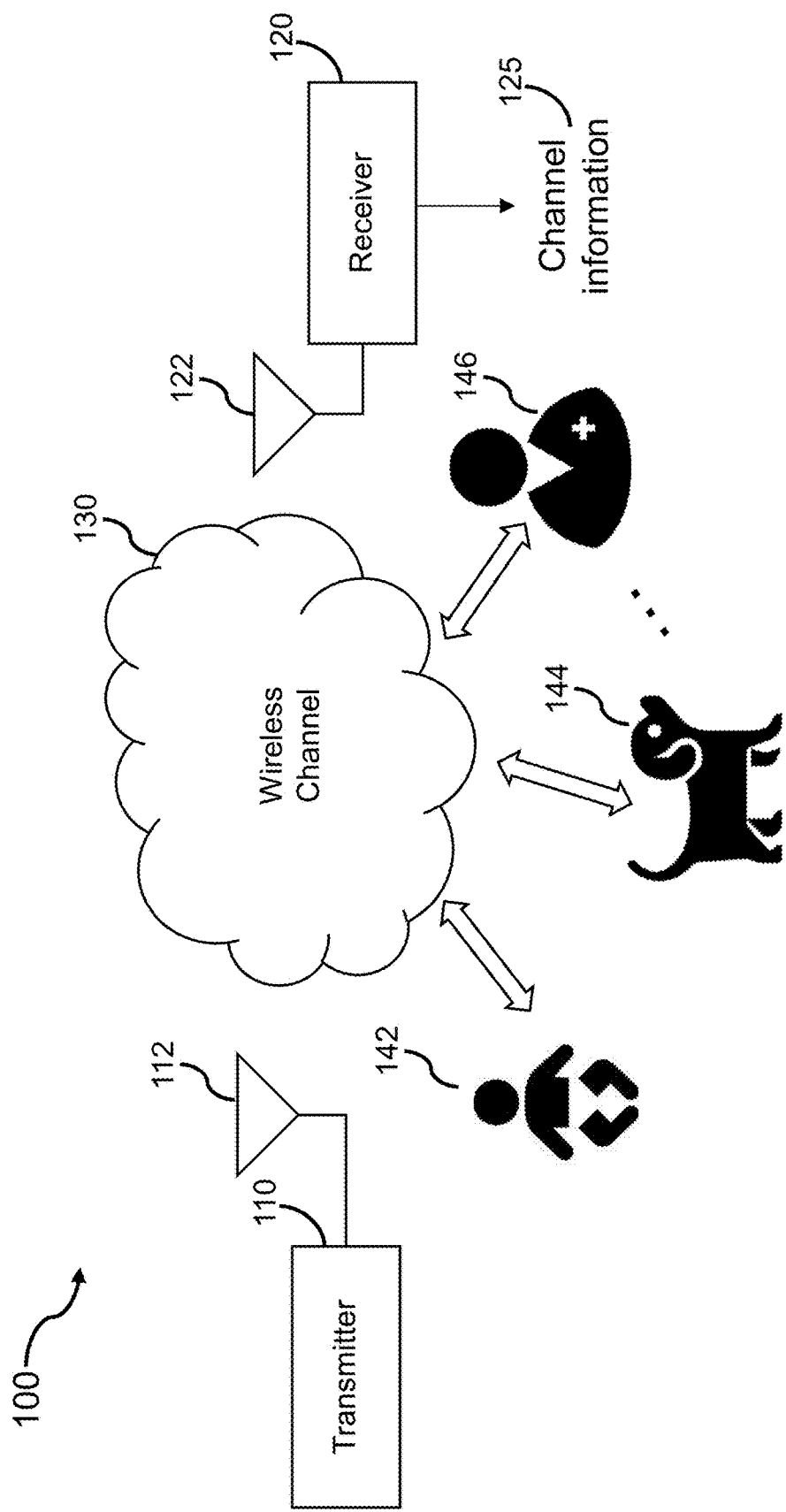
FIG. 1 illustrates an exemplary network environment for vital sign detection and monitoring in a venue, according to one embodiment of the present teaching.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The present teaching discloses systems, apparatus, and methods for detecting and monitoring a periodic or pseudo-periodic object motion in a venue based on a time series of channel information of a wireless multipath channel that is impacted by the object motion. According to various embodiments, the object may be a life (e.g. a human, a pet, an animal, etc.), a device (e.g. a fan, a machine, etc.), or a land; the periodic or pseudo-periodic object motion may represent: breathing, heartbeat, a periodic hand gesture, a periodic gait, a rotation, a vibration, or an earthquake; and the disclosed system can monitor characteristics of the motion, e.g. a rate or frequency of the motion. In the present teaching, the term "pseudo-periodic motion" refers to a periodic motion with slight perturbation, such as a periodic motion with increasing or decreasing frequency, or a combination/sum of two periodic motions with different frequencies. For simplicity, the following description will focus on methods for detecting and monitoring pseudo-periodic motions, while the same disclosed methods can be applied to periodic motion detection and monitoring as well.

According to various embodiments, each channel information (CI) may comprise at least one of: a channel state information (CSI), a frequency domain CSI, a frequency domain CSI associated with at least one sub-band, a time domain CSI, a CSI in a domain, a channel impulse response (CIR), a channel frequency response (CFR), a channel characteristics, a channel filter response, a CSI of the wireless multipath channel, an information of the wireless multipath channel, a time stamp, an auxiliary information, a data, a meta data, a user data, an account data, an access data, a security data, a session data, a status data, a supervisory data, a household data, an identity (ID), a device data, a network data, a neighborhood data, an environment data, a real-time data, a sensor data, a stored data, an encrypted data, a compressed data, a protected data, and/or another channel information. In one embodiment, the disclosed system has hardware components (e.g. wireless transmitter/receiver with antenna, analog circuitry, power supply, processor, memory, etc.) and corresponding software components. According to various embodiments of the present teaching, the disclosed system includes a Bot (referred to as a Type 1 device) and an Origin (referred to as a Type 2 device) for vital sign detection and monitoring. Each device comprises a transceiver, a processor and a memory.

In one embodiment, a robust vital sign monitoring system is disclosed to analyze the tiny temporal variations in the CFRs. On each antenna link, the system transforms CFRs into CIRs and performs spectral analysis on the CIRs via fast Fourier transform (FFT). The spectrum of different antenna links are then fused into one averaged spectrum. Then, persistence-based peak detection is performed on the spectrum which finally leads to the repetition rate (e.g. breathing rate) estimation. Furthermore, FSM is introduced into the disclosed system such that the vital sign monitoring system would adopt different thresholds in different states, which significantly improves the robustness of vital sign monitoring. Experimental results validate that the system could perform well for single-person as well as multi-person breathing tracking.

In one embodiment, the disclosed system uses CSI from regular off-the-shelf WiFi chips which are affordable, widely available, standard compliant, interoperable, FCC approved, with quality control and technical support by reputable brand. These components (WiFi chips, modules, design tools, knowhow) are much more affordable, much more widely available and much richer than the expensive, untested, uncommon, dedicated, limited edition experimental hardware components of an existing system. The disclosed system has a large effective range, due to the large WiFi coverage. The disclosed system can work in both line-of-sight (LOS) and non-line-of-sight (NLOS) conditions. The disclosed system may also use CSI from chips associated with 4G, LTE, LTE-U, 5G and beyond.

The disclosed system includes features that are significantly more than an abstract idea. To measure human breathing remotely without wearables has been a dream for decades. The disclosed system solves the long-time problem using physical WiFi chips as sensors to monitor the environment with WiFi signals and the associated multipath patterns. The disclosed system has hardware components (e.g. Type 1 device, Type 2 device each with processor, memory, wireless transceivers, cloud server, etc.). The WiFi signals are electromagnetic (EM) waves in the air which are measurable and with deterministic structure and frequency characteristics. The system has matching software components (e.g. embedded software in Type 1 device, in Type 2 device, in servers, etc.). The software can interface with low-level WiFi chips and firmware to extract CSI. Experimental results show that the disclosed system can detect human breathing rate with very high accuracy.

The disclosed system can be applied in many cases. In one example, the Type 1 device (transmitter) may be a small WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug, etc. In one example, the Type 2 (receiver) may be a WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug, etc. The Type 1 device and Type 2 devices may be placed in/near a conference room to count people. The Type 1 device and Type 2 devices may be in a well-being monitoring system for older adults to monitor their daily activities and any sign of symptoms (e.g. dementia, Alzheimer's disease). The Type 1 device and Type 2 device may be used in baby monitors to monitor the vital signs (breathing) of a living baby. The Type 1 device and Type 2 devices may be placed in bedrooms to monitor quality of sleep and any sleep apnea. The Type 1 device and Type 2 devices may be placed in cars to monitor well-being of passengers and driver, detect any sleeping of driver and detect any babies left in a car. The Type 1 device and Type 2 devices may be used in logistics to prevent human trafficking by monitoring any human hidden in trucks and containers. The Type 1 device and Type 2 devices may be deployed by emergency service at disaster area to search for trapped victims in debris. The Type 1 device and Type 2 devices may be deployed in an area to detect breathing of any intruders. There are numerous applications of wireless breathing monitoring without wearables.

Hardware modules may be constructed to contain either the Type 1 transceiver and the Type 2 transceiver. The hardware modules may be sold to/used by variable brands to design, build and sell final commercial products. Products using the disclosed system and/or method may be home/office security products, sleep monitoring products, WiFi products, mesh products, TV, STB, entertainment system, HiFi, speaker, home appliance, lamps, stoves, oven, microwave oven, table, chair, bed, shelves, tools, utensils, torches, vacuum cleaner, smoke detector, sofa, piano, fan, door, window, door/window handle, locks, smoke detectors, car accessories, computing devices, office devices, air conditioner, heater, pipes, connectors, surveillance camera, access point, computing devices, mobile devices, LTE devices, 3G/4G/5G/6G devices, gaming devices, eyeglasses, glass panels, VR goggles, necklace, watch, waist band, belt, wallet, pen, hat, wearables, implantable device, tags, parking tickets, smart phones, etc.

In addition, sleep monitoring acts as a critical and challenging task that attracts increasing demands and interests.

The present teaching discloses the model, design, and implementation of SMARS (Sleep Monitoring via Ambient Radio Signals), which is the first practical Sleep Monitoring system that exploits Ambient Radio Signals to recognize sleep stages and assess sleep quality. This will enable a future smart home that monitors daily sleep in a ubiquitous, non-invasive and contactless manner, without instrumenting the subject's body or the bed. Different from previous RF-based approaches, the present teaching devises a statistical model that accounts for all reflecting and scattering multipaths, allowing highly accurate and instantaneous breathing estimation with ever best performance achieved on commodity devices. On this basis, SMARS then recognizes different sleep stages, including wake, REM, and NREM, which is previously only possible with dedicated hardware. A real-time system is implemented on commercial WiFi chipsets and deployed in 6 homes with 6 participants, resulting in 32 nights of data in total. The results demonstrate that SMARS yields a median error of 0.47 bpm and a 95% error of only 2.92 bpm for breathing estimation, and detects breathing robustly even when a person is 10 m away from the link, or behind a wall. SMARS achieves sleep staging accuracy of 85%, outperforming advanced solutions using contact sensor or radar. Furthermore, SMARS is evaluated upon a recently released dataset that measures 20 patients' overnight sleep, which confirms the performance. By achieving promising results with merely a single commodity RF link, SMARS will set the stage for a practical in-home sleep monitoring solution.

Sleep plays a vital role in an individual's health and well-being, both mentally and physically. It is well recognized that sleep quantity and quality is fundamentally related to health risks like cardiovascular decease, stroke, kidney failure, diabetes, and adverse mental conditions, etc. Unfortunately, in modern society, a number of people suffer from sleep disorders. As recently reported, 10% of the population suffers from chronic insomnia (which is even higher among elders), and ⅓ of Americans do not get sufficient sleep. Monitoring sleep emerges as an essential demand to help, manage, diagnose, and treat the growing group of sleep disorders as well as to keep regular tabs on personal health.

Sleep monitoring, however, is a challenging task that has drawn tremendous efforts for decades. Generally, it measures sleep time, recognizes different sleep stages, e.g., wake, REM (Rapid Eye Movement) and NREM (Non-REM), and accordingly assesses an individual's sleep quality. Various solutions have been proposed. The medical gold standard relies on Polysomnography (PSG), which monitors various physiological parameters such as brain activities, respirations, and body movements by a number of wired sensors attached to the patient. Albeit accurate and comprehensive, PSG is usually expensive and cumbersome with the invasive sensors that may cause sleep difficulties, limiting itself to clinical usage for confirmed patients. Other approaches including photoplethysmography (PPG) and actigraphy (ACT) require users to wear dedicated sensors during sleep. Ballistocardiogram (BCG) needs to instrument the mattress with an array of EMFi sensors to measure ballistic force. Despite of the costs, these approaches provide suitable solutions for those who need special cares but are less-than-ideal for the public. Recent efforts in mobile computing envision in-home sleep monitoring using smartphones and wearables. These methods, however, only provide coarse-grained, less accurate measurements and fail to monitor vital signs like respiratory rate. In addition, mobiles and wearables are undesirable for especially elders and those with dementia.

Different from prevailing solutions, the disclosed solution looks forward to a future smart home that monitors daily sleep in a ubiquitous, non-invasive, contactless, and accurate manner, without instrumenting the body or the bed. One can observe an opportunity towards such a system by two perspectives: 1) Clinical study has shown that physiological activity varies among different sleep stages. For example, breathing rate becomes irregular and fast since brain oxygen consumption increases during REM sleep, and is more stable and slower during NREM sleep, rendering the feasibility of sleep staging based on breathing monitoring. 2) Recent advances in wireless technology have demonstrated non-contact sensing of body motions in the environments. Chest and abdomen motions caused by breathing can alter radio signal propagations and thus modulate the received signals, from which it is then possible to decipher breathing. One can explore a synergy between the two perspectives, resulting in a system to leverage ambient radio signals (e.g., WiFi) to capture a person's breathing and motion during sleep and further monitor the sleep behaviors.

While early works have investigated the feasibility of RF-based breathing estimation and sleep monitoring, they either rely on specialized hardware like FMCW radar, or only work in controlled environments. Solutions based on dedicated radios are usually expensive and not ubiquitously applicable. Others using commodity devices typically require the user to lay still on a bed with radios exceedingly close to his/her chest and fail in presence of extraneous motions or in Non-Line-Of-Sight (NLOS) scenarios. In addition, none of them can identify different sleep stages due to their limited accuracy in breathing estimation. Such limitations prevent them from application for practical in-home sleep monitoring.

The present teaching disclose the model, design, and implementation of SMARS, the first practical Sleep Monitoring system that exploits commodity Ambient Radio Signals to recognize sleep stages and assess the otherwise elusive sleep quality. SMARS works in a non-obtrusive way without any body contact. All that a user needs to do is to set up one single link between two commodity radios by, e.g., simply placing a receiver if a wireless router is already installed inside the home. SMARS advances the literature by a novel statistical model that allows highly accurate and instantaneous breathing estimation. On this basis, SMARS is able to distinguish different sleep stages, which is previously only obtainable by expensive dedicated hardware. Specifically, SMARS excels in three unique aspects to deliver practical sleep monitoring. First, one can devise a statistical model on motion in Channel State Information (CSI) that leverages all reflection and scattering multipaths indoors. Existing works usually assume a geometrical model with a few multipaths and one major path reflected off the human body (e.g., using a 2-ray model developed for outdoor space). Under real-world indoor environments, however, there could be as many as hundreds of multipaths, and signals not only reflect but also scatter off a person's body and other objects in the space. As a consequence, previous approaches fail in NLOS environments and for minute motions due to the lack of a dominant reflection path. In contrast, the disclosed model investigates the statistical characteristics of motion in CSI without making such unrealistic assumptions, underlying robust detection of arbitrary motions including breathing.

Second, SMARS achieves accurate respiratory rate estimation instantaneously and robustly. Most of previous breathing estimation schemes assume constant breathing rate during a relatively large time window to gain sufficient frequency resolution, losing fine-grained breathing variations during sleep. In addition, minute breathing motions can be easily buried in CSI measurement noises, rendering existing philosophies effective only in extraordinary close proximity (typically within 2-3 m) without any extraneous motions. To improve time resolution, SMARS exploits the time-domain Auto-Correlation Function (ACF) to estimate breathing rate, which can report real-time breathing rates as frequent as every one second and make it possible to capture instantaneous breathing rate changes. By using ACF, SMARS also circumvents the use of noisy phase and the usually handcrafted CSI denoising procedure. More importantly, by eliminating the frequency offsets and thus synchronizing breathing signal over different subcarriers, ACF allows us to perform Maximal Ratio Combining (MRC) to combine multiple subcarriers to combat measurement noises and maximize breathing signals in an optimal way. By doing so, one can push the limit of the breathing signal to noise ratio (SNR) and thus significantly increase the sensing sensitivity for larger coverage as well as weaker breathing. Specifically, SMARS can reliably detect breathing when a person is 10 m away from the link, or behind a wall, which is even better than specialized low-power radars.

Finally, based on the extracted breathing rates and motion statistics during sleep, one can recognize different sleep stages (including wake, REM and NREM) and comprehensively assess the overall sleep quantity and quality. Based on in-depth understanding of the relationship between breathing rates and sleep stages, one can extract distinctive breathing features for classification for sleep staging. None of existing works using off-the-shelf devices can achieve the same goal of staging sleep.

A real-time system has been implemented on different commercial WiFi chipsets and its performance is evaluated through extensive experiments. The evaluation includes two parts: 1) One can deploy SMARS in 6 homes with 6 healthy subjects and collect 32 nights of data, 5 out of which have PSG data recorded by commercial devices. The results show that SMARS achieves great performance, with a median breathing estimation error of 0.47 breath per minute (bpm) and a 95% tile error of 2.92 bmp. Regarding sleep staging, SMARS produces a remarkable accuracy of 85.2%, while commercial solutions, e.g., EMFIT based on contact sensors and ResMed using radar, have accuracies of only 69.8% and 83.7% respectively. 2) One can further validate SMARS on a recently released dataset on RF-based respiration monitoring. The dataset collected 20 patients' overnight sleep for comparative evaluation of four state-of-the-art breathing monitoring systems, using clinically labeled PSG data as ground truths. All the four systems (based on ZigBee, Sub-RSS radio, UWB radar, and WiFi CSI, respectively) produce significant median errors of about 2-3 bpm and 95% tile errors of around or above 10 bpm. As comparison, SMARS achieves significant improvements by decreasing the median error to 0.66 bpm and the 95% tile error to 3.79 bpm. By achieving promising performance, SMARS can deliver clinically meaningful sleep monitoring for daily and regular use in practice and takes an important step towards a future smart home that monitors personal health everyday life.

In a nutshell, the core contribution here is SMARS, the first system that enables a smart home to stage an inhabitant's sleep using commodity off-the-shelf WiFi devices, by achieving highly accurate and instantaneous breathing estimation in the wild. SMARS also contributes the first statistical model for understanding and capturing motions in CSI, which will renovate various applications in wireless sensing.

In one embodiment, the present teaching discloses a method, an apparatus, a device, a system, and/or software (method/apparatus/device/system/software) of a wireless monitoring system. A time series of channel information (CI) of a wireless multipath channel may be obtained using a processor, a memory communicatively coupled with the processor and a set of instructions stored in the memory. The time series of CI may be extracted from a wireless signal transmitted between a Type 1 heterogeneous wireless device and a Type 2 heterogeneous wireless device in a venue through the wireless multipath channel. The wireless multipath channel may be impacted by a motion of an object in the venue. A characteristics and/or a spatial-temporal information of the object and/or of the motion of an object may be monitored based on the time series of CI. A task may be performed based on the characteristics and/or the spatial-temporal information. A presentation associated with the task may be generated in a user-interface (UI) on a device of a user. The time series of CI may be preprocessed.

The Type 1 device may comprise at least one heterogeneous wireless transmitter. The Type 2 device may comprise at least one heterogeneous wireless receiver. The Type 1 device and the Type 2 device may be the same device. Any device may have a processor, a memory communicatively coupled with the processor, and a set of instructions stored in the memory to be executed by the processor.

There may be multiple Type 1 heterogeneous wireless devices interacting with the same Type 2 heterogeneous wireless device, and/or there may be multiple Type 2 heterogeneous wireless devices interacting with the same Type 1 heterogeneous wireless device. The multiple Type 1 devices/Type 2 devices may be synchronized and/or asynchronous, with same/different window width/size and/or time shift. The multiple Type 1 devices/Type 2 devices may operate independently and/or collaboratively. The multiple Type 1 devices/Type 2 devices may be communicatively coupled to same or different servers (e.g. cloud server, edge server, local server). Operation of one device may be based on operation, state, internal state, storage, processor, memory output, physical location, computing resources, network of another device. Difference devices may communicate directly, and/or via another device/server/cloud server. The devices may be associated with one or more users, with associated settings. The settings may be chosen once, pre-programmed, and/or changed over time.

In the case of multiple Type 1 devices interacting with multiple Type 2 devices, any processing (e.g. time domain processing and/or frequency domain processing) may be different for different devices. The processing may be based on locations, orientation, direction, roles, user-related characteristics, settings, configurations, available resources, available bandwidth, network connection, hardware, software, processor, co-processor, memory, battery life, available power, antennas, antenna types, directional/unidirectional characteristics of the antenna, power setting, and/or other parameters/characteristics of the devices.

The wireless receiver (e.g. Type 2 device) may receive the wireless signal and/or another wireless signal from the wireless transmitter (e.g. Type 1 device). The wireless receiver may receive another wireless signal from another wireless transmitter (e.g. a second Type 1 device). The wireless transmitter may transmit the wireless signal and/or another wireless signal to another wireless receiver (e.g. a second Type 2 device). The wireless transmitter, the wireless receiver, the another wireless receiver and/or the another wireless transmitter may be moving with the object and/or another object. The another object may be tracked.

The Type 1 device may be capable of wirelessly coupling with at least two Type 2 devices. The Type 2 device may be capable of wirelessly coupling with at least two Type 1 devices. The Type 1 device may be caused to switch/establish wireless coupling from the Type 2 device to a second Type 2 heterogeneous wireless device at another location in the venue. Similarly, the Type 2 device may be caused to switch/establish wireless coupling from the Type 1 device to a second Type 1 heterogeneous wireless device at yet another location in the venue. The switching may be controlled by a server, the processor, the Type 1 device, the Type 2 device, and/or another device. The radio used before switching may be different from the radio used after the switching. A second wireless signal may be caused to be transmitted between the Type 1 device and the second Type 2 device (or between the Type 2 device and the second Type 1 device) through the wireless multipath channel. A second time series of CI of the wireless multipath channel extracted from the second wireless signal may be obtained. The second wireless signal may be the first wireless signal. The characteristics, the spatial-temporal information and/or another quantity of the motion of the object may be monitored based on the second time series of CI. The Type 1 device and the Type 2 device may be the same device.

The wireless signal and/or the another wireless signal may have data embedded. The wireless receiver, the wireless transmitter, the another wireless receiver and/or the another wireless transmitter may be associated with at least one processor, memory communicatively coupled with respective processor, and/or respective set of instructions stored in the memory which when executed cause the processor to perform any and/or all steps needed to determine the spatial-temporal information, the initial spatial-temporal information, the initial time, the direction, the instantaneous location, the instantaneous angle, and/or the speed, of the object.

The processor, the memory and/or the set of instructions may be associated with the Type 1 heterogeneous wireless transceiver, one of the at least one Type 2 heterogeneous wireless transceiver, the object, a device associated with the object, another device associated with the venue, a cloud server, and/or another server.

The Type 1 device may transmit the wireless signal (e.g. a series of probe signals) in a broadcasting manner to at least one Type 2 device(s) through the wireless multipath channel in the venue. The wireless signal is transmitted without the Type 1 device establishing wireless connection with any of the at least one Type 2 device receiver(s).

The Type 1 device may transmit to a particular destination media access control (MAC) address common for more than one Type 2 devices. Each of the more than one Type 2 devices may adjust their MAC address to the particular MAC address.

The particular destination MAC address (common destination MAC address) may be associated with the venue. The association may be recorded in an association table of an Association Server. The venue may be identified by the Type 1 device, a Type 2 device and/or another device based on the particular destination MAC address, the series of probe signals, and/or the at least one time series of CI extracted from the probe signals.

For example, a Type 2 device may be moved to a new location in the venue (e.g. from another venue). And the Type 1 device may be newly set up in the venue such that the Type 1 device and the Type 2 device are not aware of the existence of each other, and they may not establish wireless connection at all. During set up, the Type 1 device may be instructed/guided/caused/controlled to send the series of probe signals to the particular destination MAC address (e.g. using a dummy receiver, using a hardware pin setting/connection, using a stored setting, using a local setting, using a remote setting, using a downloaded setting, or using a server). Upon power up, the Type 2 device may scan for probe signals according to a table of destination MAC addresses that may be used at different locations (e.g. different MAC address for different venue such as house, office, enclosure, floor, multi-storey building, store, airport, mall, stadium, hall, station, subway, lot, area, zone, region, district, city, country, continent). When the Type 2 device detects the probe signals sent to the particular destination MAC address, the Type 2 device can use the table to identify the venue based on the particular destination MAC address.

A location of a Type 2 device in the venue may be computed based on the particular destination MAC address, the series of probe signals, and/or the at least one time series of CI obtained by the Type 2 device from the probe signals. The computing may be performed by the Type 2 device.

The particular destination MAC address may be changed over time. It may be changed according to a time table, a rule, a policy, a mode, a condition, a situation and/or a change. The particular destination MAC address may be selected based on availability of the MAC address, a pre-selected list, collision pattern, traffic pattern, data traffic between the Type 1 device and another device, effective bandwidth, random selection, and/or a MAC address switching plan. The particular destination MAC address may be the MAC address of a second wireless device (e.g. a dummy receiver, or a receiver that serves as a dummy receiver).

The Type 1 device may transmit the probe signals in a channel selected from a set of channels. At least one CI of the selected channel may be obtained by a respective Type 2 device from the probe signal transmitted in the selected channel.

The selected channel may be changed over time. The change may be according to a time table, a rule, a policy, a mode, a condition, a situation, and/or a change. The selected channel may be selected based on availability of channels, a pre-selected list, co-channel interference, inter-channel interference, channel traffic patterns, data traffic between the Type 1 device and another device, effective bandwidth associated with channels, a security criterion, random selection, a channel switching plan, a criterion, and/or a consideration.

The particular destination MAC address and/or an information of the selected channel may be communicated between the Type 1 device and a server through a network. The particular destination MAC address and/or the information of the selected channel may also be communicated between a Type 2 device and a server through another network. The Type 2 device may communicate the particular destination MAC address and/or the information of the selected channel to another Type 2 device (e.g. via a mesh network, via Bluetooth, via WiFi, etc). The particular destination MAC address and/or the information of the selected channel may be chosen by a server. The particular destination MAC address and/or the information of the selected channel may be signaled in an announcement channel by the Type 1 device and/or a server. Before the particular destination MAC address and/or the information of the selected channel is being communicated, it may be pre-processed.

Wireless connection between the Type 1 device and another wireless device may be established. The Type 1 device may send a first wireless signal (e.g. a sounding frame, a probe signal, a request-to-send RTS) to the another wireless device. The another wireless device may reply by sending a second wireless signal (e.g. a command, or a clear-to-send CTS) to the Type 1 device, triggering the Type 1 device to transmit the wireless signal (e.g. series of probe signals) in the broadcasting manner to the at least one Type 2 device without establishing wireless connection with any of the at least one Type 2 device. The second wireless signal may be a response or an acknowledge (e.g. ACK) to the first wireless signal. The second wireless signal may contain a data with information of at least one of: the venue, and the Type 1 device. The first wireless signal may also be in response to the second wireless signal.

The another wireless device may be a dummy wireless device with a purpose (e.g. a primary purpose, a secondary purpose) to establish the wireless connection with the Type 1 device, to receive the first wireless signal, and/or to send the second wireless signal. The another wireless device may be physically attached to the Type 1 device.

In another example, the another wireless device may send a third wireless signal to the Type 1 device triggering the Type 1 device to transmit the wireless signal (e.g. series of probe signals) in the broadcasting manner to the at least one Type 2 device without establishing wireless connection with any of the at least one Type 2 device. The Type 1 device may reply to the third wireless signal by transmitting a fourth wireless signal to the another wireless device.

The another wireless device may not communicate further with the Type 1 device after establishing the connection with the Type 1 device. The another wireless device may suspend communication with the Type 1 device after establishing the connection. The communication may be resumed in the future. The another wireless device may enter an inactive mode, a hibernation mode, a sleep mode, a stand-by mode, a low-power mode, an OFF mode and/or a power-down mode, after establishing the wireless connection with the Type 1 device.

The another wireless device may have the particular destination MAC address. It may use the wireless connection to trigger the Type 1 device to send the at least one series of probe signals in a broadcasting manner to the particular destination MAC address. Each of the at least one Type 2 device may set its MAC address to the particular destination MAC address so as to receive the at least one series of probe signals from the Type 1 device. A new Type 2 device in the venue may obtain the particular destination MAC address from a designated source (e.g. a cloud server, an edge server, a remote server, a local server, a web server, an internet server, a webpage, a database) and set its MAC address to the particular destination MAC address so as to receive the at least one series of probe signals from the Type 1 device Both the Type 1 device and the another wireless device may be controlled and/or coordinated by at least one of: a first processor associated with the Type 1 device, a second processor associated with the another wireless device, a third processor associated with the designated source and/or a fourth processor associated with another device. The first processor and the second processor may coordinate with each other.

A first series of probe signals may be transmitted by a first antenna of the Type 1 device to at least one first Type 2 device through a first wireless multipath channel in a first venue. A second series of probe signals may be transmitted by a second antenna of the Type 1 device to at least one second Type 2 device through a second wireless multipath channel in a second venue. The first series and the second series may/may not be different. The at least one first Type 2 device may/may not be different from the at least one second Type 2 device. The first series and/or the second series of probe signals may be transmitted in a broadcasting manner. The first antenna may/may not be different from the second antenna.

The Type 1 device may send the two separate series of probe signals to two separate groups of Type 2 devices located in two venues. The first set of Type 2 devices (the at least one first Type 2 device) may receive the first time series of probe signals through a first wireless multipath channel of the first venue. The second set of Type 2 devices (the at least one second Type 2 device) may receive the second time series of probe signals through a second wireless multipath channel in the second venue. If in broadcasting mode, Type 1 device may not establish wireless connection with any of the at least one first and second Type 2 devices.

The two venues may have different sizes, shape, multipath characteristics. The first venue and the second venue may overlap partially. The immediate area around the first antenna and second antenna may be part of the overlapped area. The first venue may be a subset of the second venue, or vice versa. The first wireless multipath channel and the second wireless multipath channel may be different. For example, the first one may be WiFi while the second may be LTE. Or, both may be WiFi, but the first one may be 2.4 GHz WiFi and the second may be 5 GHz WiFi. Or, both may be 2.4 GHz WiFi, but may have different channel numbers, with different SSID names, and WiFi settings (e.g. encryption—the first may use PKA and the second may use PKA2).

Each first Type 2 device may obtain at least one first time series of CI from the first series of probe signals, the CI being of the first wireless multipath channel between the first Type 2 device and the Type 1 device. Each second Type 2 device may obtain at least one second time series of CI from the second series of probe signals, the CI being of the second wireless multipath channel between the second Type 2 device and the Type 1 device.

The first antenna may/may not be the second antenna. The at least one first Type 2 device may/may not be the same as the at least one second Type 2 device. A particular first Type 2 device may be the same as a particular second Type 2 device. The first and second series of probe signals may/may not be synchronous. The transmission of the first series of probe signals may not be synchronous to the transmission of the second series of probe signals. A probe signal may be transmitted with data. A probe signal may be replaced by a data signal.

The first series of probe signals may be transmitted at a first pseudo-regular interval (e.g. at a rate of 30 Hz). The second series of probe signals may be transmitted at a second pseudo-regular interval (e.g. at a rate of 300 Hz). The first pseudo-regular interval may/may not be different from the second pseudo-regular interval. The first and/or second pseudo-regular interval may be changed over time. The change may be according to at least one of: a time table, a rule, a policy, a mode, a condition, a situation, and/or a change. Any pseudo-regular interval may be changed over time.

The first series of probe signals may be transmitted to a first destination MAC address. The second series of probe signals may be transmitted to a second destination MAC address. The two destination MAC addresses may/may not be different. Any of the two destination MAC addresses may be changed over time. The change may be according to at least one of: a time table, a rule, a policy, a mode, a condition, a situation, and/or a change.

The first series of probe signals may be transmitted in a first channel. The second series of probe signals may be transmitted in a second channel. The first channel and the second channel may/may not be different. The first channel and/or the second channel may be changed over time. The change may be according to at least one of: a time table, a rule, a policy, a mode, a condition, a situation, and/or a change.

A first wireless connection may be established between the Type 1 device and another wireless device. The Type 1 device may establish the first wireless connection with the another wireless device. The Type 1 device may send a first wireless signal to the another wireless device. The another wireless device may send a second wireless signal to the Type 1 device. One of the first wireless signal and the second wireless signal may be in response to the other. The second wireless signal to the Type 1 device may trigger the Type 1 device to transmit the first series of probe signals in the broadcasting manner. The second wireless signal may be an acknowledge to the first wireless signal.

A second wireless connection may be established between the Type 1 device and yet another wireless device. The Type 1 device may establish the second wireless connection with the yet another wireless device. The Type 1 device may send a third wireless signal to the yet another wireless device. The yet another wireless device may send a fourth wireless signal to the Type 1 device. One of the third wireless signal and the fourth wireless signal may be in response to the other. The fourth wireless signal to the Type 1 device may trigger the Type 1 device to transmit the second series of probe signals in the broadcasting manner. The fourth wireless signal may be an acknowledge to the third wireless signal. The third wireless signal may be similar to the first wireless signal. The fourth wireless signal may be similar to the second wireless signal. The yet another wireless device may be the another wireless device. The third wireless signal may be sent by the Type 1 device before the first wireless communication is fully established and/or completed.

The another wireless device and the yet another wireless device may be the same device, which may perform signal handshake (e.g. the handshake with the first wireless signal and second wireless signal, or the handshake with the third signal and the fourth signal) with all Type 1 devices sequentially to trigger them to transmit in the broadcasting manner. The signal handshake with the Type 1 devices may be performed in at least one of: a sequential manner, a parallel manner and a mixed manner (partially sequential, partially parallel).

The Type 1 device, the another wireless device and/or the yet another wireless device may be controlled and/or coordinated, physically attached, or may be of/in/of a common device. At least two of the Type 1 device, the another wireless device and/or the yet another wireless device may be controlled by/connected to a common data processor, or may be connected to a common bus interconnect/network/LAN/Bluetooth network/BLE network/wired network/wireless network/mesh network/mobile network/cloud, or may share a common memory, or may be associated with a common user/user profile/user account/identity (ID)/household/house/physical address/location/geographic coordinate/IP subnet/SSID/user device/home device/office device/manufacturing device.

The Type 1 device, the another wireless device and/or the yet another wireless device may each be associated a processor, a memory communicatively coupled with the processor, and a set of instruction stored in the memory to be executed by the processor. The Type 1 device, the another wireless device and/or the yet another wireless device may each comprise a processor, a memory communicatively coupled with the processor, and a set of instruction stored in the memory to be executed by the processor. When executed, the set of instructions may cause the device to perform an operation. Their processors may be coordinated.

At least one series of probe signals may be transmitted asynchronously and contemporaneously by each of more than one Type 1 heterogeneous wireless devices. Each respective series of probe signals is transmitted by an antenna of respective Type 1 heterogeneous wireless device in a broadcasting manner to a respective set of Type 2 devices through a wireless multipath channel, without the respective Type 1 device establishing wireless connection with any of the respective set of Type 2 receivers.

The transmitting may be using a respective processor, a respective memory and a respective set of instructions. Each of the more than one Type 1 heterogeneous wireless devices may have a heterogeneous integrated circuit (IC). Each of the respective set of Type 2 Type 2 device may have a respective heterogeneous IC.

Each Type 1 device may be the signal source of a set of respective Type 2 devices (i.e. the Type 1 device sends a respective wireless signal (series of probe signals) to the set of respective Type 2 devices. Each respective Type 2 device chooses the Type 1 device from among all Type 1 devices as its signal source. Each Type 2 device may choose asynchronously (at different time). At least one time series of CI may be obtained by each respective Type 2 device from the respective series of probe signals from the Type 1 device, the CI being of the wireless multipath channel between the Type 2 device and the Type 1 device.

The respective Type 2 device chooses the Type 1 device from among all Type 1 devices as its signal source based on at least one of: identity (ID) of the Type 1 device and/or the respective Type 2 receiver, information of at least one of: a user, an account, access info, a parameter, a characteristics, and a signal strength associated with the Type 1 device and/or the respective Type 2 receiver, a task to be performed by the Type 1 device and/or the respective Type 2 receiver, whether the Type 1 device is the same as a past signal source, a history (of the past signal source, the Type 1 device, another Type 1 device, the respective Type 2 receiver, and another Type 2 receiver), and/or at least one threshold for switching signal source.

Initially, the Type 1 device may be the signal source of a set of initial respective Type 2 devices (i.e. the Type 1 device sends a respective wireless signal (series of probe signals) to the set of initial respective Type 2 devices) at an initial time. Each initial respective Type 2 device chooses the Type 1 device from among all Type 1 devices as its signal source.

The signal source (Type 1 device) of a particular Type 2 device may be changed when at least one of the following occurs: (1) a time interval between two adjacent probe signals (e.g. between the current probe signal and an immediate past probe signal, or between the next probe signal and the current probe signal) received from the current signal source of the particular Type 2 device exceeds a first threshold, (2) a signal strength associated with the current signal source of the Type 2 device is below a second threshold at the respective current time, (3) a processed signal strength associated with the current signal source of the Type 2 device is below a second threshold at the respective current time after the signal strength is processed with at least one of: a low pass filter, a band pass filter, a median filter, a moving average filter, a weighted averaging filter, a linear filter and a non-linear filter, and/or (4) the signal strength (or processed signal strength) associated with the current signal source of the Type 2 device is below a fourth threshold for a significant percentage of a recent time window (e.g. 70%, 80%, 90%, etc.). The percentage may exceed a fifth threshold. Any of first threshold, second threshold, third threshold, fourth threshold and fifth threshold may be time varying.

Condition (1) may occur when the Type 1 device and the Type 2 device become progressively far away from each other, such that some probe signal from the Type 1 device becomes too weak and is not received by the Type 2 device. Conditions (2)-(4) may occur when the two devices become far from each other such that the signal strength becomes very weak.

The signal source of the particular Type 2 device may not change if the other Type 1 devices have signal strength weaker than the current signal source (current selected Type 1 device). In another example, the signal source of the particular Type 2 device may also not change if the other Type 1 devices have signal strength weaker than a factor (e.g. 1.1, 1.2, or 1.5, etc.) of signal strength of the current signal source.

If the signal source is changed, the new signal source may take effect at a near future time (e.g. the respective next time). The new signal source may be the Type 1 device with strongest signal strength. The new signal source may also be the Type 1 device with strongest processed signal strength, wherein the signal strength of each Type 1 device may be processed with at least one of: a low pass filter, a band pass filter, a median filter, a moving average filter, a weighted averaging filter, a linear filter and a non-linear filter.

A list of available Type 1 devices may be initialized. The list may be updated by examining signal strength associated with the respective set of Type 1 devices. The list of available Type 1 devices may also be updated by examining processed signal strength associated with the respective set of Type 1 devices.

The respective chosen Type 1 device may/may not be different from the current signal source.

A Type 2 device may choose between the first series of probe signals and the second series of probe signals based on: respective pseudo-regular intervals, respective destination MAC addresses, respective channels, respective characteristics/properties/states, a respective task to be performed by the Type 2 device, signal strength of first series and second series, and/or another consideration.

The yet another wireless device and the another wireless device may be the same device. They may be in/on/of a common device. The Type 1 device may first establish the first wireless communication with the another wireless device, and then establish the second wireless communication with the yet another wireless device. The Type 1 device may start establishing the second wireless communication with the yet another wireless device before the first wireless communication is fully established. The Type 1 device may start establishing the second wireless communication with the yet another wireless device while the first wireless communication is being established.

The another wireless device may set its MAC address to a first destination MAC address and establish the first wireless connection with the Type 1 device using the first destination MAC address. The yet another wireless device may set its MAC address to a second destination MAC address and establish the second wireless connection with the Type 1 device using the second destination MAC address.

The transmitting may be using a processor, a memory and a set of instructions. Each of the Type 1 device and/or at least one Type 2 device may also have a heterogeneous IC. The heterogeneous IC may comprise the processor, memory and the set of instructions. The heterogeneous IC in different devices may be the same or different. Each Type 2 device may extract at least one time series of CI of the wireless multipath channel between the Type 1 device and the Type 2 device from the wireless signal. Each time series of CI is associated with an antenna of the Type 1 device and an antenna of the Type 2 device. The heterogeneous IC may generate the wireless signal, transmit or receive the wireless signal, extract the time series of CI from the wireless signal, and make the time series of CI available (e.g. to the processor/memory, other processors/memory).

Multiple Type 1 devices may transmit wireless signals asynchronously (e.g. to the same Type 2 device, to a number of Type 2 devices).

Multiple Type 2 devices may receive the wireless signal asynchronously. They may extract respective time series of CI from the wireless signal asynchronously, with respective heterogeneous starting time.

The wireless signal may be a series of probe signals. A probe signal may be transmitted with data. A probe signal may be replaced by a data signal.

The series of probe signals may be transmitted at a pseudo-regular interval (e.g. 100 probe signals per second). The pseudo-regular interval may be changed. The series of probe signals may be scheduled at a regular interval (e.g. 100 probe signals per second), but each probe signal may experience small time perturbation, perhaps due to timing requirement, timing control, network control, handshaking, message passing, collision avoidance, carrier sensing, congestion, availability of resources, and/or another consideration.

The series of probe signals may be transmitted at the pseudo-regular interval for a period of time. The pseudo-regular interval, the duration of the period of time and/or the starting time of the period of time, may be changed over time. For example, it may be 100 probe signals per second (probe/sec in short) for 2 hours and then changed to 1000 probe/sec for 30 minutes, and may change again.

The change may be according to a time table, a rule, a policy, a mode, a condition and/or a change (e.g. once every hour, or changed whenever a certain event occur). For example, the pseudo-regular interval may normally be 100 probe/sec, but will be changed to 1000 probe/sec in some demanding situations, and may be changed to 10 probe/sec in some low power and/or standby situation. The probe signals may be sent in burst also, e.g. at 100 probe/sec for 1 minute and no signal for some time before and after the burst. Or, the probe signal may be sent at 100 probe/sec and then momentarily at a burst rate of 1000 probe/sec for 1 minute and then back to 100 probe/sec. In another example, the probe signal may be sent at 1 probe/sec in a low power mode, at 10 probe/sec in a standby mode, at 100 probe/sec in a normal mode, and at 1000 probe/sec in an armed mode, etc.

The change based on at least one task performed by Type 1 device or Type 2 device. For example, the task of one receiver may need 10 probe/sec while the task of another receiver may need 1000 probe/sec. The pseudo-regular interval may be increased to 1000 probe/sec to satisfy the most demanding receiver. In one example, the receivers, the tasks associated with the receivers and/or the wireless multipath channel as experienced by the receivers may be divided into at least one class (e.g. a low priority class, a high priority class, an emergency class, a critical-task class, a regular class, a privileged class, a non-subscription class, a subscription class, a paying class, a non-paying class, etc.) and the pseudo-regular interval may be adjusted for the sake of some selected class (e.g. the high priority class). When the need of that selected class is less demanding, the pseudo-regular interval may be changed (increased or decreased). When a receiver has critically low power, the pseudo-regular interval may be reduced to reduce the power consumption of the receiver to respond to the probe signals.

In one example, the probe signals may be used to transfer power wirelessly to a receiver, and the pseudo-regular interval may be adjusted to control the amount of power being wirelessly transferred to the receiver.

The pseudo-regular interval may be changed by and/or based on a server, the Type 1 device and/or the Type 2 device. The server may be communicatively coupled with the Type 1 device and/or the Type 2 device. The change may be communicated between the server, the Type 1 device and/or the Type 2 device. For example, the server may monitor, track, forecast and/or anticipate the needs of the Type 2 device and/or the tasks performed by the receivers, and may decide to change the pseudo-regular interval accordingly. The server may send the change request to the Type 1 device (immediately or with some time delay) and the Type 1 device may then make the change. The server may keep track of a time table and may make scheduled changes to the pseudo-regular interval according to the time table. The server may detect an emergency situation of a receiver and change the pseudo-regular interval immediately. The server may detect a slowly happening condition (and/or an evolving condition) associated with a receiver and gradually adjust the pseudo-regular interval accordingly.

There may be more than one Type 1 devices. Each Type 1 device may transmit a respective wireless signal to more than one respective Type 2 devices through the wireless multipath channel in the venue. A CI time series may be obtained, each CI time series associated with a Type 1 device and a Type 2 device.

The characteristics and/or the spatial-temporal information of the motion of the object may be monitored individually based on a CI time series associated with a particular Type 1 device and a particular Type 2 device.

The characteristics and/or the spatial-temporal information of the motion of the object may be monitored jointly based on any CI time series associated with the particular Type 1 device and any Type 2 device.

The characteristics and/or the spatial-temporal information of the motion of the object may also be monitored jointly based on any CI time series associated with the particular Type 2 device and any Type 1 device.

The characteristics and/or the spatial-temporal information of the motion of the object may be monitored globally based on any CI time series associated with any Type 1 device and any Type 2 device.

Any joint monitoring (of the same motion or of the same object) may be associated with at least one of: a user, a user account, a profile, a household, a room, a location, and/or a user history, etc.

A first wireless multipath channel between a Type 1 device and a Type 2 device may be different from a second wireless multipath channel between another Type 1 device and another Type 2 device. The two wireless multipath channels may be associated with different frequency bands, different bandwidth, different carrier frequency, different modulation, different wireless standards, different coding, different encryption, different payload characteristics, different network parameters, etc.

The first wireless multipath channel and the second wireless multipath channel may be associated with different kinds of wireless system (e.g. two of the following: WiFi, LTE, LTE-A, 2.5G, 3G, 3.5G, 4G, beyond 4G, 5G, 6G, 7G, a 802.11 system, a 802.15 system, a 802.16 system, mesh network, Zigbee, WiMax, Bluetooth, BLE, RFID, UWB, microwave system, radar like system, etc.). For example, the first may be WiFi while the second may be LTE.

The first wireless multipath channel and the second wireless multipath channel may be associated with similar kinds of wireless system, but in different network. For example, the first wireless multipath channel may be associated with a WiFi network named "Pizza and Pizza" in the 2.4 GHz band with a bandwidth of 20 MHz while the second may be associated with a WiFi network called "StarBud hotspot" in the 5 GHz band with a bandwidth of 40 MHz.

The first wireless multipath channel may be associated with a particular wireless system (e.g. WiFi, or LTE, or 3G, or BLE, or mesh network, or adhoc network) while the second wireless multipath channel may be associated another wireless system of same kind as the first wireless multipath channel (e.g. both WiFi, or both LTE, or both 3G, etc.) with different network ID, SSID, characteristics, settings, and/or parameters. The first wireless multipath channel may also be a WiFi channel while the second wireless multipath channel may be another WiFi channel. For example, both first and second wireless multipath channels may be in the same WiFi network named "StarBud hotspot", using two different WiFi channels in "StarBud hotspot".

In one embodiment, a wireless monitoring system may comprise training at least one classifier of at least one known events in a venue based on training CI time series associated with the at least one events.

For each of the at least one known event happening in the venue in a respective training time period associated with the known event, a respective training wireless signal (e.g. a respective series of training probe signals) may be transmitted by an antenna of a first Type 1 heterogeneous wireless device using a processor, a memory and a set of instructions of the first Type 1 device to at least one first Type 2 heterogeneous wireless device through a wireless multipath channel in the venue in the respective training time period.

At least one respective time series of training CI (training CI time series) may be obtained asynchronously by each of the at least one first Type 2 device from the (respective) training wireless signal. The CI may be CI of the wireless multipath channel between the first Type 2 device and the first Type 1 device in the training time period associated with the known event. The at least one training CI time series may be preprocessed.

For a current event happening in the venue in a current time period, a current wireless signal (e.g. a series of current probe signals) may be transmitted by an antenna of a second Type 1 heterogeneous wireless device using a processor, a memory and a set of instructions of the second Type 1 device to at least one second Type 2 heterogeneous wireless device through the wireless multipath channel in the venue in the current time period associated with the current event.

At least one time series of current CI (current CI time series) may be obtained asynchronously by each of the at least one second Type 2 device from the current wireless signal (e.g. the series of current probe signals). The CI may be CI of the wireless multipath channel between the second Type 2 device and the second Type 1 device in the current time period associated with the current event. The at least one current CI time series may be preprocessed.

The at least one classifier may be applied to classify at least one current CI time series obtained from the series of current probe signals by the at least one second Type 2 device, to classify at least one portion of a particular current CI time series, and/or to classify a combination of the at least one portion of the particular current CI time series and another portion of another CI time series. The at least one classifier may also be applied to associate the current event with a known event, an unknown event and/or another event.

Each wireless signal (e.g. each series of probe signals) may comprise at least two CI each with an associated time stamp. Each CI may be associated with a respective time stamp.

A current CI time series associated with a second Type 2 device and another current CI time series associated with another second Type 2 device may have different starting time, different time duration, different stopping time, different count of items in the time series, different sampling frequency, different sampling period between two consecutive items in the time series, and/or CI (CI) with different features.

The first Type 1 device and the second Type 1 device may be the same device. The first Type 1 device and the second Type 1 device may be at same location in the venue.

The at least one first Type 2 device and the at least one second Type 2 device may be the same. The at least one first Type 2 device may be a permutation of the at least one second Type 2 device. A particular first Type 2 device and a particular second Type 2 device may be the same device.

The at least one first Type 2 device and/or a subset of the at least one first Type 2 device may be a subset of the at least one second Type 2 device. The at least one second Type 2 device and/or a subset of the at least one second Type 2 device may be a subset of the at least one first Type 2 device.

The at least one first Type 2 device and/or a subset of the at least one first Type 2 device may be a permutation of a subset of the at least one second Type 2 device. The at least one second Type 2 device and/or a subset of the at least one second Type 2 device may be a permutation of a subset of the at least one first Type 2 device.

The at least one second Type 2 device and/or a subset of the at least one second Type 2 device may be at same respective location as a subset of the at least one first Type 2 device. The at least one first Type 2 device and/or a subset of the at least one first Type 2 device may be at same respective location as a subset of the at least one second Type 2 device.

The antenna of the Type 1 device and the antenna of the second Type 1 device may be at same location in the venue. Antenna(s) of the at least one second Type 2 device and/or antenna(s) of a subset of the at least one second Type 2 device may be at same respective location as respective antenna(s) of a subset of the at least one first Type 2 device. Antenna(s) of the at least one first Type 2 device and/or antenna(s) of a subset of the at least one first Type 2 device may be at same respective location(s) as respective antenna(s) of a subset of the at least one second Type 2 device.

A first section of a first time duration of the first CI time series and a second section of a second time duration of the second section of the second CI time series may be aligned. A map between items of the first section and items of the second section may be computed.

The first section may comprise at least one of: a first segment of the first CI time series with a first starting time and/or a first ending time, and another segment of a processed first CI time series. The processed first CI time series may be the first CI time series processed by a first operation.

The second section may comprise at least one of: a second segment of the second CI time series with a second starting time and a second ending time, and another segment of a processed second CI time series. The processed second CI time series may be the second CI time series processed by a second operation.

The first operation and/or the second operation may comprise at least one of: subsampling, re-sampling, interpolation, filtering, transformation, feature extraction, pre-processing, and/or another operation.

A first item of the first section may be mapped to a second item of the second section. The first item of the first section may also be mapped to another item of the second section. Another item of the first section may also be mapped to the second item of the second section. The mapping may be one-to-one, one-to-many, many-to-one, many-to-many.

At least one function of at least one of: the first item of the first section of the first CI time series, another item of the first CI time series, a time stamp of the first item, a time difference of the first item, a time differential of the first item, a neighboring time stamp of the first item, another time stamp associated with the first item, the second item of the second section of the second CI time series, another item of the second CI time series, a time stamp of the second item, a time difference of the second item, a time differential of the second item, a neighboring time stamp of the second item, and another time stamp associated with the second item, may satisfy at least one constraint.

One constraint may be that a difference between the time stamp of the first item and the time stamp of the second item may be upper-bounded by an adaptive upper threshold and lower-bounded by an adaptive lower threshold.

The first section may be the entire first CI time series. The second section may be the entire second CI time series. The first time duration may be equal to the second time duration.

A section of a time duration of a CI time series may be determined adaptively. A tentative section of the CI time series may be computed. A starting time and an ending time of a section (e.g. the tentative section, the section) may be determined. The section may be determined by removing a beginning portion and an ending portion of the tentative section.

A beginning portion of a tentative section may be determined as follows. Iteratively, items of the tentative section with increasing time stamp may be considered as a current item, one item at a time.

In each iteration, at least one activity measure may be computed and/or considered. The at least one activity measure may be associated with at least one of: the current item associated with a current time stamp, past items of the tentative section with time stamps not larger than the current time stamp, and/or future items of the tentative section with time stamps not smaller than the current time stamp. The current item may be added to the beginning portion of the tentative section if at least one criterion associated with the at least one activity measure is satisfied.

The at least one criterion associated with the activity measure may comprise at least one of: (a) the activity measure is smaller than an adaptive upper threshold, (b) the activity measure is larger than an adaptive lower threshold, (c) the activity measure is smaller than an adaptive upper threshold consecutively for at least a predetermined amount of consecutive time stamps, (d) the activity measure is larger than an adaptive lower threshold consecutively for at least another predetermined amount of consecutive time stamps, (e) the activity measure is smaller than an adaptive upper threshold consecutively for at least a predetermined percentage of the predetermined amount of consecutive time stamps, (f) the activity measure is larger than an adaptive lower threshold consecutively for at least another predetermined percentage of the another predetermined amount of consecutive time stamps, (g) another activity measure associated with another time stamp associated with the current time stamp is smaller than another adaptive upper threshold and larger than another adaptive lower threshold, (h) at least one activity measure associated with at least one respective time stamp associated with the current time stamp is smaller than respective upper threshold and larger than respective lower threshold, (i) percentage of time stamps with associated activity measure smaller than respective upper threshold and larger than respective lower threshold in a set of time stamps associated with the current time stamp exceeds a threshold, and (j) another criterion.

An activity measure associated with an item at time T1 may comprise at least one of: (1) a first function of the item at time T1 and an item at time T1−D1, wherein D1 is a pre-determined positive quantity (e.g. a constant time offset), (2) a second function of the item at time T1 and an item at time T1+D1, (3) a third function of the item at time T1 and an item at time T2, wherein T2 is a pre-determined quantity (e.g. a fixed initial reference time; T2 may be changed over time; T2 may be updated periodically; T2 may be the beginning of a time period and T1 may be a sliding time in the time period), and (4) a fourth function of the item at time T1 and another item.

At least one of: the first function, the second function, the third function, and/or the fourth function may be a function (e.g. F(X, Y, . . . )) with at least two arguments: X and Y.

The two arguments may be scalars. The function (e.g. F) may be a function of at least one of: X, Y, (X−Y), (Y−X), abs(X−Y), X^a, Y^b, abs(X^a−Y^b), (X−Y)^a, (X/Y), (X+a)/(Y+b), (X^a/Y^b), and ((X/Y)^a−b), wherein a and b are may be some predetermined quantities. For example, the function may simply be abs(X−Y), or (X−Y)^2, (X−Y)^4. The function may be a robust function. For example, the function may be (X−Y)^2 when abs (X−Y) is less than a threshold T, and (X−Y)+a when abs(X−Y) is larger than T. Alternatively, the function may be a constant when abs(X−Y) is larger than T. The function may also be bounded by a slowly increasing function when abs(X−y) is larger than T, so that outliers cannot severely affect the result. Another example of the function may be (abs(X/Y)−a), where a=1. In this way, if X=Y (i.e. no change or no activity), the function will give a value of 0. If X is larger than Y, (X/Y) will be larger than 1 (assuming X and Y are positive) and the function will be positive. And if X is less than Y, (X/Y) will be smaller than 1 and the function will be negative.

In another example, both arguments X and Y may be n-tuples such that X=(x_1, x_2, . . . , x_n) and Y=(y_1, y_2, . . . , y_n). The function may be a function of at least one of: x_i, y_i, (x_i−y_i), (y_i−x_i), abs(x_i−y_i), x_i^a, y_i^b, abs(x_i^a−y_i^b), (x_i−y_i)^a, (x_i/y_i), (x_i+a)/(y_i+b), (x_i^a/y_i^b), and ((x_i/y_i)^a−b), wherein i is a component index of the n-tuple X and Y, and 1<=i<=n. E.g. component index of x_1 is i=1, component index of x_2 is i=2.

The function may comprise a component-by-component summation of another function of at least one of the following: x_i, y_i, (x_i−y_i), (y_i−x_i), abs(x_i−y_i), x_i^a, y_i^b, abs(x_i^a−y_i^b), (x_i−y_i)^a, (x_i/y_i), (x_i+a)/(y_i+b), (x_i^a/y_i^b), and ((x_i/y_i)^a−b), wherein i is the component index of the n-tuple X and Y. For example, the function may be in a form of sum_{i=1}^n (abs(x_i/y_i)−1)/n, or sum_{i=1}^n w_i*(abs(x_i/y_i)−1), where w_i is some weight for component i.

The map may be computed using dynamic time warping (DTW). The DTW may comprise a constraint on at least one of: the map, the items of the first CI time series, the items of the second CI time series, the first time duration, the second time duration, the first section, and/or the second section. Suppose in the map, the $i^{th}$ domain item is mapped to the $j^{th}$ range item. The constraint may be on admissible combination of i and j (constraint on relationship between i and j).

Mismatch cost between a first section of a first time duration of a first CI time series and a second section of a second time duration of a second CI time series may be computed.

The first section and the second section may be aligned such that a map comprising more than one links may be established between first items of the first CI time series and second items of the second CI time series. With each link, one of the first items with a first time stamp may be associated with one of the second items with a second time stamp.

A mismatch cost between the aligned first section and the aligned second section may be computed. The mismatch cost may comprise a function of: an item-wise cost between a first item and a second item associated by a particular link of the map, and a link-wise cost associated with the particular link of the map.

The aligned first section and the aligned second section may be represented respectively as a first vector and a second vector of same vector length. The mismatch cost may comprise at least one of: an inner product, an inner-product-like quantity, a quantity based on correlation, a quantity based on covariance, a discriminating score, a distance, a Euclidean distance, an absolute distance, an Lk distance (e.g. L1, L2, . . . ), a weighted distance, a distance-like quantity and/or another similarity value, between the first vector and the second vector. The mismatch cost may be normalized by the respective vector length.

A parameter derived from the mismatch cost between the first section of the first time duration of the first CI time series and the second section of the second time duration of the second CI time series may be modeled with a statistical distribution. At least one of: a scale parameter, a location parameter and/or another parameter, of the statistical distribution may be estimated.

The first section of the first time duration of the first CI time series may be a sliding section of the first CI time series. The second section of the second time duration of the second CI time series may be a sliding section of the second CI time series.

A first sliding window may be applied to the first CI time series and a corresponding second sliding window may be applied to the second CI time series. The first sliding window of the first CI time series and the corresponding second sliding window of the second CI time series may be aligned.

Mismatch cost between the aligned first sliding window of the first CI time series and the corresponding aligned second sliding window of the second CI time series may be computed. The current event may be associated with at least one of: the known event, the unknown event and/or the another event, based on the mismatch cost.

The classifier may be applied to at least one of: each first section of the first time duration of the first CI time series, and/or each second section of the second time duration of the second CI time series, to obtain at least one tentative classification results. Each tentative classification result may be associated with a respective first section and a respective second section.

The current event may be associated with at least one of: the known event, the unknown event and/or the another event, based on the mismatch cost.

The current event may be associated with at least one of: the known event, the unknown event and/or the another event, based on a largest number of tentative classification results in more than one sections of the first CI time series and corresponding more than sections of the second CI time series. For example, the current event may be associated with a particular known event if the mismatch cost points to the particular known event for N consecutive times (e.g. N=10). In another example, the current event may be associated with a particular known event if the percentage of mismatch cost within the immediate past N consecutive N pointing to the particular known event exceeds a certain threshold (e.g. >80%).

In another example, the current event may be associated with a known event that achieves smallest mismatch cost for the most times within a time period. The current event may be associated with a known event that achieves smallest overall mismatch cost, which is a weighted average of at least one mismatch cost associated with the at least one first sections. The current event may be associated with a particular known event that achieves smallest of another overall cost.

The current event may be associated with the "unknown event" if none of the known events achieve mismatch cost lower than a first threshold T1 in a sufficient percentage of the at least one first section. The current event may also be associated with the "unknown event" if none of the events achieve an overall mismatch cost lower than a second threshold T2.

The current event may be associated with at least one of: the known event, the unknown event and/or the another event, based on the mismatch cost and additional mismatch cost associated with at least one additional section of the first CI time series and at least one additional section of the second CI time series.

The known events may comprise at least one of: a door closed event, a door open event, a window closed event, a window open event, a multi-state event, an on-state event, an off-state event, an intermediate state event, a continuous state event, a discrete state event, a human-present event, a human-absent event, a sign-of-life-present event, and/or a sign-of-life-absent event.

A projection for each CI may be trained using a dimension reduction method based on the training CI time series. The dimension reduction method may comprise at least one of: principal component analysis (PCA), PCA with different kernel, independent component analysis (ICA), Fisher linear discriminant, vector quantization, supervised learning, unsupervised learning, self-organizing maps, auto-encoder, neural network, deep neural network, and/or another method. The projection may be applied to at least one of: the training CI time series associated with the at least one event, and/or the current CI time series, for the at least one classifier.

The at least one classifier of the at least one event may be trained based on the projection and the training CI time series associated with the at least one event. The at least one current CI time series may be classified based on the projection and the current CI time series.

The projection may be re-trained using at least one of: the dimension reduction method, and another dimension reduction method, based on at least one of: the training CI time series, at least one current CI time series before retraining the projection, and/or additional training CI time series.

The another dimension reduction method may comprise at least one of: principal component analysis (PCA), PCA with different kernels, independent component analysis (ICA), Fisher linear discriminant, vector quantization, supervised learning, unsupervised learning, self-organizing maps, auto-encoder, neural network, deep neural network, and/or yet another method, The at least one classifier of the at least one event may be re-trained based on at least one of: the re-trained projection, the training CI time series associated with the at least one events, and/or at least one current CI time series.

The at least one current CI time series may be classified based on: the re-trained projection, the re-trained classifier, and/or the current CI time series.

Each CI may comprise a vector of complex values. Each complex value may be preprocessed to give the magnitude of the complex value. Each CI may be preprocessed to give a vector of non-negative real numbers comprising the magnitude of corresponding complex values.

Each training CI time series may be weighted in the training of the projection.

The projection may comprise more than one projected components. The projection may comprise at least one most significant projected component. The projection may comprise at least one projected component that may be beneficial for the at least one classifier.

The channel information (CI) may be associated with/may comprise signal strength, signal amplitude, signal phase, received signal strength indicator (RSSI), channel state information (CSI), a channel impulse response (CIR), a channel frequency response (CFR). The CI may be associated with information associated with a frequency band, a frequency signature, a frequency phase, a frequency amplitude, a frequency trend, a frequency characteristics, a frequency-like characteristics, a time domain element, a frequency domain element, a time-frequency domain element, an orthogonal decomposition characteristics, and/or a non-orthogonal decomposition characteristics of the wireless signal through the wireless multipath channel.

The CI may also be associated with information associated with a time period, a time signature, a time stamp, a time amplitude, a time phase, a time trend, and/or a time characteristics of the wireless signal. The CI may be associated with information associated with a time-frequency partition, a time-frequency signature, a time-frequency amplitude, a time-frequency phase, a time-frequency trend, and/or a time-frequency characteristics of the wireless signal. The CI may be associated with a decomposition of the wireless signal. The CI may be associated with information associated with a direction, an angle of arrival (AoA), an angle of a directional antenna, and/or a phase of the wireless signal through the wireless multipath channel. The CI may be associated with attenuation patterns of the wireless signal through the wireless multipath channel Each CI may be associated with a Type 1 device and a Type 2 device. Each CI may be associated with an antenna of the Type 1 device and an antenna of the Type 2 device.

The channel information (CI) may be obtained from a communication hardware that is capable of providing the CI. The communication hardware may be a WiFi-capable chip/IC (integrated circuit), a chip compliant with a 802.11 or 802.16 or another wireless/radio standard, a next generation WiFi-capable chip, a LTE-capable chip, a 5G-capable chip, a 6G/7G/8G-capable chip, a Bluetooth-enabled chip, a BLE (Bluetooth low power)-enabled chip, a UWB chip, another communication chip (e.g. Zigbee, WiMax, mesh network), etc. The communication hardware computes the CI and stores the CI in a buffer memory and make the CI available for extraction. The CI may comprise data and/or at least one matrices related to channel state information (CSI). The at least one matrices may be used for channel equalization, and/or beam forming, etc.

The wireless multipath channel may be associated with a venue. The attenuation may be due to signal propagation in the venue, signal propagating/reflection/refraction/diffraction through/at/around air (e.g. air of venue), refraction medium/reflection surface such as wall, doors, furniture, obstacles and/or barriers, etc. The attenuation may be due to reflection at surfaces and obstacles (e.g. reflection surface, obstacle) such as floor, ceiling, furniture, fixtures, objects, people, pets, etc.

Each CI may be associated with a time stamp. Each CI may comprise N1 components (e.g. N1 frequency domain components in CFR, N1 time domain components in CIR, or N1 decomposition components). Each component may be associated with a component index. Each component may be a real quantity, an imaginary quantity, a complex quantity, a magnitude, a phase, a flag, and/or a set. Each CI may comprise a vector of complex numbers, a matrix of complex numbers, a set of mixed quantities, and/or a multi-dimensional collection of at least one complex numbers.

Components of a CI time series associated with a particular component index may form a respective component time series associated with the respective index. A CI time series may be divided into N1 component time series. Each respective component time series is associated with a respective component index. The characteristics/spatial-temporal information of the motion of the object may be monitored based on the component time series.

A component-wise characteristics of a component-feature time series of a CI time series may be computed. The component-wise characteristics may be a scalar (e.g. energy) or a function with a domain and a range (e.g. an autocorrelation function, a transform, an inverse transform). The characteristics/spatial-temporal information of the motion of the object may be monitored based on the component-wise characteristics.

A total characteristics of the CI time series may be computed based on the component-wise characteristics of each component time series of the CI time series. The total characteristics may be a weighted average of the component-wise characteristics. The characteristics/spatial-temporal information of the motion of the object may be monitored based on the total characteristics.

The Type 1 device and Type 2 device may support WiFi, WiMax, 3G/beyond 3G, 4G/beyond 4G, LTE, 5G, 6G, 7G, Bluetooth, BLE, Zigbee, a proprietary wireless system, and/or another wireless system.

A common wireless system and/or a common wireless channel may be shared by the Type 1 transceiver and/or the at least one Type 2 transceiver. The at least one Type 2 transceiver may transmit respective wireless signal contemporaneously using the common wireless system and/or the common wireless channel. The Type 1 transceiver may transmit a wireless signal to the at least one Type 2 transceiver using the common wireless system and/or the common wireless channel.

A Type 1 device may temporarily function as a Type 2 device, and vice versa.

Each Type 1 device and Type 2 device may have at least one transmitting/receiving antenna. Each CI may be associated with one of the transmitting antenna of the Type 1 device and one of the receiving antenna of the Type 2 device.

The at least one time series of CI may correspond to various antenna pairs between the Type 1 device and the Type 2 device. The Type 1 device may have at least one antenna. The Type 2 device may also have at least one antenna. Each time series of CI may be associated with an antenna of the Type 1 device and an antenna of the Type 2 device. Averaging or weighted averaging over antenna links may be performed. The averaging or weighted averaging may be over the at least one time series of CI. The averaging may optionally be performed on a subset of the at least one time series of CI corresponding to a subset of the antenna pairs.

Time stamps of CI of a portion of a time series of CI may be irregular and may be corrected so that corrected time-stamps of time-corrected CI may be uniformly spaced in time. In the case of multiple Type 1 devices and/or multiple Type 2 devices, the corrected time stamp may be with respect to the same or different clock.

An original timestamp associated with each of the CI may be determined. The original timestamp may not be uniformly spaced in time. Original timestamps of all CI of the particular portion of the particular time series of CI in the current sliding time window may be corrected so that corrected timestamps of time-corrected CI may be uniformly spaced in time.

The characteristics and/or spatial-temporal information may comprise: a location, a position (e.g. initial position, new position), a position on a map, a height, a horizontal location, a vertical location, a distance, a displacement, a speed, an acceleration, a rotational speed, a rotational acceleration, an angle of motion, direction of motion, rotation, a path, deformation, transformation, shrinking, expanding, a gait, a gait cycle, a head motion, a repeated motion, a periodic motion, a pseudo-periodic motion, an impulsive motion, a sudden motion, a fall-down motion, a transient motion, a behavior, a transient behavior, a period of motion, a frequency of motion, a time trend, a temporal profile, a temporal characteristics, an occurrence, a change, a change in frequency, a change in timing, a change of gait cycle, a timing, a starting time, an ending time, a duration, a history of motion, a motion type, a motion classification, a frequency, a frequency spectrum, a frequency characteristics, a presence, an absence, a proximity, an approaching, a receding, an identity of the object, a composition of the object, a head motion rate, a head motion direction, a mouth-related rate, an eye-related rate, a breathing rate, a heart rate, a hand motion rate, a hand motion direction, a leg motion, a body motion, a walking rate, a hand motion rate, a positional characteristics, a characteristics associated with movement of the object, a tool motion, a machine motion, a complex motion, and/or a combination of multiple motions, an event and/or another information. The processor shares computational workload with the Type 1 heterogeneous wireless device and Type 2 heterogeneous wireless device.

The Type 1 device and/or Type 2 device may be a local device. The local device may be: a smart phone, a smart device, TV, sound bar, set-top box, access point, router, repeater, remote control, speaker, fan, refrigerator, microwave, oven, coffee machine, hot water pot, utensil, table, chair, light, lamp, door lock, camera, microphone, motion sensor, security device, fire hydrant, garage door, switch, power adapter, computer, dongle, computer peripheral, electronic pad, sofa, tile, accessory, smart home device, smart vehicle device, smart office device, smart building device, smart manufacturing device, smart watch, smart glasses, smart clock, smart television, smart oven, smart refrigerator, smart air-conditioner, smart chair, smart table, smart accessory, smart utility, smart appliance, smart machine, smart vehicle, an internet-of-thing (IoT) device, an internet-enabled device, a computer, a portable computer, a tablet, a smart house, a smart office, a smart building, a smart parking lot, a smart system, and/or another device.

Each Type 1 device may be associated with a respective identify (ID). Each Type 2 device may also be associated with a respective identify (ID). The ID may comprise: a numeral, a combination of text and numbers, a name, a password, an account, an account ID, a web link, a web address, index to some information, and/or another ID. The ID may be assigned. The ID may be assigned by hardware (e.g. hardwired, via a dongle and/or other hardware), software and/or firmware. The ID may be stored (e.g. in a database, in memory, in a server, in the cloud, stored locally, stored remotely, stored permanently, stored temporarily) and may be retrieved. The ID may be associated with at least one record, account, user, household, address, phone number, social security number, customer number, another ID, time stamp, and/or collection of data. The ID and/or part of the ID of a Type 1 device may be made available to a Type 2 device. The ID may be used for registration, initialization, communication, identification, verification, detection, recognition, authentication, access control, cloud access, networking, social networking, logging, recording, cataloging, classification, tagging, association, pairing, transaction, electronic transaction, and/or intellectual property control, by the Type 1 device and/or the Type 2 device.

The object may be a person, passenger, child, older person, baby, sleeping baby, baby in a vehicle, patient, worker, high-value worker, expert, specialist, waiter, customer in a mall, traveler in airport/train station/bus terminal/shipping terminals, staff/worker/customer service personnel in a factory/mall/supermarket/office/workplace, serviceman in sewage/air ventilation system/lift well, lifts in lift wells, elevator, inmate, people to be tracked/monitored, animal, a plant, a living object, a pet, dog, cat, smart phone, phone accessory, computer, tablet, portable computer, dongle, computing accessory, networked devices, WiFi devices, IoT devices, smart watch, smart glasses, smart devices, speaker, keys, smart key, wallet, purse, handbag, backpack, goods, cargo, luggage, equipment, motor, machine, air conditioner, fan, air conditioning equipment, light fixture, moveable light, television, camera, audio and/or video equipment, stationary, surveillance equipment, parts, signage, tool, cart, ticket, parking ticket, toll ticket, airplane ticket, credit card, plastic card, access card, food packaging, utensil, table, chair, cleaning equipment/tool, vehicle, car, cars in parking facilities, merchandise in a warehouse/store/supermarket/distribution center, boat, bicycle, airplane, drone, remote control car/plane/boat, robot, manufacturing device, assembly line, material/unfinished part/robot/wagon/transports on a factory floor, object to be tracked in airport/shopping mart/supermarket, non-object, absence of an object, presence of an object, object with a form, object with a changing form, object with no form, mass of fluid, mass of liquid, mass of gas/smoke, fire, flame, electromagnetic (EM) source, EM medium, and/or another object.

The object itself may be communicatively coupled with some network, such as WiFi, MiFi, 3G/4G/LTE/5G, Bluetooth, BLE, WiMax, Zigbee, mesh network, adhoc network, and/or other network. The object itself may be bulky with AC power supply, but is moved during installation, cleaning, maintenance, renovation, etc. It may also be installed in a moveable platform such as a lift, a pad, a movable, platform, an elevator, a conveyor belt, a robot, a drone, a forklift, a car, a boat, a vehicle, etc.

The object may have multiple parts, each part with different movement. For example, the object may be a person walking forward. While walking, his left hand and right hand may move in different direction, with different instantaneous speed, acceleration, motion, etc.

The wireless transmitter (e.g. Type 1 device), the wireless receiver (e.g. Type 2 device), another wireless transmitter and/or another wireless receiver may move with the object and/or another object (e.g. in prior movement, current movement and/or future movement. They may be communicatively coupled to one or more nearby device. They may transmit time series of CI and/or information associated with the time series of CI to the nearby device, and/or each other. They may be with the nearby device.

The wireless transmitter and/or the wireless receiver may be part of a small (e.g. coin-size, cigarette box size, or even smaller), light-weight portable device. The portable device may be wirelessly coupled with a nearby device.

The nearby device may be smart phone, iPhone, Android phone, smart device, smart appliance, smart vehicle, smart gadget, smart TV, smart refrigerator, smart speaker, smart watch, smart glasses, smart pad, iPad, computer, wearable computer, notebook computer, gateway. The nearby device may be connected to a cloud server, a local server and/or other server via internet, wired internet connection and/or wireless internet connection. The nearby device may be portable.

The portable device, the nearby device, a local server and/or a cloud server may share the computation and/or storage for a task (e.g. obtain time series of CI, determine characteristics/spatial-temporal information of the object associated with the movement of the object, computation of time series of power information, determining/computing the particular function, searching for local extremum, classification, identifying particular value of time offset, denoising, processing, simplification, cleaning, wireless smart sensing task, extract CI from wireless signal, switching, segmentation, estimate trajectory, process the map, correction, corrective adjustment, adjustment, map-based correction, detecting error, checking for boundary hitting, thresholding, etc.) and information (e.g. time series of CI).

The nearby device may/may not move with the object. The nearby device may be portable/not portable/moveable/non-moveable. The nearby device may use battery power, solar power, AC power and/or other power source. The nearby device may have replaceable/non-replaceable battery, and/or rechargeable/non-rechargeable battery. The nearby device may be similar to the object. The nearby device may have identical (and/or similar) hardware and/or software to the object. The nearby device may be a smart device, a network enabled device, a device with connection to WiFi/3G/4G/5G/6G/Zigbee/Bluetooth/adhoc network/other network, a smart speaker, a smart watch, a smart clock, a smart appliance, a smart machine, a smart equipment, a smart tool, a smart vehicle, an internet-of-thing (IoT) device, an internet-enabled device, a computer, a portable computer, a tablet, and another device.

The nearby device and/or at least one processor associated with the wireless receiver, the wireless transmitter, the another wireless receiver, the another wireless transmitter and/or a cloud server (in the cloud) may determine the initial spatial-temporal information of the object. Two or more of them may determine the initial spatial-temporal info jointly. Two or more of them may share intermediate information in the determination of the initial spatial-temporal information (e.g. initial position).

In one example, the wireless transmitter (e.g. Type 1 device, or Tracker Bot) may move with the object. The wireless transmitter may send the wireless signal to the wireless receiver (e.g. Type 2 device, or Origin Register) or determining the initial spatial-temporal information (e.g. initial position) of the object. The wireless transmitter may also send the wireless signal and/or another wireless signal to another wireless receiver (e.g. another Type 2 device, or another Origin Register) for the monitoring of the motion (spatial-temporal info) of the object. The wireless receiver may also receive the wireless signal and/or another wireless signal from the wireless transmitter and/or the another wireless transmitter for monitoring the motion of the object. The location of the wireless receiver and/or the another wireless receiver may be known.

In another example, the wireless receiver (e.g. Type 2 device, or Tracker Bot) may move with the object. The wireless receiver may receive the wireless signal transmitted from the wireless transmitter (e.g. Type 1 device, or Origin Register) for determining the initial spatial-temporal info (e.g. initial position) of the object. The wireless receiver may also receive the wireless signal and/or another wireless signal from another wireless transmitter (e.g. another Type 1 device, or another Origin Register) for the monitoring of the current motion (e.g. spatial-temporal info) of the object. The wireless transmitter may also transmit the wireless signal and/or another wireless signal to the wireless receiver and/or the another wireless receiver (e.g. another Type 2 device, or another Tracker Bot) for monitoring the motion of the object. The location of the wireless transmitter and/or the another wireless transmitter may be known.

The venue may be a space such as a room, a house, an office, a workplace, a hallway, a walkway, a lift, a lift well, an escalator, an elevator, a sewage system, air ventilations system, a staircase, a gathering area, a duct, an air duct, a pipe, a tube, an enclosed structure, a semi-enclosed structure, an enclosed area, an area with at least one wall, a plant, a machine, an engine, a structure with wood, a structure with glass, a structure with metal, a structure with walls, a structure with doors, a structure with gaps, a structure with reflection surface, a structure with fluid, a building, a roof top, a store, a factory, an assembly line, a hotel room, a museum, a classroom, a school, a university, a government building, a warehouse, a garage, a mall, an airport, a train station, a bus terminal, a hub, a transportation hub, a shipping terminal, a government facility, a public facility, a school, a university, an entertainment facility, a recreational facility, a hospital, a seniors home, an elderly care facility, a community center, a stadium, a playground, a park, a field, a sports facility, a swimming facility, a track and/or field, a basketball court, a tennis court, a soccer stadium, a baseball stadium, a gymnasium, a hall, a garage, a shopping mart, a mall, a supermarket, a manufacturing facility, a parking facility, a construction site, a mining facility, a transportation facility, a highway, a road, a valley, a forest, a wood, a terrain, a landscape, a den, a patio, a land, a path, an amusement park, an urban area, a rural area, a suburban area, a metropolitan area, a garden, a square, a plaza, a music hall, a downtown facility, an over-air facility, a semi-open facility, a closed area, a train platform, a train station, a distribution center, a warehouse, a store, a distribution center, a storage facility, an underground facility, a space (e.g. above ground, outer-space) facility, a floating facility, a cavern, a tunnel facility, an indoor facility, an open-air facility, an outdoor facility with some walls/doors/reflective barriers, an open facility, a semi-open facility, a car, a truck, a bus, a van, a container, a ship/boat, a submersible, a train, a tram, an airplane, a vehicle, a mobile home, a cave, a tunnel, a pipe, a channel, a metropolitan area, downtown area with relatively tall buildings, a valley, a well, a duct, a pathway, a gas line, an oil line, a water pipe, a network of interconnecting pathways/alleys/roads/tubes/cavities/caves/pipe-like structure/air space/fluid space, a human body, an animal body, a body cavity, an organ, a bone, a teeth, a soft tissue, a hard tissue, a rigid tissue, a non-rigid tissue, a blood/body fluid vessel, windpipe, air duct, a den, etc. The venue may be an indoor space, an outdoor space, The venue may include both the inside and outside of the space. For example, the venue may include both the inside of a building and the outside of the building. For example, the venue can be a building that has one floor or multiple floors, and a portion of the building can be underground. The shape of the building can be, e.g., round, square, rectangular, triangle, or irregular-shaped. These are merely examples. The disclosure can be used to detect events in other types of venue or spaces.

The wireless transmitter (e.g. Type 1 device) and/or the wireless receiver (e.g. Type 2 device) may be embedded in a portable device (e.g. a module, or a device with the module) that may move with the object (e.g. in prior movement and/or current movement). The portable device may be communicatively coupled with the object using a wired connection (e.g. through USB, microUSB, Firewire, HDMI, serial port, parallel port, and other connectors) and/or a wireless connection (e.g. Bluetooth, Bluetooth Low Energy (BLE), WiFi, LTE, ZigBee, etc.). The portable device may be a lightweight device. The portable may be powered by battery, rechargeable battery and/or AC power. The portable device may be very small (e.g. at sub-millimeter scale and/or sub-centimeter scale), and/or small (e.g. coin-size, card-size, pocket-size, or larger). The portable device may be large, sizable, and/or bulky (e.g. heavy machinery to be installed). The portable device may be a WiFi hotspot, an access point, a mobile WiFi (MiFi), a dongle with USB/micro USB/Firew1ire/other connector, a smartphone, a portable computer, a computer, a tablet, a smart device, an internet-of-thing (IoT) device, a WiFi-enabled device, an LTE-enabled device, a smart watch, a smart glass, a smart mirror, a smart antenna, a smart battery, a smart light, a smart pen, a smart ring, a smart door, a smart window, a smart clock, a small battery, a smart wallet, a smart belt, a smart handbag, a smart clothing/garment, a smart ornament, a smart packaging, a smart paper/book/magazine/poster/printed matter/signage/display/lighted system/lighting system, a smart key/tool, a smart bracelet/chain/necklace/wearable/accessory, a smart pad/cushion, a smart tile/block/brick/building material/other material, a smart garbage can/waste container, a smart food carriage/storage, a smart ball/racket, a smart chair/sofa/bed, a smart shoe/footwear/carpet/mat/shoe rack, a smart glove/hand wear/ring/hand ware, a smart hat/headwear/makeup/sticker/tattoo, a smart mirror, a smart toy, a smart pill, a smart utensil, a smart bottle/food container, a smart tool, a smart device, an IoT device, a WiFi enabled device, a network enabled device, a 3G/4G/5G/6G enabled device, an embeddable device, an implantable device, air conditioner, refrigerator, heater, furnace, furniture, oven, cooking device, television/set-top box (STB)/DVD player/audio player/video player/remote control, hi-fi, audio device, speaker, lamp/light, wall, door, window, roof, roof tile/shingle/structure/attic structure/device/feature/installation/fixtures, lawn mower/garden tools/yard tools/mechanics tools/garage tools/, garbage can/container, 20-ft/40-ft container, storage container, factory/manufacturing/production device, repair tools, fluid container, machine, machinery to be installed, a vehicle, a cart, a wagon, warehouse vehicle, a car, a bicycle, a motorcycle, a boat, a vessel, an airplane, a basket/box/bag/bucket/container, a smart plate/cup/bowl/pot/mat/utensils/kitchen tools/kitchen devices/kitchen accessories/cabinets/tables/chairs/tiles/lights/water pipes/taps/gas range/oven/dishwashing machine/etc. The portable device may have a battery that may be replaceable, irreplaceable, rechargeable, and/or non-rechargeable. The portable device may be wirelessly charged. The portable device may be a smart payment card. The portable device may be a payment card used in parking lots, highways, entertainment parks, or other venues/facilities that need payment. The portable device may have an identity (ID) as described above.

An event may be monitored based on the time series of CI. The event may be an object related event, such as fall-down of the object (e.g. an person and/or a sick person), a rotation, a hesitation, a pause, an impact (e.g. a person hitting a sandbag, a door, a window, a bed, a chair, a table, a desk, a cabinet, a box, another person, an animal, a bird, a fly, a table, a chair, a ball, a bowling ball, a tennis ball, a football, a soccer ball, a baseball, a basketball, a volley ball, etc.), a two-body action (e.g. a person letting go a balloon, catching a fish, molding a clay, writing a paper, a person typing on a computer, etc.), a car moving in a garage, a person carrying a smart phone and walking around an airport/mall/government building/office/etc, an autonomous moveable object/machine moving around (e.g. vacuum cleaner, utility vehicle, a car, drone, self-driving car, etc.).

The task or the wireless smart sensing task may comprise: object detection, presence detection, object recognition, object verification, tool detection, tool recognition, tool verification, machine detection, machine recognition, machine verification, human detection, human recognition, human verification, baby detection, baby recognition, baby verification, human breathing detection, motion detection, motion estimation, motion verification, periodic motion detection, periodic motion estimation, periodic motion verification, stationary motion detection, stationary motion estimation, stationary motion verification, cyclo-stationary motion detection, cyclo-stationary motion estimation, cyclo-stationary motion verification, transient motion detection, transient motion estimation, transient motion verification, trend detection, trend estimation, trend verification, breathing detection, breathing estimation, breathing estimation, human biometrics detection, human biometrics estimation, human biometrics verification, environment informatics detection, environment informatics estimation, environment informatics verification, gait detection, gait estimation, gait verification, gesture detection, gesture estimation, gesture verification, machine learning, supervised learning, unsupervised learning, semi-supervised learning, clustering, feature extraction, featuring training, principal component analysis, eigen-decomposition, frequency decomposition, time decomposition, time-frequency decomposition, functional decomposition, other decomposition, training, discriminative training, supervised training, unsupervised training, semi-supervised training, neural network, sudden motion detection, fall-down detection, danger detection, life-threat detection, regular motion detection, stationary motion detection, cyclo-stationary motion detection, intrusion detection, suspicious motion detection, security, safety monitoring, navigation, guidance, map-based processing, map-based correction, irregularity detection, locationing, tracking, multiple object tracking, indoor tracking, indoor position, indoor navigation, power transfer, wireless power transfer, object counting, car tracking in parking garage, patient detection, patient monitoring, patient verification, wireless communication, data communication, signal broadcasting, networking, coordination, administration, encryption, protection, cloud computing, other processing and/or other task. The task may be performed by the Type 1 device, the Type 2 device, another Type 1 device, another Type 2 device, a nearby device, a local server, an edge server, a cloud server, and/or another device.

A first part of the task may comprise at least one of: preprocessing, signal conditioning, signal processing, postprocessing, denoising, feature extraction, coding, encryption, transformation, mapping, motion detection, motion estimation, motion change detection, motion pattern detection, motion pattern estimation, motion pattern recognition, vital sign detection, vital sign estimation, vital sign recognition, periodic motion detection, periodic motion estimation, breathing rate detection, breathing rate estimation, breathing pattern detection, breathing pattern estimation, breathing pattern recognition, heart beat detection, heart beat estimation, heart pattern detection, heart pattern estimation, heart pattern recognition, gesture detection, gesture estimation, gesture recognition, speed detection, speed estimation, object locationing, object tracking, navigation, acceleration estimation, acceleration detection, fall-down detection, change detection, intruder detection, baby detection, baby monitoring, patient monitoring, object recognition, wireless power transfer, and/or wireless charging.

A second part of the task may comprise at least one of: a smart home task, a smart office task, a smart building task, a smart factory task (e.g. manufacturing using a machine or an assembly line), a smart internet-of-thing (IoT) task, a smart system task, a smart home operation, a smart office operation, a smart building operation, a smart manufacturing operation (e.g. moving supplies/parts/raw material to a machine/an assembly line), an IoT operation, a smart system operation, turning on a light, turning off the light, controlling the light in at least one of: a room, a region, and/or the venue, playing a sound clip, playing the sound clip in at least one of: the room, the region, and/or the venue, playing the sound clip of at least one of: a welcome, a greeting, a farewell, a first message, and/or a second message associated with the first part of the task, turning on an appliance, turning off the appliance, controlling the appliance in at least one of: the room, the region, and/or the venue, turning on an electrical system, turning off the electrical system, controlling the electrical system in at least one of: the room, the region, and/or the venue, turning on a security system, turning off the security system, controlling the security system in at least one of: the room, the region, and/or the venue, turning on a mechanical system, turning off a mechanical system, controlling the mechanical system in at least one of: the room, the region, and/or the venue, and/or controlling at least one of: an air conditioning system, a heating system, a ventilation system, a lighting system, a heating device, a stove, an entertainment system, a door, a fence, a window, a garage, a computer system, a networked device, a networked system, a home appliance, an office equipment, a lighting device, a robot (e.g. robotic arm), a smart vehicle, a smart machine, an assembly line, a smart device, an internet-of-thing (IoT) device, a smart home device, and/or a smart office device.

The task may include: detect a user returning home, detect a user leaving home, detect a user moving from one room to another, detect/control/lock/unlock/open/close/partially open a window/door/garage door/blind/curtain/panel/solar panel/sun shade, detect a pet, detect/monitor a user doing something (e.g. sleeping on sofa, sleeping in bedroom, running on treadmill, cooking, sitting on sofa, watching TV, eating in kitchen, eating in dining room, going upstairs/ downstairs, going outside/coming back, in the rest room, etc.), monitor/detect location of a user/pet, do something automatically upon detection, do something for the user automatically upon detecting the user, turn on/off/dim a light, turn on/off music/radio/home entertainment system, turn on/off/adjust/control TV/HiFi/set-top-box (STB)/home entertainment system/smart speaker/smart device, turn on/off/adjust air conditioning system, turn on/off/adjust ventilation system, turn on/off/adjust heating system, adjust/ control curtains/light shades, turn on/off/wake a computer, turn on/off/pre-heat/control coffee machine/hot water pot, turn on/off/control/preheat cooker/oven/microwave oven/ another cooking device, check/adjust temperature, check weather forecast, check telephone message box, check mail, do a system check, control/adjust a system, check/control/ arm/disarm security system/baby monitor, check/control refrigerator, give a report (e.g. through a speaker such as Google home, Amazon Echo, on a display/screen, via a webpage/email/messaging system/notification system, etc.).

For example, when a user arrives home in his car, the task may be to, automatically, detect the user or his car approaching, open the garage door upon detection, turn on the driveway/garage light as the user approaches the garage, turn on air conditioner/heater/fan, etc. As the user enters the house, the task may be to, automatically, turn on the entrance light, turn off driveway/garage light, play a greeting message to welcome the user, turn on the music, turn on the radio and tuning to the user's favorite radio news channel, open the curtain/blind, monitor the user's mood, adjust the lighting and sound environment according to the user's mood or the current/imminent event (e.g. do romantic lighting and music because the user is scheduled to eat dinner with girlfriend in 1 hour) on the user's daily calendar, warm the food in microwave that the user prepared in the morning, do a diagnostic check of all systems in the house, check weather forecast for tomorrow's work, check news of interest to the user, check user's calendar and to-do list and play reminder, check telephone answer system/messaging system/email and give a verbal report using dialog system/speech synthesis, remind (e.g. using audible tool such as speakers/HiFi/ speech synthesis/sound/voice/music/song/sound field/background sound field/dialog system, using visual tool such as TV/entertainment system/computer/notebook/smart pad/ display/light/color/brightness/patterns/symbols, using haptic tool/virtual reality tool/gesture/tool, using a smart device/ appliance/material/furniture/fixture, using web tool/server/ cloud server/fog server/edge server/home network/mesh network, using messaging tool/notification tool/communication tool/scheduling tool/email, using user interface/GUI, using scent/smell/fragrance/taste, using neural tool/nervous system tool, using a combination, etc.) the user of his mother's birthday and to call her, prepare a report, and give the report (e.g. using a tool for reminding as discussed above). The task may turn on the air conditioner/heater/ ventilation system in advance, or adjust temperature setting of smart thermostat in advance, etc. As the user moves from the entrance to the living room, the task may be to turn on the living room light, open the living room curtain, open the window, turn off the entrance light behind the user, turn on the TV and set-top box, set TV to the user's favorite channel, adjust an appliance according to the user's preference and conditions/states (e.g. adjust lighting and choose/play music to build a romantic atmosphere), etc.

Another example may be: When the user wakes up in the morning, the task may be to detect the user moving around in the bedroom, open the blind/curtain, open the window, turn off the alarm clock, adjust indoor temperature from night-time temperature profile to day-time temperature profile, turn on the bedroom light, turn on the restroom light as the user approaches the restroom, check radio or streaming channel and play morning news, turn on the coffee machine and preheat the water, turn off security system, etc. When the user walks from bedroom to kitchen, the task may be to turn on the kitchen and hallway lights, turn off the bedroom and restroom lights, move the music/message/reminder from the bedroom to the kitchen, turn on the kitchen TV, change TV to morning news channel, lower the kitchen blind and open the kitchen window to bring in fresh air, unlock backdoor for the user to check the backyard, adjust temperature setting for the kitchen, etc.

Another example may be: When the user leaves home for work, the task may be to detect the user leaving, play a farewell and/or have-a-good-day message, open/close garage door, turn on/off garage light and driveway light, turn off/dim lights to save energy (just in case the user forgets), close/lock all windows/doors (just in case the user forgets), turn off appliance (especially stove, oven, microwave oven), turn on/arm the home security system to guard the home against any intruder, adjust air conditioning/heating/ventilation systems to "away-from-home" profile to save energy, send alerts/reports/updates to the user's smart phone, etc.

A motion may comprise at least one of: a no-motion, a resting motion, a non-moving motion, a deterministic motion, a transient motion, a fall-down motion, a repeating motion, a periodic motion, a pseudo-periodic motion, a periodic motion associated with breathing, a periodic motion associated with heartbeat, a periodic motion associated with a living object, a periodic motion associated with a machine, a periodic motion associated with a man-made object, a periodic motion associated with nature, a complex motion with a transient element and a periodic element, a repetitive motion, a non-deterministic motion, a probabilistic motion, a chaotic motion, a random motion, a complex motion with a non-deterministic element and a deterministic element, a stationary random motion, a pseudo-stationary random motion, a cyclo-stationary random motion, a non-stationary random motion, a stationary random motion with a periodic autocorrelation function (ACF), a random motion with a periodic ACF for a period of time, a random motion that is pseudo-stationary for a period of time, a random motion of which an instantaneous ACF has a pseudo-periodic element for a period of time, a machine motion, a mechanical motion, a vehicle motion, a drone motion, an air-related motion, a wind-related motion, a weather-related motion, a water-related motion, a fluid-related motion, an ground-related motion, a change in electro-magnetic characteristics, a sub-surface motion, a seismic motion, a plant motion, an animal motion, a human motion, a normal motion, an abnormal motion, a dangerous motion, a warning motion, a suspicious motion, a rain, a fire, a flood, a tsunami, an explosion, a collision, an imminent collision, a human body motion, a head motion, a facial motion, an eye motion, a mouth motion, a tongue motion, a neck motion, a finger motion, a hand motion, an arm motion, a shoulder motion, a body motion, a chest motion, an abdominal motion, a hip motion, a leg motion, a foot motion, a body joint motion, a knee motion, an elbow motion, an upper body motion, a lower body motion, a skin motion, a below-skin motion, a subcutaneous tissue motion, a blood vessel motion, an intravenous motion, an organ motion, a heart motion, a lung motion, a stomach motion, an intestine motion, a bowel motion, an eating motion, a breathing motion, a facial expression, an eye expression, a mouth expression, a talking motion, a singing motion, an eating motion, a gesture, a hand gesture, an arm gesture, a keystroke, a typing stroke, a user-interface gesture, a man-machine interaction, a gait, a dancing movement, a coordinated movement, and/or a coordinated body movement.

The heterogeneous IC of the Type 1 device and/or any Type 2 receiver may comprise a low-noise amplifier (LNA), a power amplifier, a transmit-receive switch, a media access controller, a baseband radio, a 2.4 GHz radio, a 3.65 GHz radio, a 4.9 GHz radio, a 5 GHz radio, a 5.9 GHz radio, a below 6 GHz radio, a below 60 GHz radio and/or another radio.

The heterogeneous IC may comprise a processor, a memory communicatively coupled with the processor, and a set of instructions stored in the memory to be executed by the processor. The IC may be an application specific integrated circuit (ASIC), a field programmable gate array (FPGA), other programmable logic device, discrete logic, and/or a combination.

The heterogeneous IC may support a broadband network, a wireless network, a mobile network, a mesh network, a cellular network, a wireless local area network (WLAN), a wide area network (WAN), and a metropolitan area network (MAN), a WLAN standard, WiFi, LTE, a 802.11 standard, 802.11a, 802.11b, 802.11g, 802.11n, 802.11ac, 802.11ad, 802.11af, 802.11ah, 802.11ax, 802.11ay, a mesh network standard, a 802.15 standard, a 802.16 standard, a cellular network standard, 3G, 3.5G, 4G, beyond 4G, 4.5G, 5G, 6G, 7G, 8G, 9G, Bluetooth, Bluetooth Low-Energy (BLE), Zigbee, WiMax, and/or another wireless network protocol.

The processor may comprise a general purpose processor, a special purpose processor, a microprocessor, a microcontroller, an embedded processor, a digital signal processor, a central processing unit (CPU), a graphical processing unit (GPU), a multi-processor, a multi-core processor, and/or a processor with graphics capability, and/or a combination.

The memory may be volatile, non-volatile, random access memory (RAM), Read Only Memory (ROM), Electrically Programmable ROM (EPROM), Electrically Erasable Programmable ROM (EEPROM), hard disk, flash memory, CD-ROM, DVD-ROM, a magnetic storage, an optical storage, an organic storage, a storage system, a storage network, network storage, cloud storage, or other form of non-transitory storage medium known in the art.

The set of instructions (machine executable code) corresponding to the method steps may be embodied directly in hardware, in software, in firmware, or in combinations thereof.

The presentation may be a presentation in an audio-visual way, a graphical way (e.g. using GUI), a textual way, a symbolic way or a mechanical way.

Computational workload associated with the method is shared among the processor, the Type 1 heterogeneous wireless device, the Type 2 heterogeneous wireless device, a local server, a cloud server, and another processor.

An operation, a pre-processing, a processing and/or a postprocessing may be applied to data (e.g. time series of CI, autocorrelation). An operation may be preprocessing, processing and/or postprocessing. The preprocessing, processing and/or postprocessing may be an operation. An operation may comprise preprocessing, processing, post-processing, computing a function of the operands, filtering, linear filtering, nonlinear filtering, folding, grouping, energy computation, lowpass filtering, bandpass filtering, highpass filtering, median filtering, rank filtering, quartile filtering, percentile filtering, mode filtering, finite impulse response (FIR) filtering, infinite impulse response (IIR) filtering, moving average (MA) filtering, autoregressive (AR) filtering, autoregressive moving averaging (ARMA) filtering, selective filtering, adaptive filtering, interpolation, decimation, subsampling, upsampling, resampling, time correction, time base correction, phase correction, magnitude correction, phase cleaning, magnitude cleaning, matched filtering, enhancement, restoration, denoising, smoothing, signal conditioning, enhancement, restoration, spectral analysis, linear transform, nonlinear transform, frequency transform, inverse frequency transform, Fourier transform, wavelet transform, Laplace transform, Hilbert transform, Hadamard transform, trigonometric transform, sine transform, cosine transform, power-of-2 transform, sparse transform, graph-based transform, graph signal processing, fast transform, a transform combined with zero padding, cyclic padding, padding, zero padding, feature extraction, decomposition, projection, orthogonal projection, non-orthogonal projection, over-complete projection, eigen-decomposition, singular value decomposition (SVD), principle component analysis (PCA), independent component analysis (ICA), grouping, sorting, thresholding, soft thresholding, hard thresholding, clipping, soft clipping, first derivative, second order derivative, high order derivative, convolution, multiplication, division, addition, subtraction, integration, maximization, minimization, local maximization, local minimization, optimization of a cost function, neural network, recognition, labeling, training, clustering, machine learning, supervised learning, unsupervised learning, semi-supervised learning, comparison with another time series of CI, similarity score computation, quantization, vector quantization, matching pursuit, compression, encryption, coding, storing, transmitting, normalization, temporal normalization, frequency domain normalization, classification, clustering, labeling, tagging, learning, detection, estimation, learning network, mapping, remapping, expansion, storing, retrieving, transmitting, receiving, representing, merging, combining, splitting, tracking, monitoring, matched filtering, Kalman filtering, particle filter, intrapolation, extrapolation, importance sampling, Monte Carlo sampling, compressive sensing, representing, merging, combining, splitting, scrambling, error protection, forward error correction, doing nothing, time varying processing, conditioning averaging, weighted averaging, arithmetic mean, geometric mean, averaging over selected frequency, averaging over antenna links, a logical operation, permutation, combination, sorting, AND, OR, XOR, union, intersection, vector addition, vector subtraction, vector multiplication, vector division, inverse, a norm, a distance, and/or another operation. The operation may be the preprocessing, processing, and/or post-processing. Operations may be applied jointly on multiple time series or functions.

The function (e.g. function of the operands) may comprise: a scalar function, a vector function, a discrete function, a continuous function, a polynomial function, a magnitude, a phase, an exponential function, a logarithmic function, a trigonometric function, a transcendental function, a logical function, a linear function, an algebraic function, a nonlinear function, a piecewise linear function, a real function, a complex function, a vector-valued function, an inverse function, a derivative of a function, an integration of a function, a circular function, a function of another function, a one-to-one function, a one-to-many function, a many-to-one function, a many-to-many function, a zero crossing, absolute function, indicator function, a mean, a mode, a median, a range, a statistics, a variance, a trimmed mean, a percentile, a square, a cube, a root, a power, a sine, a cosine, a tangent, a cotangent, a secant, a cosecant, an elliptical function, a parabolic function, a hyperbolic function, a game function, a zeta function, an absolute value, a thresholding, a quantization, a piecewise constant function, a composite function, a function of function, an input time function processed with an operation (e.g. filtering), a probabilistic function, a stochastic function, a random function, an ergodic function, a stationary function, a deterministic function, a transformation, a frequency transform, an inverse frequency transform, a discrete time transform, Laplace transform, Hilbert transform, sine transform, cosine transform, triangular transform, wavelet transform, integer transform, power-of-2 transform, sparse transform, projection, decomposition, principle component analysis (PCA), independent component analysis (ICA), neural network, feature extraction, a moving function, a function of a moving window of neighboring items of a time series, a filtering function, a convolution, a mean function, a variance function, a statistical function, short-time transform, discrete transform, discrete Fourier transform, discrete cosine transform, discrete sine transform, Hadamard transform, eigendecomposition, eigenvalue, singular value decomposition (SVD), singular value, orthogonal decomposition, matching pursuit, sparse transform, sparse approximation, any decomposition, graph-based processing, graph-based transform, graph signal processing, classification, labeling, learning, machine learning, detection, estimation, feature extraction, learning network, feature extraction, denoising, signal enhancement, coding, encryption, mapping, remapping, vector quantization, lowpass filtering, highpass filtering, bandpass filtering, matched filtering, Kalman filtering, preprocessing, postprocessing, particle filter, FIR filtering, IIR filtering, autoregressive (AR) filtering, adaptive filtering, first order derivative, high order derivative, integration, zero crossing, smoothing, median filtering, mode filtering, sampling, random sampling, resampling function, downsampling, upsampling, interpolation, extrapolation, importance sampling, Monte Carlo sampling, compressive sensing, statistics, short term statistics, long term statistics, mean, variance, autocorrelation function, cross correlation, moment generating function, time averaging, etc.

Machine learn, training, discriminative training, deep learning, neural network, continuous time processing, distributed computing, distributed storage, acceleration using GPU/DSP/coprocessor/multicore/multiprocessing may be applied to a step (or each step) of this disclosure.

A frequency transform may include Fourier transform, Laplace transform, Hadamard transform, Hilbert transform, sine transform, cosine transform, triangular transform, wavelet transform, integer transform, power-of-2 transform, combined zero padding and transform, Fourier transform with zero padding, and/or another transform. Fast versions and/or approximated versions of the transform may be performed. The transform may be performed using floating point, and/or fixed point arithmetic.

An inverse frequency transform may include inverse Fourier transform, inverse Laplace transform, inverse Hadamard transform, inverse Hilbert transform, inverse sine transform, inverse cosine transform, inverse triangular transform, inverse wavelet transform, inverse integer transform, inverse power-of-2 transform, combined zero padding and transform, inverse Fourier transform with zero padding, and/or another transform. Fast versions and/or approximated versions of the transform may be performed. The transform may be performed using floating point, and/or fixed point arithmetic.

Sliding time window may have time varying window width. It may be smaller at the beginning to enable fast acquisition and may increase over time to a steady-state size. The steady-state size may be related to the frequency, repeated motion, transient motion, and/or spatial-temporal information to be monitored. Even in steady state, the window size may be adaptively changed based on battery life, power consumption, available computing power, a change in amount of targets, the nature of motion to be monitored, etc.

The time shift between two sliding time windows at adjacent time instance may be constant/variable/locally adaptive over time. When shorter time shift is used, the update of any monitoring may be more frequent which may be used for fast changing situations, object motions, and/or objects. Longer time shift may be used for slower situations, object motions, and/or objects.

The window width/size and/or time shift may be changed upon a user request/choice. The time shift may be changed automatically (e.g. as controlled by processor/computer/server/cloud server) and/or adaptively.

At least one characteristics of a function (e.g. auto-correlation function, auto-covariance function, cross-correlation function, cross-covariance function, power spectral density, a time function, a frequency domain function, a frequency transform) may be determined (e.g. by an object tracking server, the processor, the Type 1 heterogeneous device, the Type 2 heterogeneous device, and/or another device). The at least one characteristics of the function may include: a local maximum, a local minimum, a local extremum, a local extremum with positive time offset, a first local extremum with positive time offset, an n^th local extremum with positive time offset, a local extremum with negative time offset, a first local extremum with negative time offset, an n^th local extremum with negative time offset, a constrained (with argument within a constraint) maximum, minimum, constrained maximum, constrained minimum, a constrained extremum, a slope, a derivative, a higher order derivative, a maximum slope, a minimum slope, a local maximum slope, a local maximum slope with positive time offset, a local minimum slope, a constrained maximum slope, a constrained minimum slope, a maximum higher order derivative, a minimum higher order derivative, a constrained higher order derivative, a zero-crossing, a zero crossing with positive time offset, an n^th zero crossing with positive time offset, a zero crossing with negative time offset, an n^th zero crossing with negative time offset, a constrained zero-crossing, a zero-crossing of slope, a zero-crossing of higher order derivative, and/or another characteristics. At least one argument of the function associated with the at least one characteristics of the function may be identified. Some quantity (e.g. a spatial-temporal information of the object) may be determined based on the at least one argument of the function.

A characteristics of a motion of an object in the venue may comprise at least one of: an instantaneous characteristics, a short-term characteristics, repetitive characteristics, a recurring characteristics, a history, an incremental characteristics, a changing characteristics, a deviational characteristics, a phase, a magnitude, a time characteristics, a frequency characteristics, a time-frequency characteristics, a decomposition characteristics, an orthogonal decomposition characteristics, a non-orthogonal decomposition characteristics, a deterministic characteristics, a probabilistic characteristics, a stochastic characteristics, an autocorrelation function (ACF), a mean, a variance, a statistics, a duration, a timing, a trend, a periodic characteristics, a long-term characteristics, a historical characteristics, an average characteristics, a current characteristics, a past characteristics, a future characteristics, a predicted characteristics, a location, a distance, a height, a speed, a direction, a velocity, an acceleration, a change of the acceleration, an angle, an angular speed, an angular velocity, an angular acceleration of the object, a change of the angular acceleration, an orientation of the object, an angular of a rotation, a deformation of the object, a shape of the object, a change of shape of the object, a change of size of the object, a change of structure of the object, and/or a change of characteristics of the object.

At least one local maximum and at least one local minimum of the function may be identified. At least one local signal-to-noise-ratio-like (SNR-like) parameter may be computed for each pair of adjacent local maximum and local minimum. The SNR-like parameter may be a function (e.g. linear, log, exponential function, a monotonic function) of a fraction of a quantity (e.g. power, magnitude, etc.) of the local maximum over the same quantity of the local minimum. It may also be the function of a difference between the quantity of the local maximum and the same quantity of the local minimum.

Significant local peaks may be identified or selected. Each significant local peak may be a local maximum with SNR-like parameter greater than a threshold T1 and/or a local maximum with amplitude greater than a threshold T2.

The at least one local minimum and the at least one local minimum in the frequency domain may be identified/computed using a persistence-based approach.

A set of selected significant local peaks may be selected from the set of identified significant local peaks based on a selection criterion. The characteristics/spatial-temporal information of the object may be computed based on the set of selected significant local peaks and frequency values associated with the set of selected significant local peaks.

In one example, the selection criterion may always correspond to select the strongest peaks in a range. While the strongest peaks may be selected, the unselected peaks may still be significant (rather strong).

Unselected significant peaks may be stored and/or monitored as "reserved" peaks for use in future selection in future sliding time windows. As an example, there may be a particular peak (at a particular frequency) appearing consistently over time. Initially, it may be significant but not selected (as other peaks may be stronger). But in later time, the peak may become stronger and more dominant and may be selected. When it became "selected", it may be back-traced in time and made "selected" in the earlier time when it was significant but not selected. In such case, the back-traced peak may replace a previously selected peak in an early time. The replaced peak may be the relatively weakest, or a peak that appear in isolation in time (i.e. appearing only briefly in time).

In another example, the selection criterion may not correspond to select the strongest peaks in the range. Instead, it may consider not only the "strength" of the peak, but the "trace" of the peak—peaks that may have happened in the past, especially those peaks that have been identified for a long time.

For example, if a finite state machine (FSM) is used, it may select the peak(s) based on the state of the FSM. Decision thresholds may be computed adaptively based on the state of the FSM.

A similarity score may be computed (e.g. by a server, the processor, the Type 1 device, the Type 2 device, a local server, a cloud server, and/or another device) based on a pair of temporally adjacent CI of a time series of CI. The pair may come from the same sliding window or two different sliding windows. The similarity score may also be based on a pair of, temporally adjacent or not so adjacent, CI from two different time series of CI. The similarity score may be or may include: a time reversal resonating strength (TRRS), a correlation, a cross-correlation, an auto-correlation, a covariance, a cross-covariance, an auto-covariance, an inner product of two vectors, a distance score, a discrimination score, a metric, a neural network output, a deep learning network output, and/or another score. The characteristics and/or spatial-temporal information may be determined/computed based on the similarity score.

Any threshold may be pre-determined, adaptively determined and/or determined by a finite state machine. The adaptive determination may be based on time, space, location, antenna, path, link, state, battery life, remaining battery life, available power, available computational resources, available network bandwidth, etc.

A threshold to be applied to a test statistics to differentiate two events (or two conditions, or two situations, or two states), A and B, may be determined. Data (e.g. CI, channel state information (CSI)) may be collected under A and/or under B in a training situation. The test statistics may be computed based on the data. Distributions of the test statistics under A may be compared with distributions of the test statistics under B, and the threshold may be chosen according to some criteria. The criteria may comprise: maximum likelihood (ML), maximum aposterior probability (MAP), discriminative training, minimum type 1 error for a given type 2 error, minimum type 2 error for a given type 1 error, and/or other criteria. The threshold may be adjusted to achieve different sensitivity to the A, B and/or another event/condition/situation/state. The threshold adjustment may be automatic, semi-automatic and/or manual. The threshold adjustment may be applied once, sometimes, often, periodically, occasionally, sporadically, and/or on demand. The threshold adjustment may be adaptive. The threshold adjustment may depend on the object, an object movement/location/direction/action, an object characteristics/spatial-temporal information/size/property/trait/habit/behavior, the venue, a feature/fixture/furniture/barrier/material/machine/living thing/thing/object/boundary/surface/medium that is in/at/of the venue, a map, a constraint of the map, the event/state/situation/condition, a time, a timing, a duration, a current state, a past history, a user, and/or a personal preference, etc.

A stopping criterion of an iterative algorithm may be that change of a current parameter (e.g. offset value) in the updating in an iteration is less than a threshold. The threshold may be 0.5, 1, 1.5, 2, or another number. The threshold may be adaptive. It may change as the iteration progresses. For the offset value, the adaptive threshold may be determined based on the task, particular value of the first time, the current time offset value, the regression window, the regression analysis, the regression function, the regression error, the convexity of the regression function, and/or an iteration number.

The local extremum may be determined as the corresponding extremum of the regression function in the regression window. The local extremum may be determined based on a set of time offset values in the regression window and a set of associated regression function values. Each of the set of associated regression function values associated with the set of time offset values may be within a range from the corresponding extremum of the regression function in the regression window.

The searching for a local extremum may comprise a robust search, a minimization, a maximization, an optimization, a statistical optimization, a dual optimization, a constraint optimization, a convex optimization, a global optimization, a local optimization an energy minimization, a linear regression, a quadratic regression, a higher order regression, a linear programming, a nonlinear programming, a stochastic programming, a combinatorial optimization, a constraint programming, a constraint satisfaction, a calculus of variations, an optimal control, a dynamic programming, a mathematical programming, a multi-objective optimization, a multi-modal optimization, a disjunctive programming, a space mapping, an infinite-dimensional optimization, a heuristics, a metaheuristics, a convex programming, a semidefinite programming, a conic programming, a cone programming, an integer programming, a quadratic programming, a fractional programming, a numerical analysis, a simplex algorithm, an iterative method, a gradient descent, a subgradient method, a coordinate descent, a conjugate gradient method, a Newton's algorithm, a sequential quadratic programming, an interior point method, an ellipsoid method, a reduced gradient method, a quasi-Newton method, a simultaneous perturbation stochastic approximation, an interpolation method, a pattern search method, a line search, a non-differentiable optimization, a genetic algorithm, an evolutionary algorithm, a dynamic relaxation, a hill climbing, a particle swarm optimization, a gravitation search algorithm, a simulated annealing, a memetic algorithm, a differential evolution, a dynamic relaxation, a stochastic tunneling, a Tabu search, a reactive search optimization, a curve fitting, a least square, a simulation based optimization, a variational calculus, and/or a variant. The search for a local extremum may be associated with an objective function, a loss function, a cost function, a utility function, a fitness function, an energy function, and/or an energy function.

Regression may be performed using a regression function to fit sampled data (e.g. CI, a feature of CI, a component of CI) or another function (e.g. autocorrelation function) in a regression window. In at least one iteration, a length of the regression window and/or a location of the regression window may change. The regression function may be a linear function, a quadratic function, a cubic function, a polynomial function, and/or another function.

The regression analysis may minimize an absolute error, a square error, a higher order error (e.g. third order, fourth order, etc.), a robust error (e.g. square error for smaller error magnitude and absolute error for larger error magnitude, or a first kind of error for smaller error magnitude and a second kind of error for larger error magnitude), another error, a weighted sum of absolute error (e.g. for a wireless transmitter with multiple antennas and a wireless receiver with multiple antennas, each pair of transmitter antenna and receiver antenna form a link. Error associated with different links may have different weights. One possibility is that some links and/or some components with larger noise may have smaller or bigger weight.), a weighted sum of square error, a weighted sum of higher order error, a weighted sum of robust error, a weighted sum of the another error, an absolute cost, a square cost, a higher order cost, a robust cost, another cost, a weighted sum of absolute cost, a weighted sum of square cost, a weighted sum of higher order cost, a weighted sum of robust cost, and/or a weighted sum of another cost.

The regression error determined may be an absolute error, a square error, a higher order error, a robust error, yet another error, a weighted sum of absolute error, a weighted sum of square error, a weighted sum of higher order error, a weighted sum of robust error, and/or a weighted sum of the yet another error.

The time offset associated with maximum regression error (or minimum regression error) of the regression function with respect to the particular function in the regression window may become the updated current time offset in the iteration.

A local extremum may be searched based on a quantity comprising a difference of two different errors (e.g. a difference between absolute error and square error). Each of the two different errors may comprise an absolute error, a square error, a higher order error, a robust error, another error, a weighted sum of absolute error, a weighted sum of square error, a weighted sum of higher order error, a weighted sum of robust error, and/or a weighted sum of the another error.

The quantity may be compared with an F-distribution, a central F-distribution, another statistical distribution, a threshold, a threshold associated with a probability, a threshold associated with a probability of finding a false peak, a threshold associated with the F-distribution, a threshold associated the central F-distribution, and/or a threshold associated with the another statistical distribution.

The regression window may be determined based on at least one of: the movement of the object, a quantity associated with the object, the at least one characteristics and/or spatial-temporal information of the object associated with the movement of the object, an estimated location of the local extremum, a noise characteristics, an estimated noise characteristics, an F-distribution, a central F-distribution, another statistical distribution, a threshold, a preset threshold, a threshold associated with a probability, a threshold associated with a desired probability, a threshold associated with a probability of finding a false peak, a threshold associated with the F-distribution, a threshold associated the central F-distribution, a threshold associated with the another statistical distribution, a condition that a quantity at the window center is largest within the regression window, a condition that the quantity at the window center is largest within the regression window, a condition that there is only one of the local extremum of the particular function for the particular value of the first time in the regression window, another regression window, and/or another condition.

The width of the regression window may be determined based on the particular local extremum to be searched. The local extremum may comprise first local maximum, second local maximum, higher order local maximum, first local maximum with positive time offset value, second local maximum with positive time offset value, higher local maximum with positive time offset value, first local maximum with negative time offset value, second local maximum with negative time offset value, higher local maximum with negative time offset value, first local minimum, second local minimum, higher local minimum, first local minimum with positive time offset value, second local minimum with positive time offset value, higher local minimum with positive time offset value, first local minimum with negative time offset value, second local minimum with negative time offset value, higher local minimum with negative time offset value, first local extremum, second local extremum, higher local extremum, first local extremum with positive time offset value, second local extremum with positive time offset value, higher local extremum with positive time offset value, first local extremum with negative time offset value, second local extremum with negative time offset value, and/or higher local extremum with negative time offset value.

A current parameter (e.g. time offset value) may be initialized based on a target value, a target profile, a trend, a past trend, a current trend, a target speed, a speed profile, a target speed profile, a past speed trend, the movement of the object, at least one characteristics and/or spatial-temporal information of the object associated with the movement of object, a positional quantity of the object, an initial speed of the object associated with the movement of the object, a predefined value, an initial width of the regression window, a time duration, a value based on a carrier frequency of the wireless signal, a bandwidth of the wireless signal, an amount of antennas associated with the wireless multipath channel, a noise characteristics, and/or an adaptive value. The current time offset may be at the center, on the left side, on the right side, and/or at another fixed relative location, of the regression window.

FIG. 1 illustrates an exemplary network environment 100 for vital sign detection and monitoring in a venue, according to one embodiment of the present teaching. As shown in FIG. 1, the exemplary network environment 100 includes a transmitter 110, an antenna 112, a wireless channel 130, an antenna 122, and a receiver 120. The antenna 112 is electrically coupled to the transmitter 110; the antenna 122 is electrically coupled to the receiver 120.

In one embodiment, the transmitter 110 is located at a first position in a venue; while the receiver 120 is located at a second position in the venue. The transmitter 110 is configured for transmitting a wireless signal through the wireless channel 130. The wireless channel 130 in this example is a wireless multipath channel that is impacted by a pseudo-periodic motion of an object in the venue. According to various embodiments, the object may be a human (e.g. a baby 142, or a patient 146) or a pet (e.g. a puppy 144). The receiver 120 in this example receives the wireless signal through the wireless multipath channel 130 and obtains at least one time series of channel information (CI) of the wireless multipath channel based on the wireless signal. Because the motion of the object impacts the wireless multipath channel through which the wireless signal is transmitted, the channel information 125 extracted from the wireless signal includes information related to the object motion.

In various embodiments, the transmitter 110 may be part of a Bot or a Type 1 device placed in a venue, while the receiver 120 may be part of an Origin or a Type 2 device placed in the venue. In various embodiments, the Bot and/or the Origin may include (not shown) multiple transmitters, multiple receivers, and/or multiple transceivers. In one embodiment, the antenna 112 and/or the antenna 122 is replaced with a multi-antenna array that can form a plurality of beams each of which points in a distinct direction. The transmitter 110 can be configured to wirelessly transmit signals having different types or functions. Similarly, the receiver 120 is configured to receive wireless signals having different types or functions. In one embodiment, the transmitter 110 has at least one antenna; and the receiver 120 has at least one antenna. Each of the at least one time series of CI is associated with one of the at least one antenna of the transmitter 110 and one of the at least one antenna of the receiver 120.

Figure 2:
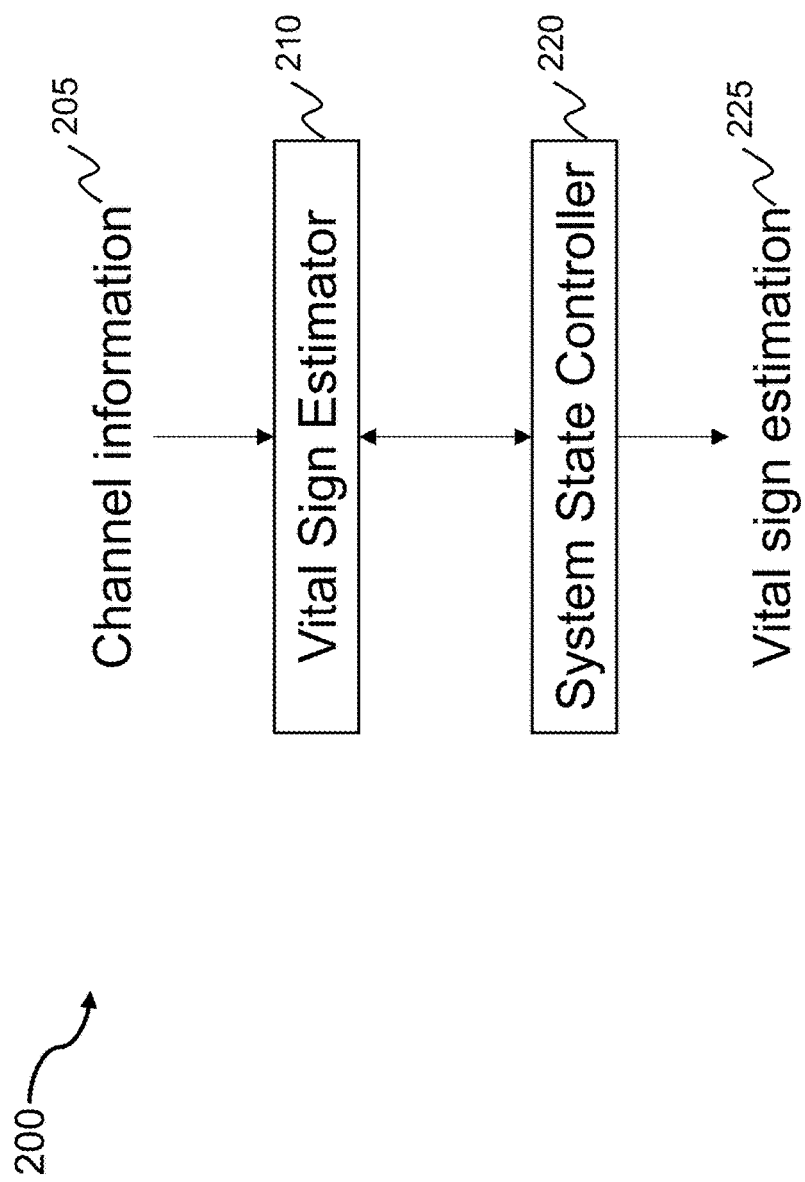
FIG. 2 illustrates an exemplary block diagram of a system for vital sign detection and monitoring, according to one embodiment of the present teaching.

FIG. 2 illustrates an exemplary block diagram of a system 200 for vital sign detection and monitoring, according to one embodiment of the present teaching. As shown in FIG. 2, the exemplary vital sign monitoring system 200 comprises a vital sign estimator 210 and a system state controller 220. The vital sign estimator 210 receives an input of a time series of channel information (TSCI) 205, which may be the channel information 125 generated by the receiver 120. According to various embodiments, the system can detect and monitor various periodic and pseudo-periodic motions, whether they represent vital signs or not.

In one embodiment, the system 200 may comprise the transmitter 110, the receiver 120 and their respective antennas as well. The vital sign estimator may be coupled to at least one of: the transmitter 110, the receiver 120, an additional transmitter, an additional receiver, a cloud server, a fog server, a local server, and an edge server.

In one embodiment, the vital sign estimator 210 is configured for determining that at least one portion of the TSCI 205 in a current sliding time window is associated with a pseudo-periodic motion of the object (e.g. breathing of a person) in the venue, and computing a current characteristics (e.g. a repetition rate, a breathing rate) related to the pseudo-periodic motion of the object in the current sliding time window based on at least one of: the at least one portion of the TSCI 205 in the current sliding time window, at least one portion of the at least one TSCI 205 in a past sliding time window, and a past characteristics related to the pseudo-periodic motion of the object in the past sliding time window. Here, a "portion" of a time series of CI may be those CI in the corresponding time window such as current time window, or past time window. The computation may be based on a comparison between a current sliding time window of the at least one portion of the at least one TSCI 205 with a past sliding time window of the at least one portion of the at least one TSCI 205, and maybe based on the past characteristics. A repetition rate (e.g. breathing rate) can be represented by the repetition frequency (e.g. breathing frequency), e.g. 20 bpm. It can also be a period corresponding to the breathing frequency, e.g. 3 seconds for 20 bpm (60/20=3).

According to various embodiments, at least one of the current characteristics and the past characteristics comprises information related to at least one of: a frequency of pseudo-periodic motion, a frequency characteristics, a frequency spectrum, a time period of pseudo periodic motion, a temporal characteristics, a temporal profile, a timing of pseudo-periodic motion, a starting time, an ending time, a duration, a history of motion, a motion type, a motion classification, a location of the object, a speed, a displacement, an acceleration, a rotational speed, a rotational characteristics, a gait cycle of the object, a transient behavior of the object, a transient motion, a change in pseudo-periodic motion, a change in frequency of pseudo-periodic motion, a change in gait cycle, an event associated with pseudo-periodic motion, an event associated with transient motion, a sudden-motion event, and a fall-down event.

In one embodiment, the vital sign estimator 210 is further configured for making the current characteristics related to the pseudo-periodic motion of the object available in real time; and moving the current sliding time window by a shift-size as time progresses.

In one embodiment, the system also includes an additional transmitter located at a third position in the venue and configured for transmitting an additional wireless signal through the wireless multipath channel 130 impacted by the pseudo-periodic motion of the object in the venue; and an additional receiver located at a fourth position in the venue and configured for: receiving the additional wireless signal through the wireless multipath channel, and obtaining an additional time series of channel information (CI) of the wireless multipath channel 130 based on the additional wireless signal. In this embodiment, the vital sign estimator 210 is further configured for: determining that at least one portion of the additional TSCI in the current sliding time window is associated with the pseudo-periodic motion of the object in the venue, and computing the current characteristics related to the pseudo-periodic motion of the object in the current sliding time window based on at least one of: the at least one portion of the additional TSCI in the current sliding time window, at least one portion of the additional TSCI in an additional past sliding time window, and a past characteristics related to the pseudo-periodic motion of the object in the additional past sliding time window. To implement this embodiment, a system may include more than one pair of Bot and Origin, each pair giving rise to independent CI. Repetition rate (e.g. breathing rate) may be computed individually based on the individual pair or jointly based on both pairs. Results of two different Bot-Origin pairs may be combined. Each pair may use different method to obtain the repetition rate (e.g. breathing rate). Thresholds may be different. The two pairs may have a common Bot, or a common Origin.

In another embodiment, two or more pseudo-periodic object motions are monitored at the same time. For example, the same current characteristics (e.g. repetition rate, breathing rate) of the two people are computed based on the same current sliding window of CI. In this case, the vital sign estimator 210 is further configured for: determining that at least one portion of the at least one TSCI in the current sliding time window is associated with an additional pseudo-periodic motion of an additional object in the venue, wherein the wireless multipath channel is further impacted in the current sliding time window by the additional pseudo-periodic motion of the additional object; and computing a current characteristics related to the additional pseudo-periodic motion of the additional object in the current sliding time window based on at least one of: the at least one portion of the at least one TSCI in the current sliding time window, the at least one portion of the at least one TSCI in the past sliding time window, and a past characteristics related to the additional pseudo-periodic motion of the additional object in the past sliding time window. In one example, while the pseudo-periodic motion represents breathing, the additional pseudo-periodic motion represents heartbeat.

In another embodiment, the number of objects having pseudo-periodic motions is estimated. In this case, the vital sign estimator 210 is further configured for: determining that the wireless multipath channel is impacted in the current sliding time window by pseudo-periodic motions of a plurality of objects; computing current characteristics related to pseudo-periodic motions of the plurality of objects in the current sliding time window based on at least one of: the at least one portion of the at least one TSCI in the current sliding time window, the at least one portion of the at least one TSCI in the past sliding time window, and a past characteristics related to the pseudo-periodic motions of the plurality of objects in the past sliding time window; and estimating a quantity of the plurality of objects based on the current characteristics.

The system state controller 220 in this example may comprise a finite state machine (FSM) configured for tuning parameters (e.g. peak detection thresholds under different states) of the system 200, for the system to output an accurate vital sign estimation 225, which may include an estimate of the vital sign characteristics (e.g. the breathing rate) and/or the quantity of objects (e.g. persons that are breathing). In one embodiment, the system state controller 220 is configured for computing adaptively at least one of: decision thresholds, threshold T1, threshold T2, lower bound associated with frequency of the selected significant local peaks, upper bound associated with frequency of the selected significant local peaks, search range, and a parameter associated with a selection of the selected significant local peaks, based on a finite state machine (FSM). The FSM may comprise at least one of: an Initiation (INIT) state, a Verification state, a PeakFound state, and a Motion state.

In one embodiment, the system state controller 220 is further configured for: entering the INIT state of the FSM in at least one predetermined way; computing the thresholds adaptively in a first way in the INIT state; detecting an event based on the thresholds; transitioning from the INIT state to a different state of the FSM based on at least one transition criterion; and computing the thresholds adaptively in a second way in the different state. In another embodiment, the system state controller 220 is further configured for: entering the INIT state of the FSM; computing the thresholds adaptively in a first way; detecting an event based on the thresholds and at least one of: the set of selected significant local peaks and related characteristics; detecting excessive background interfering motion based on the thresholds and the remaining spectral energy; staying in the INIT state when the event is concluded to be "not detected" and the excessive background interfering motion is concluded to be "not detected;" transitioning from the INIT state to the Verification state when the event is concluded to be "detected" preliminarily and the detected event needs to be verified; and transitioning from the INIT state to the Motion state when the excessive background interfering motion is concluded to be "detected."

In another embodiment, the system state controller 220 is further configured for: in the Verification state: computing the thresholds adaptively in a second way; accumulating and computing at least one statistics based on sets of selected significant local peaks and related characteristics in at least one adjacent sliding time window for verification of the detected event that is detected preliminarily; staying in the Verification state while the at least one statistics is being accumulated until sufficient statistics is collected for the verification; verifying the preliminarily detected event based on the thresholds and the at least one statistics; transitioning from the Verification state to the PeakFound state when the preliminarily detected event is concluded as "verified;" transitioning from the Verification state to the INIT state when verification is concluded to be "not verified;" and staying in the Verification state when verification is not concluded.

In a different embodiment, the system state controller 220 is further configured for: in the PeakFound state: computing the thresholds adaptively in a third way; detecting the verified event based on the thresholds and the at least one of: the set of selected significant local peaks and related characteristics; detecting the excessive background interfering motion based on the thresholds and the remaining spectral energy; staying in the PeakFound state when the verified event is concluded as "detected;" transitioning from the PeakFound state to the INIT state when the verified event is concluded as "not detected" for a number of time instances; and transitioning from the PeakFound state to the Motion state when the excessive background interfering motion is concluded as "detected" for a number of time instances.

In a different embodiment, the system state controller 220 is further configured for: in the Motion state: computing the thresholds adaptively in a fourth way; detecting the excessive background interfering motion based on the thresholds and the remaining spectral energy; staying in the Motion state when the excessive background interfering motion is concluded as "detected;" and transitioning from the Motion state to the INIT state when the excessive background interfering motion is concluded as "not detected" for a number of time instances.

Figure 3:
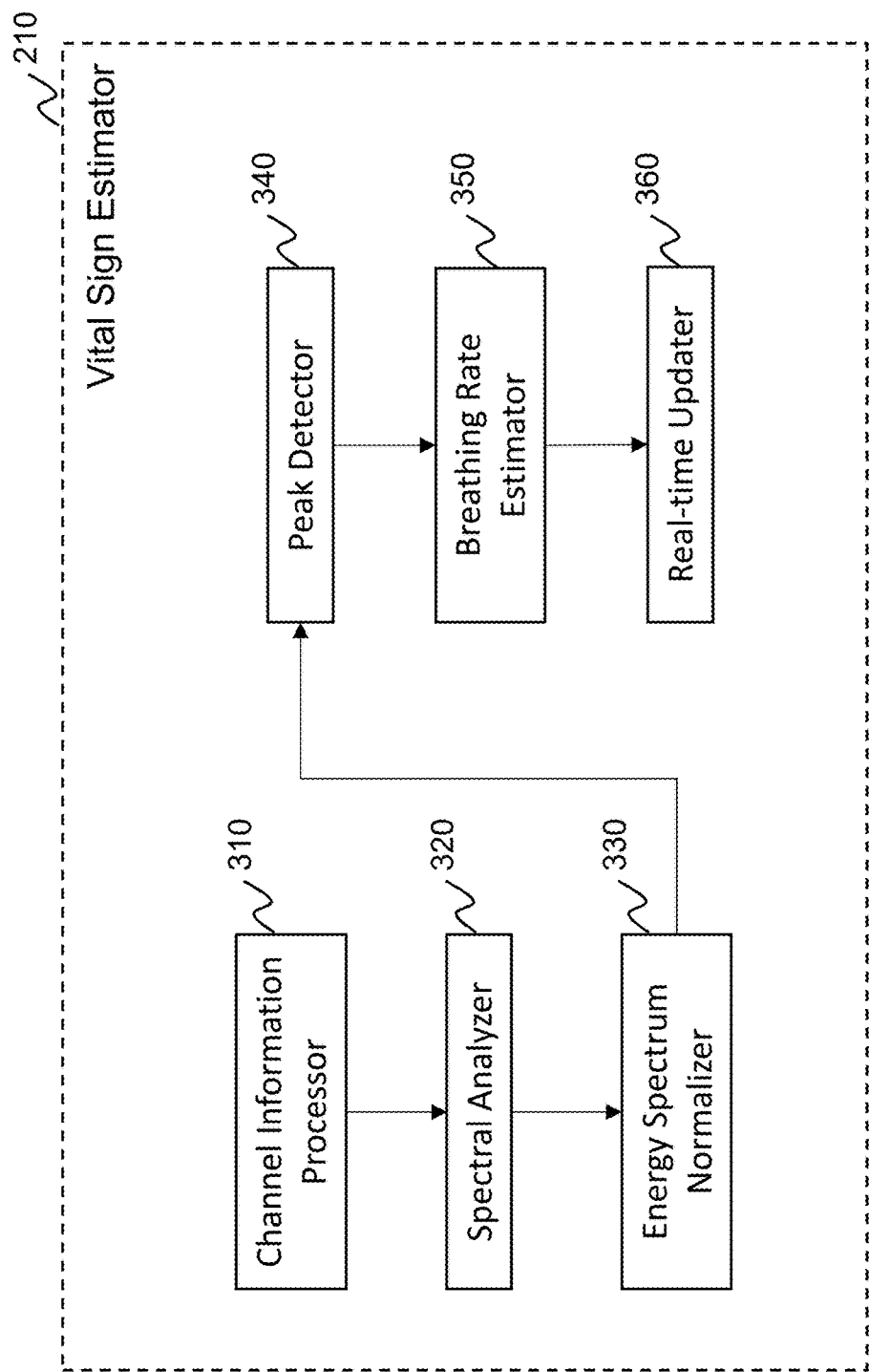
FIG. 3 illustrates an exemplary block diagram of a vital sign estimator for vital sign detection and monitoring, according to one embodiment of the present teaching.

FIG. 3 illustrates an exemplary block diagram of a vital sign estimator, e.g. the vital sign estimator 210 in FIG. 2, for vital sign detection and monitoring, according to one embodiment of the present teaching. As shown in FIG. 3, the vital sign estimator 210 in this example includes a channel information processor 310, a spectral analyzer 320, an energy spectrum normalizer 330, a peak detector 340, a breathing rate estimator 350, and a real-time updater 360.

In one embodiment, the channel information processor 310, the spectral analyzer 320, and the energy spectrum normalizer 330 are configured for processing the at least one TSCI in the current sliding time window on both time domain and frequency domain, while the peak detector 340 is configured for detecting at least one peak in the frequency domain, such that the current characteristics related to the pseudo-periodic motion of the object is computed based on the at least one peak in the frequency domain.

In one embodiment, for each CI of a particular portion of the at least one TSCI in the current sliding time window, the channel information processor 310 in this example is configured for: obtaining N1 (an integer greater than one) frequency domain components of the CI; determining a timestamp associated with the CI; and preprocessing the N1 frequency domain components. The preprocessing may comprise: cleaning phases of the N1 frequency domain components, and normalizing the N1 frequency domain components such that the N1 frequency domain components have a unity total power. In this case, the current characteristics related to the pseudo-periodic motion of the object is computed based on the preprocessed N1 frequency domain components of the CI of the particular portion of the at least one TSCI in the current sliding time window.

In another embodiment, for each CI of a particular portion of the at least one TSCI in the current sliding time window, the spectral analyzer 320 in this example is configured for: converting N1 frequency domain components of the channel information using an inverse frequency transform to N2 time domain coefficients of the channel information, and retaining first C of the N2 time domain coefficients, wherein C is not larger than N2. Each channel information is associated with a timestamp. N2 is not smaller than N1. Each of the N2 coefficients is associated with a time delay. The inverse frequency transform comprises at least one of: inverse Fourier transform, inverse Laplace transform, inverse Hadamard transform, inverse Hilbert transform, inverse sine transform, inverse cosine transform, inverse triangular transform, inverse wavelet transform, inverse integer transform, inverse power-of-2 transform, combined zero padding and transform, and inverse Fourier transform with zero padding. The spectral analyzer 320 in this example may be configured for correcting timestamps of all channel information of the particular portion of the at least one TSCI in the current sliding time window so that the corrected timestamps of time-corrected channel information are uniformly spaced in time. The correcting the timestamps may comprise: identifying a particular CI with a particular timestamp to be replaced by a time-corrected CI with a corrected timestamp, and computing the time-corrected CI by computing the C retained time domain coefficients of the time-corrected CI at the corrected timestamp using an interpolation filter associated with the corrected timestamp. In this case, the current characteristics related to the pseudo-periodic motion of the object is computed based on the time-corrected CI of the particular portion of the at least one TSCI in the current sliding time window.

The spectral analyzer 320 may be further configured for: for each of the C retained time domain coefficients: identifying a corresponding retained time domain coefficient of each CI of the particular portion of the at least one TSCI in the current sliding time window, applying bandpass filtering to all the corresponding identified retained time domain coefficients, and applying a frequency transform to all the corresponding identified retained time domain coefficients. A length of the frequency transform is not smaller than a length of the portion. In this case, the current characteristics related to the pseudo-periodic motion of the object is computed based on outputs of the frequency transform applied to each corresponding retained time domain coefficient of the CI of the particular portion of the at least one TSCI in the current sliding time window.

The spectral analyzer 320 may be further configured for: processing the outputs of the frequency transform applied to each corresponding retained time domain coefficient of the CI of the particular portion of the at least one TSCI in the current sliding time window. The frequency transform comprises at least one of: Fourier transform, Laplace transform, Hadamard transform, Hilbert transform, sine transform, cosine transform, triangular transform, wavelet transform, integer transform, power-of-2 transform, combined zero padding and transform, and/or Fourier transform with zero padding. The processing comprises at least one of: preprocessing, processing, post-processing, filtering, linear filtering, nonlinear filtering, folding, grouping, energy computation, low-pass filtering, bandpass filtering, high-pass filtering, matched filtering, enhancement, restoration, de-noising, spectral analysis, inverse linear transform, nonlinear transform, feature extraction, machine learning, recognition, labeling, training, clustering, grouping, sorting, thresholding, comparison with time-corrected channel information of another portion of another time series of channel information in another sliding time window, similarity score computation, vector quantization, compression, encryption, coding, storing, transmitting, representing, merging, combining, splitting, restricting to selected frequency band, and/or spectrum folding.

In one embodiment, the spectral analyzer 320 in this example is configured for: determining a timestamp associated with each channel information of the at least one TSCI; correcting timestamps of all channel information of a particular portion of the at least one TSCI in the current sliding time window so that the corrected timestamps of time-corrected channel information are uniformly spaced in time; and performing an operation on the time-corrected channel information with respect to the corrected timestamps. In this case, the current characteristics related to the pseudo-periodic motion of the object is computed based on an output of the operation. The operation comprises at least one of: preprocessing, processing, post-processing, filtering, linear filtering, nonlinear filtering, low-pass filtering, bandpass filtering, high-pass filtering, matched filtering, enhancement, restoration, de-noising, spectral analysis, frequency transform, inverse frequency transform, linear transform, nonlinear transform, feature extraction, machine learning, recognition, labeling, training, clustering, grouping, sorting, thresholding, peak detection, comparison with time-corrected channel information of another portion of another time series of channel information in another sliding time window, similarity score computation, vector quantization, compression, encryption, coding, storing, transmitting, representing, merging, combining, fusion, linear combination, nonlinear combination, and/or splitting.

The energy spectrum normalizer 330 in this example may be configured for: processing the outputs of the frequency transform applied to each corresponding retained time domain coefficient of the CI of the particular portion of the at least one TSCI in the current sliding time window, wherein the processing comprises at least one of: averaging, weighted averaging, averaging over selected frequency, averaging over selected time domain coefficients, and averaging over antenna links. The averaging over antenna links may be weighted averaging over the at least one TSCI. The averaging over selected time domain coefficients may be weighted averaging over the C retained time domain coefficients.

The peak detector 340 in this example is configured for: identifying at least one local maximum and at least one local minimum in the frequency domain; computing at least one local signal-to-noise-ratio-like (SNR-like) parameter for each pair of a local maximum and a local minimum adjacent to each other; and identifying significant local peaks each being at least one of: a local maximum with SNR-like parameter greater than a first threshold T1 and a local maximum with an amplitude greater than a threshold T2. The at least one local maximum and the at least one local minimum may be identified in the frequency domain using a persistence-based approach.

The breathing rate estimator 350 in this example is configured for: selecting a set of selected significant local peaks from the set of identified significant local peaks based on a selection criterion. In this case, the current characteristics related to the pseudo-periodic motion of the object is computed based on the set of selected significant local peaks and frequency values associated with the set of selected significant local peaks. The breathing rate estimator 350 may be further configured for: computing information associated with a remaining spectrum with the set of selected significant local peaks removed; and detecting an event associated with the current characteristics related to the pseudo-periodic motion of the object based on at least one of: a remaining spectral energy of the remaining spectrum, an adaptive threshold, and a finite state machine, where the event comprises at least one of: a presence, an absence, an appearance, a disappearance, a steady behavior and a non-steady behavior of at least one of: non-periodic motion, transient motion, strong motion, weak motion, strong background interference and another periodic motion. The real-time updater 360 in this example is configured for updating the breathing rate estimations generated by the breathing rate estimator 350 regularly.

Figure 4:
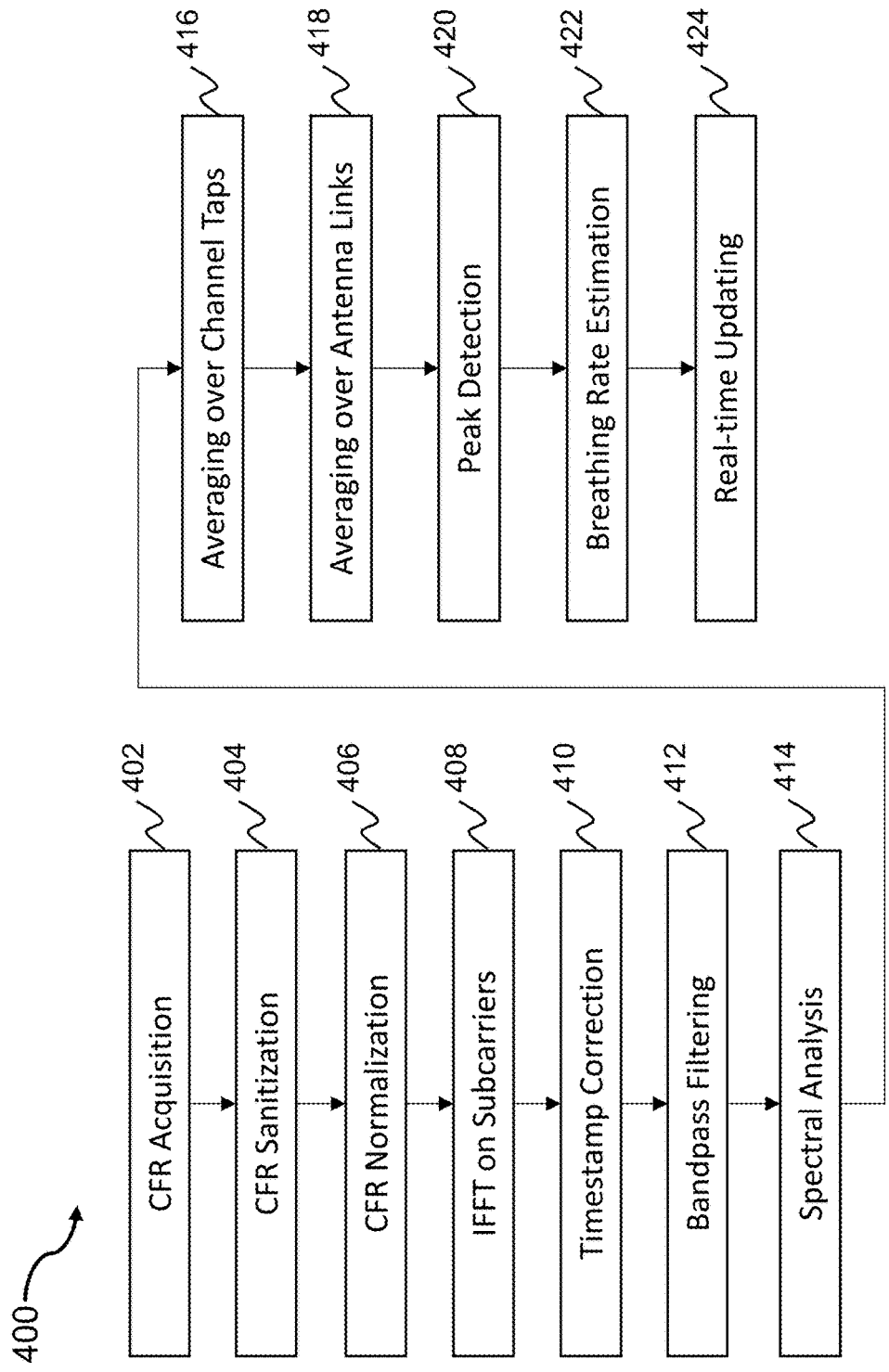
FIG. 4 illustrates a flowchart of an exemplary method for vital sign detection and monitoring, according to one embodiment of the present teaching.

FIG. 4 illustrates a flowchart of an exemplary method 400 for vital sign detection and monitoring, e.g. for breathing detection and breathing rate estimation, according to one embodiment of the present teaching. At operation 402, a channel frequency response (CFR) acquisition is performed, e.g. by the channel information processor 310 in FIG. 3. In one embodiment, the channel information processor 310 acquires CFRs from off-the-shelf WiFi chips. For example, one can obtain 114 subcarriers in a CFR frame on a 5 GHz WiFi channel with a maximum of 20 dBm transmission power. At operation 404, CFR sanitization is performed, e.g. by the channel information processor 310 in FIG. 3. In one embodiment, due to the inevitable phase misalignment between the WiFi transmitter and receiver, there exist severe phase distortions in the CFRs. To remedy this issue, one can clean the CFR phase by the conventional linear regression method. One can write the cleaned CFR on subcarrier k as G [k]. At operation 406, a CFR normalization is performed, e.g. by the channel information processor 310 in FIG. 3. In one embodiment, the receiving power of the CFRs is time-varying. Unfortunately, in the absence of automatic-gain-control (AGC) values on the CFR chips adopted, the receiving power is unmeasurable. Therefore, one can normalize the CFRs across all subcarriers such that each CFR has unit power. Although this step incurs information loss, it still leads to much-improved performance. Here, one can write the CFRs captured on different subcarriers and different time instances as a CFR matrix G with dimension K×N where N is the number of CFR frames collected. The matrix is given as $$G = \begin{bmatrix} G_{s_0}[t_0] & G_{s_0}[t_1] & \ldots & G_{s_0}[t_{N-1}] \\ G_{s_1}[t_0] & G_{s_1}[t_1] & \ldots & G_{s_1}[t_{N-1}] \\ \vdots & \vdots & \vdots & \vdots \\ G_{s_{K-1}}[t_0] & G_{s_{K-1}}[t_1] & \ldots & G_{s_{K-1}}[t_{N-1}] \end{bmatrix} \quad (1)$$

where $t_i$ stands for the time instance where the i-th CFR is captured and $s_j$ stands for the subcarrier index of the j-th subcarrier.

At operation 408, an inverse fast Fourier transform (IFFT) is performed, e.g. by the spectral analyzer 320 in FIG. 3. In one embodiment, one can convert the filtered CFRs into time-domain CIRs for de-noising using IFFT. The reason why IFFT could improve the performance lies in that: the useful signal contained in multipath components (MPC)s with a large time delay is less significant than the MPCs with a smaller time delay mainly due to the significant attenuations relevant to the propagation distance of EM waves. By using IFFT, one could focus on the first few channel taps and ignore channel taps with a large time delay. The CIR of time $t_i$ takes the form $$\underline{G}_n[t_i] = \sum_{k=s_0}^{s_{K-1}-1} G_{s_k}[t_i] e^{j2\pi \frac{nk}{K'}}, n = 0, 1, 2, \ldots, K'-1 \quad (2)$$

where K' is the size of IFFT given as $2^{ceil[log_2(K)]}$ where ceil( ) means ceiling operation.

At operation 410, a timestamp correction is performed, e.g. by the spectral analyzer 320 in FIG. 3. In one embodiment, the time instances $t_i$ can be written as $(i-1)T_s$ where $T_s$ is the CFR sampling interval. Nevertheless, in practice, other wireless systems might co-exist with the breathing tracking system. Due to the Carrier-sense multiple access with collision avoidance (CSMA/CA) mechanism, the transmission of WiFi packets are not uniformly scheduled over the air. More specifically, the WiFi devices would probe the medium before transmission. In case that some other WiFi devices are transmitting packets, the other WiFi networks in the same area must remain silent, back-off for a period of time, and probe the medium again to check if there exists on-going WiFi traffic. Therefore, one can no longer assume that $t_i=(i-1)T_s$.

To resolve this problem, one can turn to the interpolation technique. One can define the exact time instances to be interpolated as $[t_0, t_{N-1}]$ with a unit step size of $T_s$. Then, one can perform a linear interpolation onto the exact time instances based on the actual timestamps $t_0, t_1, t_2, \ldots, t_{N-1}$. This leads to the temporal corrected CIRs which can be written as $$\overline{G} = \begin{bmatrix} \overline{G}_0[t_0] & \overline{G}_0[t_1] & \ldots & \overline{G}_0[t_{N-1}] \\ \overline{G}_1[t_0] & \overline{G}_1[t_1] & \ldots & \overline{G}_1[t_{N-1}] \\ \vdots & \vdots & \vdots & \vdots \\ \overline{G}_{K'-1}[t_0] & \overline{G}_{K'-1}[t_1] & \ldots & \overline{G}_{K'-1}[t_{N-1}] \end{bmatrix} \quad (3)$$

At operation 412, a bandpass filtering is performed, e.g. by the spectral analyzer 320 in FIG. 3. In one embodiment, the CFRs can be analyzed using standard spectral analysis tools. The breathing rate of an average adult at rest ranges from 12 to 18 BPM. On the other hand, the breathing rate of an infant can be as high as 40 BPM, while the breathing rate of elderly people ranges from 10 to 30 BPM. Therefore, one can use bandpass filtering to eliminate the high-frequency and low-frequency noise and makes the breathing signal much more stable over time. This lays the foundation of the spectral analysis via FFT as the next step. For example, one can set the passband of the bandpass filter as 8 BPM to 42 BPM, which translates into 0.133 to 0.7 Hz. One can adopt a 81 taps finite-impulse-response (FIR) filter, with coefficients generated by MATLAB filter toolbox. The attenuation is −32 dB for first stopband ([0,8] BPM) and −40 dB for the right stopband ([42,300] BPM) (With a sounding rate of 10 Hz, the maximum resolvable frequency is 5 Hz which translates into 300 BPM). Denoting the filter coefficients as $h_0, h_1, \ldots, h_{H-1}$, the filtered CFR matrix can be written as $$\tilde{G} = \begin{bmatrix} \tilde{G}_0[t'_0] & \tilde{G}_0[t'_1] & \ldots & \tilde{G}_0[t'_{N'-1}] \\ \tilde{G}_1[t'_0] & \tilde{G}_1[t'_1] & \ldots & \tilde{G}_1[t'_{N'-1}] \\ \vdots & \vdots & \vdots & \vdots \\ \tilde{G}_{K'-1}[t'_0] & \tilde{G}_{K'-1}[t'_1] & \ldots & \tilde{G}_{K'-1}[t'_{N'-1}] \end{bmatrix} \quad (4)$$

where $t'_i = i \times T_s$, N' is the length of one CFR frame on a given subcarrier expressed as N−H+1, and $\tilde{G}_k[t'_j]$ represents the filtered CIR on the k-th tap, given as $$\tilde{G}_k[t'_j] = \sum_{n=0}^{H-1} h[n] \tilde{G}_k[t_{j-n}], j \geq H-1 \quad (5)$$

At operation 414, a spectral analysis via fast Fourier Transform (FFT) is performed, e.g. by the spectral analyzer 320 in FIG. 3. In one embodiment, one can perform FFT on the CIRs for each channel tap, which leads to K' spectrum estimations. The energy spectrum for the k-th tap on the u-th frequency bin is given as $$F_k[u] = \left| \sum_{i=0}^{N''-1} \tilde{G}_n[t'_i] e^{-j2\pi \frac{iu}{N''}} \right|^2, \quad (6)$$
$$u = -N''/2, -N''/2+1, \ldots, N''/2 - 1.$$

where N" is the size of FFT given as $2^{ceil[log_2(N')]}$, and the spectral resolution is thus $$\Delta f = \frac{1}{N'' \times T_s}.$$

Given that the spectrum range-of-interest is $[f_1, f_2]$ (human breathing rates are confined in a small range), the range of frequency bins of interest can be written as $[u_1 = ceil[f_1 \times N'' \times T_s], u_2 = floor[f_2 \times N'' \times T_s]]$. Further taking the harmonics of breathing signal into consideration, one can extend the frequency bin range into $[-u_2, -u_1] \cup [u_1, u_2]$. Then, one can perform a spectrum folding which leads to the folded energy spectrum given as $$\overline{F}_k[u] = \frac{1}{2}[F_k[u] + F_k[-u]], u \in \{u_1, u_1 + \Delta f, \ldots, u_2 - \Delta f, u_2\}. \quad (7)$$

Assembling the spectrum on all subcarriers together leads to the matrix F:

$$F = \begin{bmatrix} \overline{F}_{-K'/2}[u_1] & \overline{F}_{-K'/2}[u_1 + \Delta f] & \ldots & \overline{F}_{-K'/2}[u_2] \\ \overline{F}_{-K'/2+1}[u_1] & \overline{F}_{-K'/2+1}[u_1 + \Delta f] & \ldots & \overline{F}_{-K'/2+1}[u_2] \\ \ldots & \ldots & \ldots & \ldots \\ \overline{F}_{K'/2-1}[u_1] & \overline{F}_{K'/2-1}[u_1 + \Delta f] & \ldots & \overline{F}_{K'/2-1}[u_2] \\ \overline{F}_{K'/2}[u_1] & \overline{F}_{K'/2}[u_1 + \Delta f] & \ldots & \overline{F}_{K'/2}[u_2] \end{bmatrix} \quad (8)$$

At operation 416, an averaging over channel taps is performed, e.g. by the energy spectrum normalizer 330 in FIG. 3. In one embodiment, since the energy of the breathing signal concentrates in the first few CIR taps, one can take an average over channel taps with index falling in the range of [0, S−1], where S is termed as the stripe width. The averaged energy spectrum is then given as $$E[u] = \frac{1}{S} \sum_{k=0}^{S} \overline{F}_k[u], u \in \{u_1, u_1 + \Delta f, \ldots, u_2 - \Delta f, u_2\}. \quad (9)$$

At operation 418, an averaging over antenna links is performed, e.g. by the energy spectrum normalizer 330 in FIG. 3. In one embodiment, the disclosed system is a MIMO (multiple input multiple output) system. As such, there always exist multiple antennas on either end or both ends of the transmitter and receiver which gives rise to diversity in wireless communication. Here, one may also incorporate multiple antenna links in MIMO systems to improve the overall performance of breathing tracking. For each antenna link m out of a total of M links, one can calculate the folded energy spectrum as shown in (7) denoted as $\underline{F}_m[u]$, followed by computing the averaged energy spectrum over the available antenna links given as $$\dot{F}[u] = \frac{1}{M} \sum_{m=1}^{M} \underline{F}_m[u], u \in \{u_1, u_2\}. \quad (10)$$

For the convenience of further processing, one can transform the linear scale energy spectrum into its dB scale counterpart as $$\dot{F}_{dB}[u] = 10 \log_{10} \dot{F}[u] \quad (11)$$

At operation 420, a peak detection is performed, e.g. by the peak detector 340 in FIG. 3. In one embodiment, the locations of the peaks in the energy spectrum $\dot{F}_{dB}[u]$ indicate the estimated breathing rates. To extract these peaks, one may leverage the persistence-based approach to obtain multiple pairs of local maximals and local minimals. For the i-th pair of local maximum $p_{max}[i]$ and minimum $p_{min}[i]$, one may evaluate their difference as $v_i = p_{max}[i] - p_{min}[i]$, which can be regarded as the signal-to-noise ratio (SNR) for the i-th peak. Here, assuming a total of U detected peaks in the energy spectrum, one may use both the peak amplitude $\{p_{max}[i]\}_{i=1, 2, \ldots, U}$ and the local peak SNR $\{v[i]\}_{i=1, 2, \ldots, U}$ as features for further peak filtering. In particular, one may keep those peaks with amplitudes and SNRs larger than two thresholds, namely, the amplitude threshold $p_{max}{}^o$ and SNR threshold $v^o$, respectively.

At operation 422, a breathing rate estimation is performed, e.g. by the breathing rate estimator 350 in FIG. 3. In one embodiment, assuming a total of U' peaks remaining after the previous step and P breathing rates to be detected, one can pick the top P out of U' peaks and use the corresponding peak locations $\{\hat{f}_i\}_{i=1, 2, \ldots, U'}$ measured in Hz as the breathing rate estimations for P people (When P≥U', then one can suffer from a miss detection rate of $$\frac{P-U'}{P}.$$

On the other hand, when P<U', one can suffer from a false alarm rate of $$\frac{U'-P}{U'}\Big).$$

Meanwhile, one can record the spectrum energy without the peaks, denoted as $\overline{F}$ given as $$\overline{F}_{dB} = 10 \log_{10}(\Sigma_{u=u_1}^{u_2} 10^{F_{dB}[u]} - \Sigma_{i=1}^{P} 10^{p_{max}[i]}). \quad (12)$$

The metric $\overline{F}_{dB}$ is utilized to detect breathing in the finite state machine presented in the next. The breathing rate estimations with BPM as the unit are then given as $\{\hat{b}_i\}_{i=1, 2, \ldots, U'}$ with $\hat{b}_i = 60\hat{f}_i$.

At operation 424, a real-time updating of the breathing rate estimation is performed, e.g. by the real-time updater 360 in FIG. 3. In one embodiment, the disclosed breathing monitoring system keeps updating the breathing rate estimations regularly. Here, one can define another two parameters: window size $C_{window}$ and shift size $C_{shift}$, both measured in the number of samples. The first set of breathing rate estimations are generated by performing spectral analysis on CFRs with sample index [0, $C_{window}-1$], and the second set of breathing rate estimations are generated by the same procedure on CFRs with sample index [$C_{shift}$, $C_{window}+C_{shift}-1$]; the overlap between the two adjacent windows is then given as $C_{window}-C_{shift}$. A smaller $C_{shift}$ leads to a prompter real-time updating rate.

In a realistic environmental setting, there always exist motions from other people and/or objects, which introduces motion interference to the breathing tracking system. At the same time, motions of the subject under monitoring also inject interference. Both types of interferences would significantly deteriorate the performance.

Figure 5:
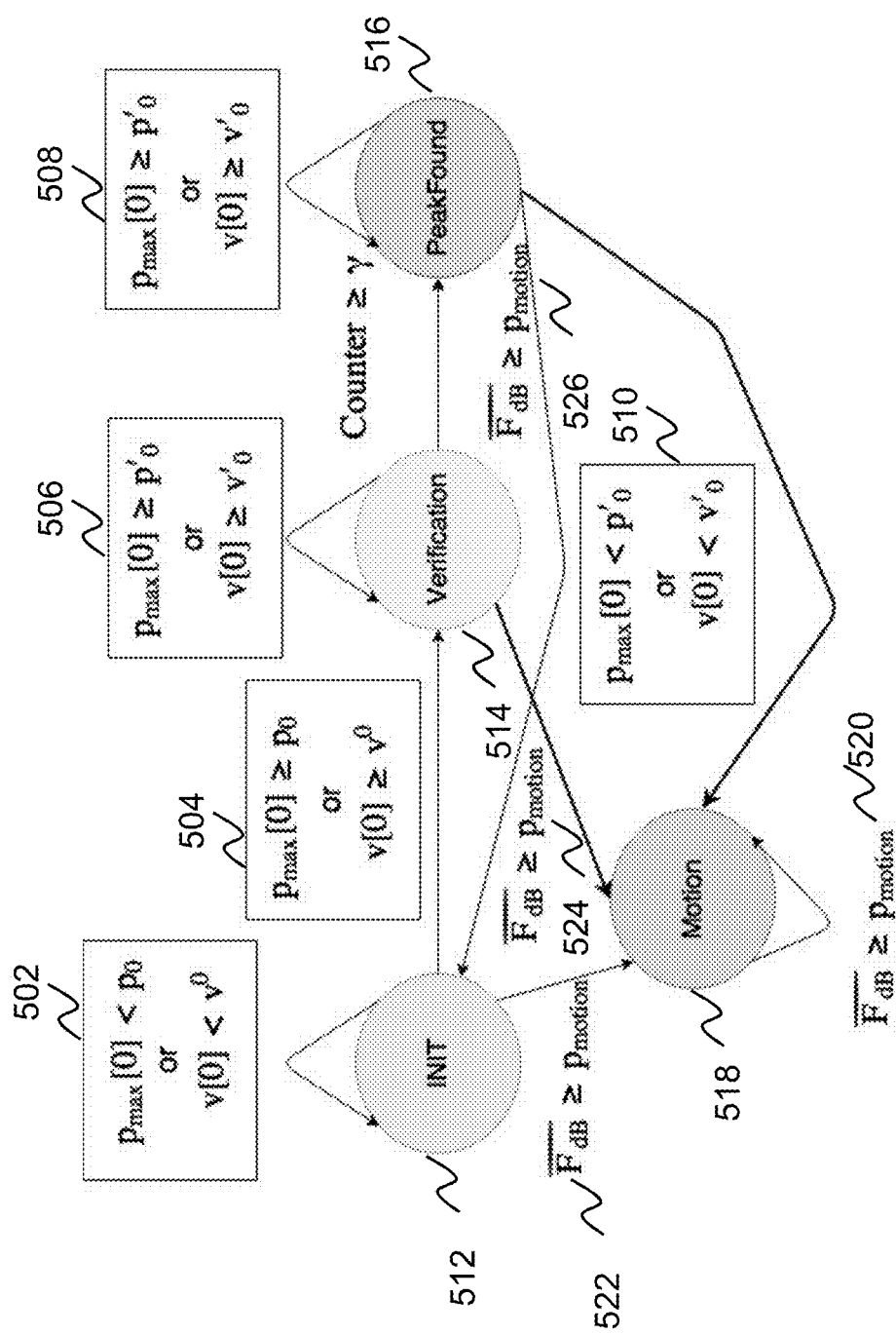
FIG. 5 illustrates an exemplary finite state machine (FSM) for single-person breathing monitoring, according to one embodiment of the present teaching.

In light of this issue, one can supplement the system with a finite-state-machine (FSM), e.g. in the system state controller 220, composed of several states into the breathing monitoring system so that the system could automatically tune its parameters such as peak detection thresholds under different states. In one embodiment, there may be four different states in the FSM which are illustrated below and as shown in FIG. 5. For convenience, the transitions are shown under the single-person breathing monitoring case. One can denote the peak search range as [$u_1$, $u_2$].

First, the FSM may have an INIT state 512. This is the default state when the system is powered on. In this state, the system uses the default peak detection thresholds ($p_{max}{}^o$, $v^o$).

If for a specific CFR time window w, it detects that $p_{max}[0] \geq p^o$, $v[0] \geq v^o$, the system would tune the peak detection thresholds as ($p'^o = p_{max}{}^o - \Delta p^o$, $v'^o = v^o - \Delta v^o$). One can introduce $\Delta p^o$ and $\Delta v^o$ to leave margins for ensuing peak detections. Then, the FSM switches to state Verification. On the other hand, if $\overline{F}_{dB} \geq p_{motion}$ where $p_{motion}$ is the threshold for motion detection, the FSM switches to the state Motion to indicate that the current time window suffers from the major motion interferences. Otherwise, it stays in the current state. The output of the INIT state is a P×1 all-zero vector implying that no breathing rate estimations can be formulated. Also, in this state, the system restores the peak search range back to [$u_1$, $u_2$].

Second, the FSM may have a Verification state 514. To avoid detection of fake peaks, one can use an internal counter to record how many times in consecutive that a peak can be detected. If a peak can be detected for a consecutive of γ time windows, then the system switches its state into state PeakFound. In case that the peak becomes weaker, the FSM switches to state INIT. When $\overline{F}_{dB}$ exceeds $p_{motion}$, the FSM switches to the motion state. Otherwise, the system stays in the current state. The output of this state is the P×1 breathing rate estimations. In this state, the system would zoom into a neighboring region of the estimated breathing rate. For instance, given an estimation of $\hat{b}$ with respect to a peak location at $\hat{f} = \hat{b}/60$, the system would select [$u'_1$, $u'_2$] where $$u'_1 = \max\left[u_1, \hat{f} - \frac{\Delta S}{2} \times N''T_S\right] \text{ and } u'_2 = \min\left[u_2, \hat{f} + \frac{\Delta S}{2} \times N'T_S\right]$$

are the starting and ending index of the updated search range. Here, ΔS stands for the size of the search range.

Third, the FSM may have a PeakFound state 516. Now, the system determines that an authentic peak is detected and can be used as the breathing rate estimation. To prevent potential error propagation, the system no longer updates the two thresholds as shown in the Verification state. In case that the peak becomes weaker, the system switches back to the INIT state. Likewise, the system would switch to the motion state for sufficiently large $\overline{F}_{dB}$. The output of this state is the P×1 breathing rate estimations. Also, the search range is updated based on the breathing rate estimations.

Fourth, the FSM may have a Motion state 518. In this state, the system decides that no credible breathing rate estimation can be produced due to the presence of strong motions. It can switch to the INIT state when $\overline{F}_{dB}$ falls below $p_{motion}$. The output of this state is the P×1 breathing rate estimations formulated in the latest Verification or PeakFound state.

The idea of using FSM to overcome the motion interference issue under the single-person case can be extended to the multi-person case by running multiple FSMs in parallel, with each FSM captures the status of one specific person.

Figure 6:
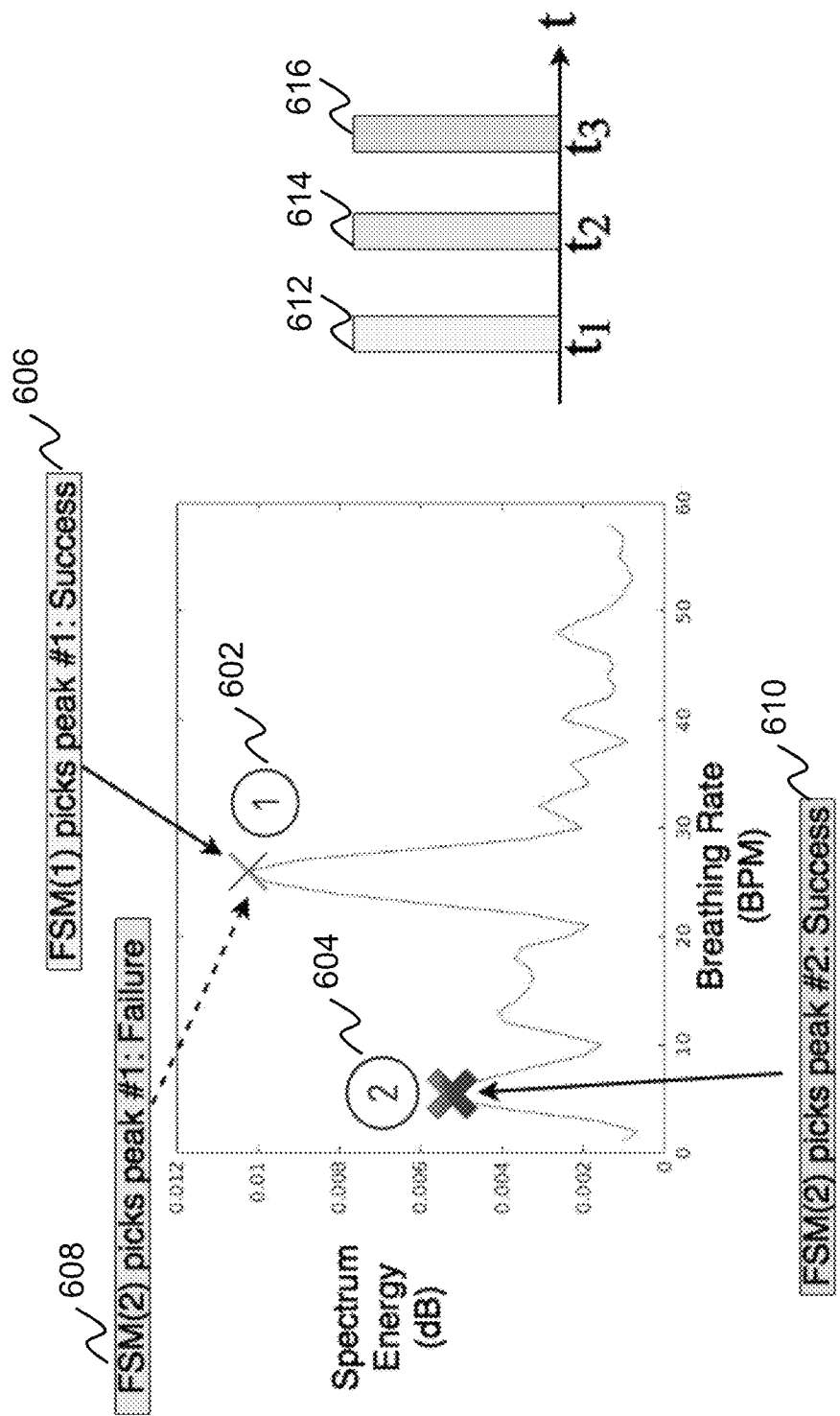
FIG. 6 illustrates an exemplary procedure for FSMs associated with different people selecting peaks, according to one embodiment of the present teaching.

The FSMs associated with different people interact with each other, i.e., they are not independent. To make the FSMs more predictable, one can define the following rules, as shown in FIG. 6.

Rule 1: FSMs operating first would always select the strongest peak in its frequency range. For example, the i-th FSM, denoted as FSM(i), selects the strongest peak in its search range [$u'_{1,i}$, $u'_{2,i}$].

Rule 2: To avoid duplication of breathing rate estimations, no two FSMs can pick the same peak in each time window. For example, if FSM(i) selects peak at location $\hat{f}_i$, then FSM(j), j>i would look for other peaks not located at $\hat{f}_i$. This rule may not handle the following issue: two persons breathing with different breathing rates. The breathing rate of one person increases and the other decreases. Sooner or later, these two breathing rates would meet each other and the disclosed FSM cannot get the breathing rate of the second person (the rendezvous problem).

Rule 3: To circumvent the situation of selecting peaks encapsulating the harmonics of breathing, FSM(i) would select the peak in its search range first denoted as $\hat{f}_i$. Then, FSM(i) checks the peaks selected by FSM(j), j=1, 2, . . . , i−1 to see if there exists a selected peak $\hat{f}_j$ such that $|2\hat{f}_i - \hat{f}_j| < \varepsilon_{harmonic}$ or $|\hat{f}_i - 2\hat{f}_j| < \varepsilon_{harmonic}$ where $\varepsilon_{harmonic}$ is a predetermined threshold. If at least one such peak can be found, then FSM(i) continues to select the next significant peak in its search range. Otherwise, FSM(i) uses $\hat{f}_i$ as the detected peak, and the same procedure is repeated for the other FSMs sequentially.

FIG. 6 visualizes an example of two FSMs selecting two peaks sequentially. One can assume that both peaks satisfy the criterion of thresholds. At time $t_1$ 602, FSM 1 searches the energy spectrum and picks the strongest peak denoted as peak 1 602, 606. Then, FSM(2) comes in and attempts to select peak 1 602, 608. However, since the first peak is already taken by FSM(1), FSM(2) gives up its selection and moves on to peak 2 604, 610.

Figure 7:
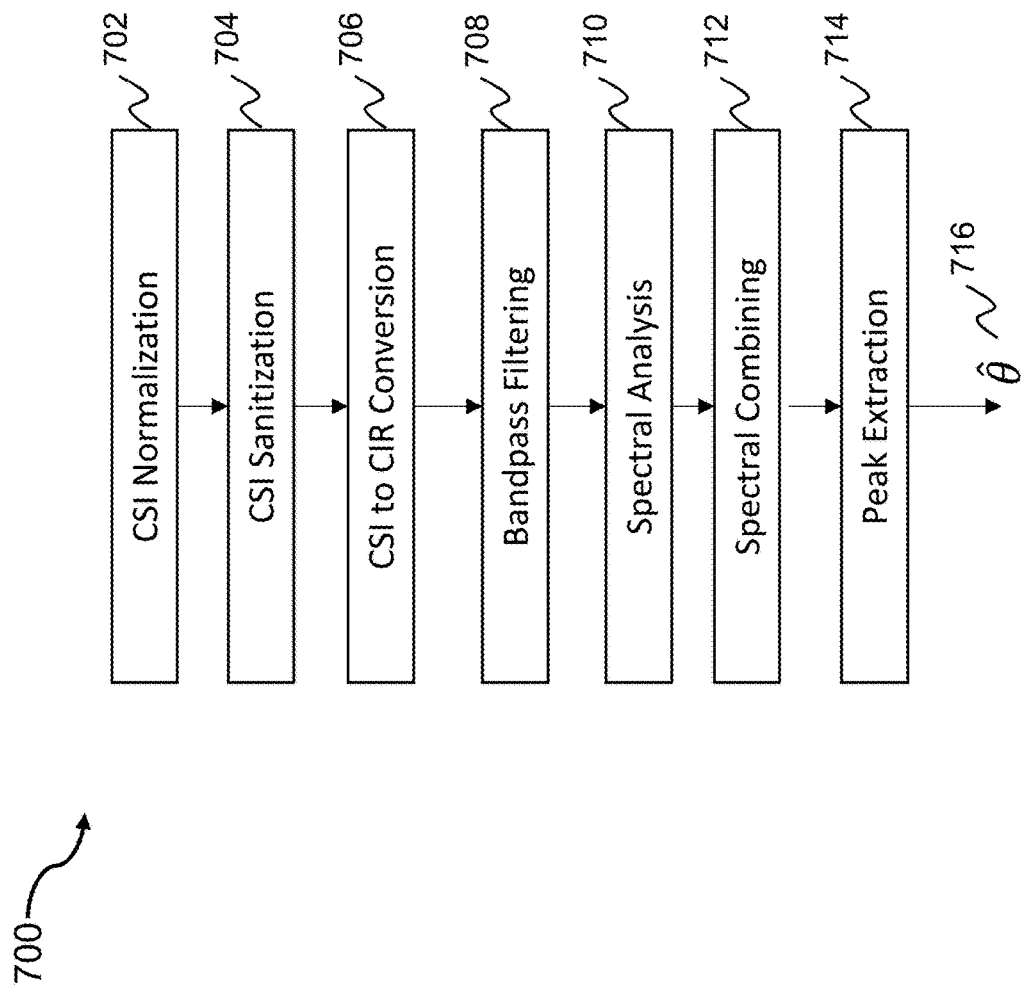
FIG. 7 illustrates a flowchart of an exemplary method for vital sign estimation, according to one embodiment of the present teaching.

In addition to the embodiments of the peak detection and FSM disclosed above, FIG. 7 illustrates a flowchart of an exemplary method 700 for vital sign estimation, according to another embodiment of the present teaching. As shown in FIG. 7, there may be no threshold when selecting the peaks. As discussed above, the vital sign estimator 210 is a core part of the breathing monitoring system. The vital sign estimator 210 may perform channel state information (CSI) normalization 702, CSI sanitization 704, frequency-domain CSI to time-domain channel impulse response (CIR) conversion 706, bandpass filtering 708, spectrum analysis 710, spectrum combining (averaging over tap and/or antenna links) 712, and peak extraction 714. Each time, one may feed N CSIs collected at N sample epochs in the vital sign estimator 210, with N being the CSI block size. Denoting $G_{comb}^{ti}$ as the combined spectrum after averaging or weighted averaging for CSI block I, any proper peak detector may be applied on $G_{comb}^{ti}$ to find several local maxima 716 denoted as $\hat{\theta}_t = \{\hat{b}_i\}_{i=0, 1, \ldots, P-1}$ where $\hat{b}_i$ stands for the breathing rate with respect to the peaks and P is the number of peaks. The process may be repeated for each CSI block i.

Figure 8:
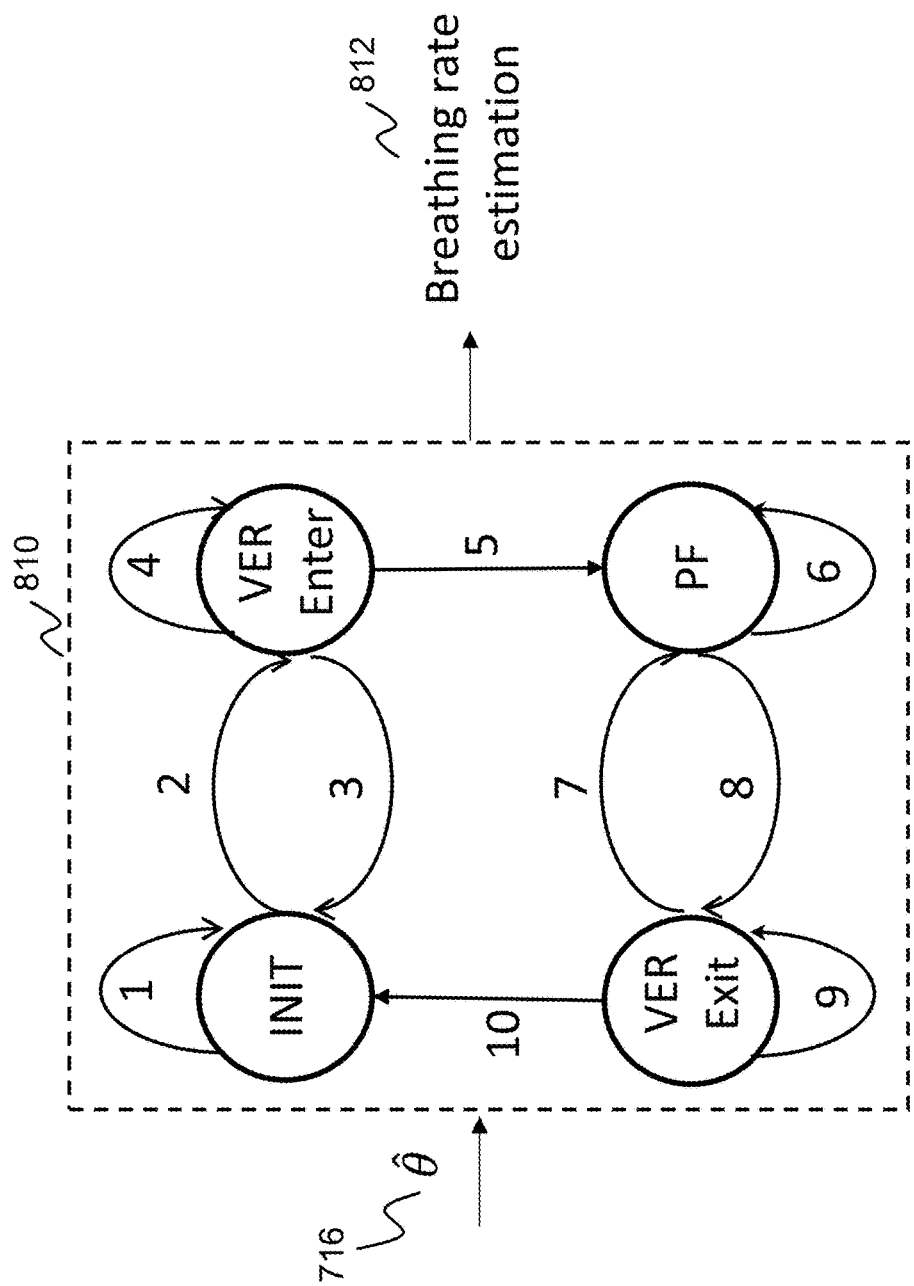
FIG. 8 illustrates an exemplary system state controller which is a FSM for single-person breathing monitoring, according to one embodiment of the present teaching.

FIG. 8 illustrates an example of FSM for single-person monitoring, according to one embodiment of the present teaching. As shown in FIG. 8, the detected peak $\hat{\theta}_t$ 716 is forwarded to the control engine sequentially for i=0, 1, 2, . . . , I−1, to output the breathing rate estimation 812. The control engine is empowered by an FSM 810 which contains four states as initialization (INIT), verification entrance (VER-Enter), peak found (PF), and verification exit (VER-End). INIT is the default state where the peak detector captures the local maxima. VER-Enter is used to evaluate the temporal consistency of the detected peaks. PF is the state after successful verification of temporally consistent peaks producing the breathing rate estimations. VER-Exit handles the case when the spectrum peaks disappear due to motions either from the subject under monitoring or other people nearby.

FIG. 9 shows a Table 900 about the state transition details of the FSM 810 shown in FIG. 8. The edge index for each column of Table 900 is marked in FIG. 8. $\hat{b}[i]$ is the output breathing rate for block i, $\dot{b}[i]$ is the internal breathing rate used by FSM, and $\Delta b$ is a variable capturing the uncertainty bound for estimation. $cnt_1$ and $cnt_2$ are counters that represent the duration of the FSM staying in the VER-Enter and VER-Exit states while $TH_1$ and $TH_2$ are the two thresholds representing how long the FSM is allowed to stay in the two states. $cnt_1$ increments by 1 when the current state is VER-Enter while $cnt_2$ increments by 1 when the current state is VER-Exit. ∩ and ∪ represent the AND condition and OR condition. $\bar{b}$ is the internal variable representing the last breathing rate estimation when the current state is PF and the next state is another state. !(Edge i) is the negate of the condition on edge i. The proposed FSM does not use any peak statistic such as the peak amplitudes for detection since the peak statistics could be very similar under cases with and without breathing which is verified experimentally.

FSM for Multi-Person Monitoring:

In case of M people to be monitored simultaneously, one can run M FSMs followed by the estimation engine. Each FSM works independently except that the estimated breathing rate from FSM m for CSI block i denoted by $\hat{b}_i^m$ should be different from all the other breathing rates and their harmonics denoted as $$\{v\hat{b}_i^{m'}\}_{m'=1,2,\ldots,M, m'\neq m}^{v=1,2,\ldots,V}$$

where V is the maximum harmonic order. One example is V=2.

Figure 10:
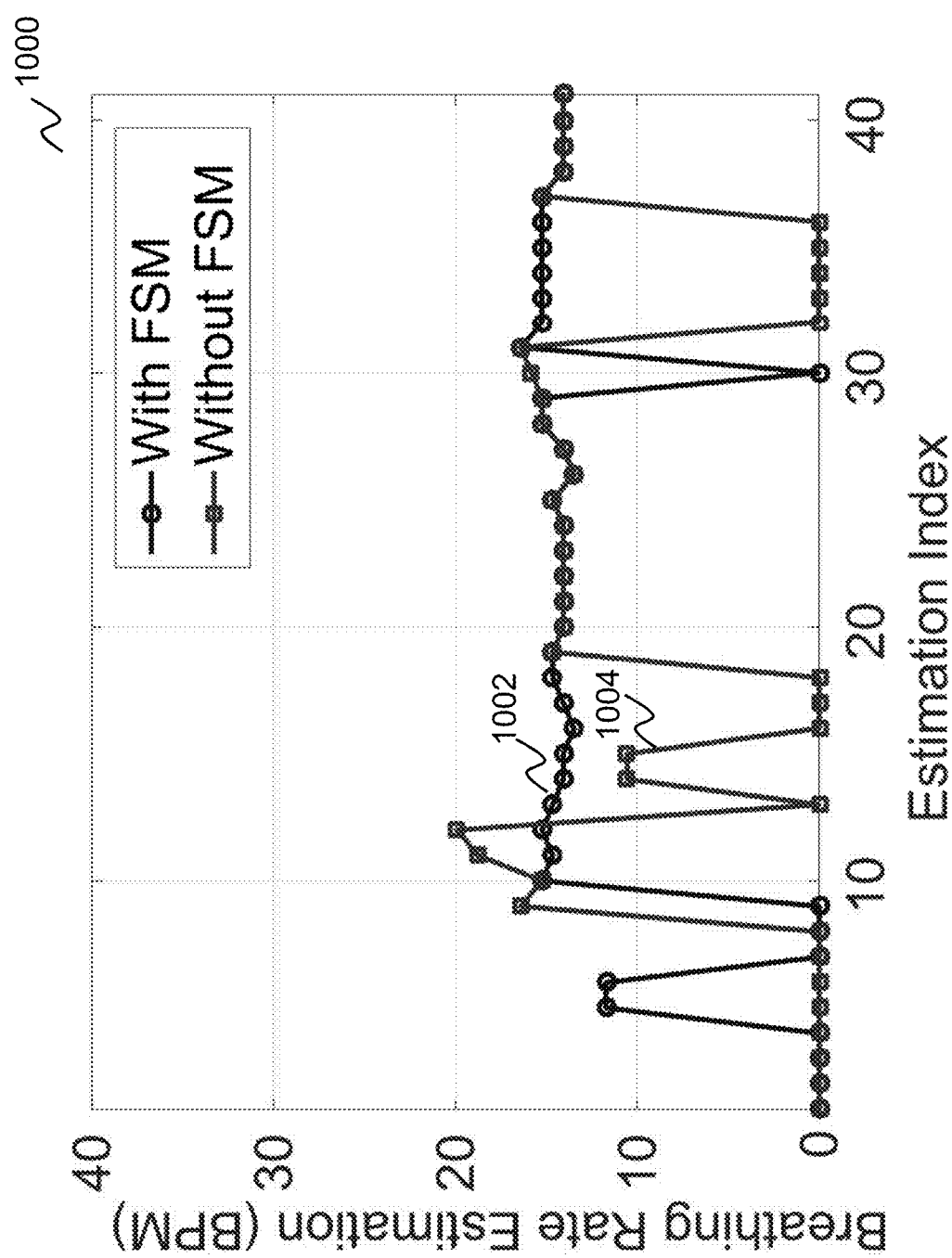
FIG. 10 illustrates an exemplary experiment result on comparison between schemes with and without FSM with a running fan, according to one embodiment of the present teaching.

Experimental Results:

Single-Person NLOS with an Operating Fan: In this experiment, one can turn on an electronic fan inside the same room with the subject. Since the fan is an electronic device with metal cover, it would reflect some EM waves and thus introduce interference to the CFRs and degrade the breathing monitoring performance. FIG. 10 shows a comparison 1000 of the performances with and without FSM. A breathing rate estimation of 0 indicates that the system is unable to obtain a reliable breathing rate. Although using FSM does not fully recover the ground-truth breathing rate (15 BPM), the utilization of FSM still enhances the overall performance. The accuracy with FSM is 94.48%.

Figure 11:
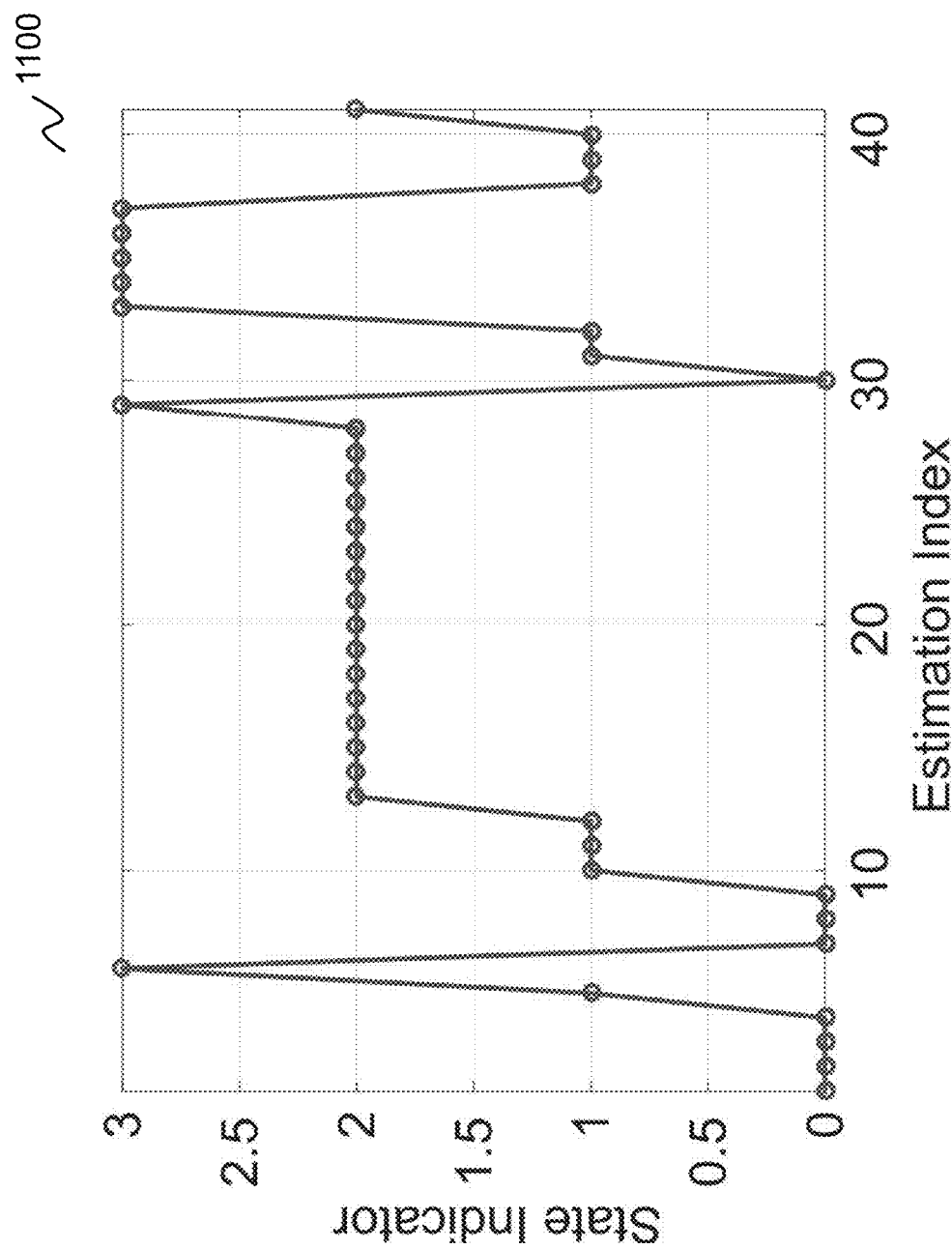
FIG. 11 illustrates an exemplary state transition of the FSM scheme with an operating fan, according to one embodiment of the present teaching.

FIG. 11 demonstrates the state transition 1100 of the FSM-based scheme in this experiment. Different states shown in FIG. 5 are encoded as follows: Init→0, Verification→1, PeakFound→2, Motion→3. FIG. 11 shows that the FSM correctly reacts to the fan moving by switching to the Motion state from time to time.

Figure 12:
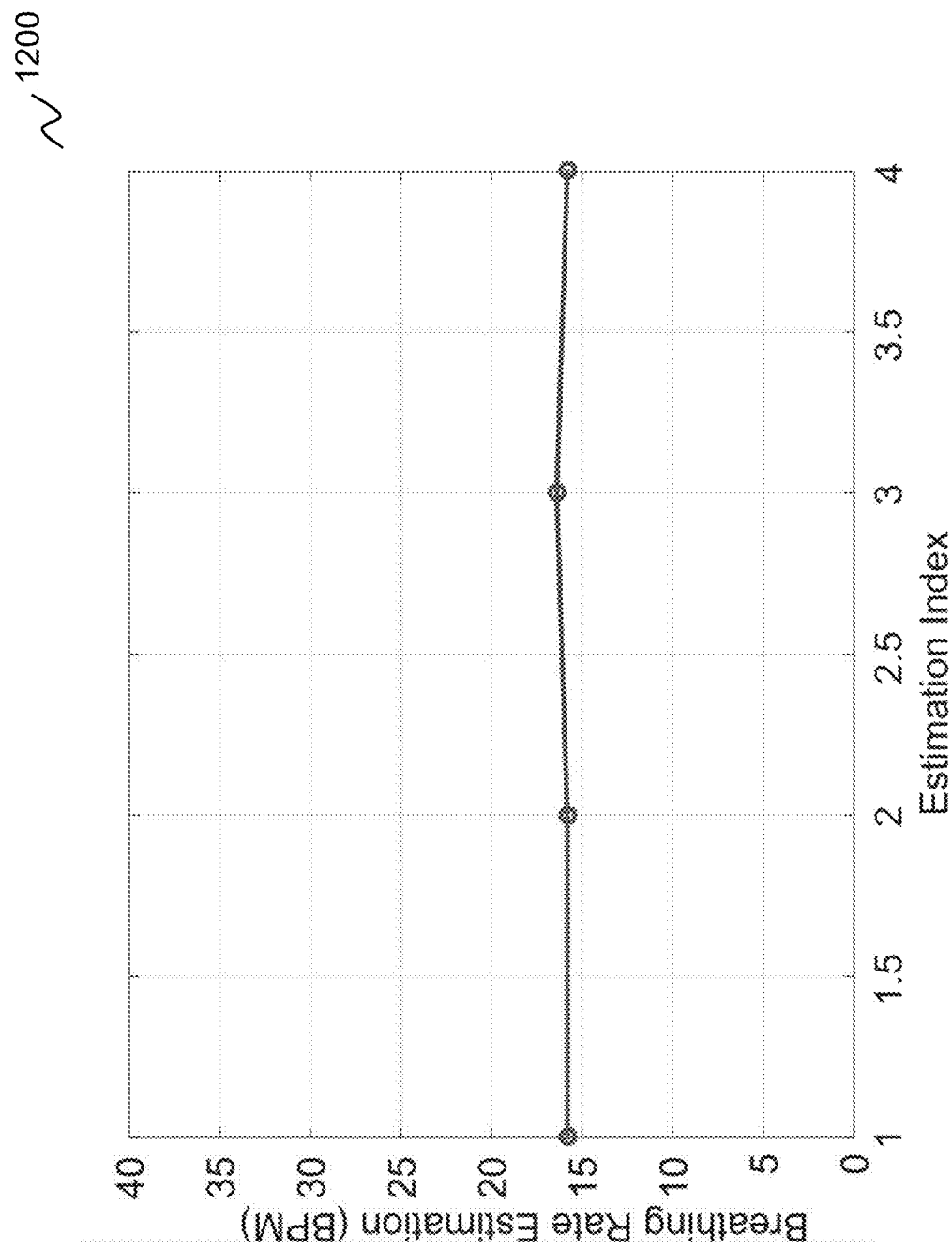
FIG. 12 illustrates an exemplary breathing estimation with subject standing up for five seconds, according to one embodiment of the present teaching.

FIG. 12 demonstrates the performance 1200 of the disclosed breathing monitoring scheme when the subject stands up for five seconds and sits down during the measurement. Clearly, the breathing monitoring scheme overcomes the impact of such large motions and produces stable breathing rate estimations over time.

Figure 13:
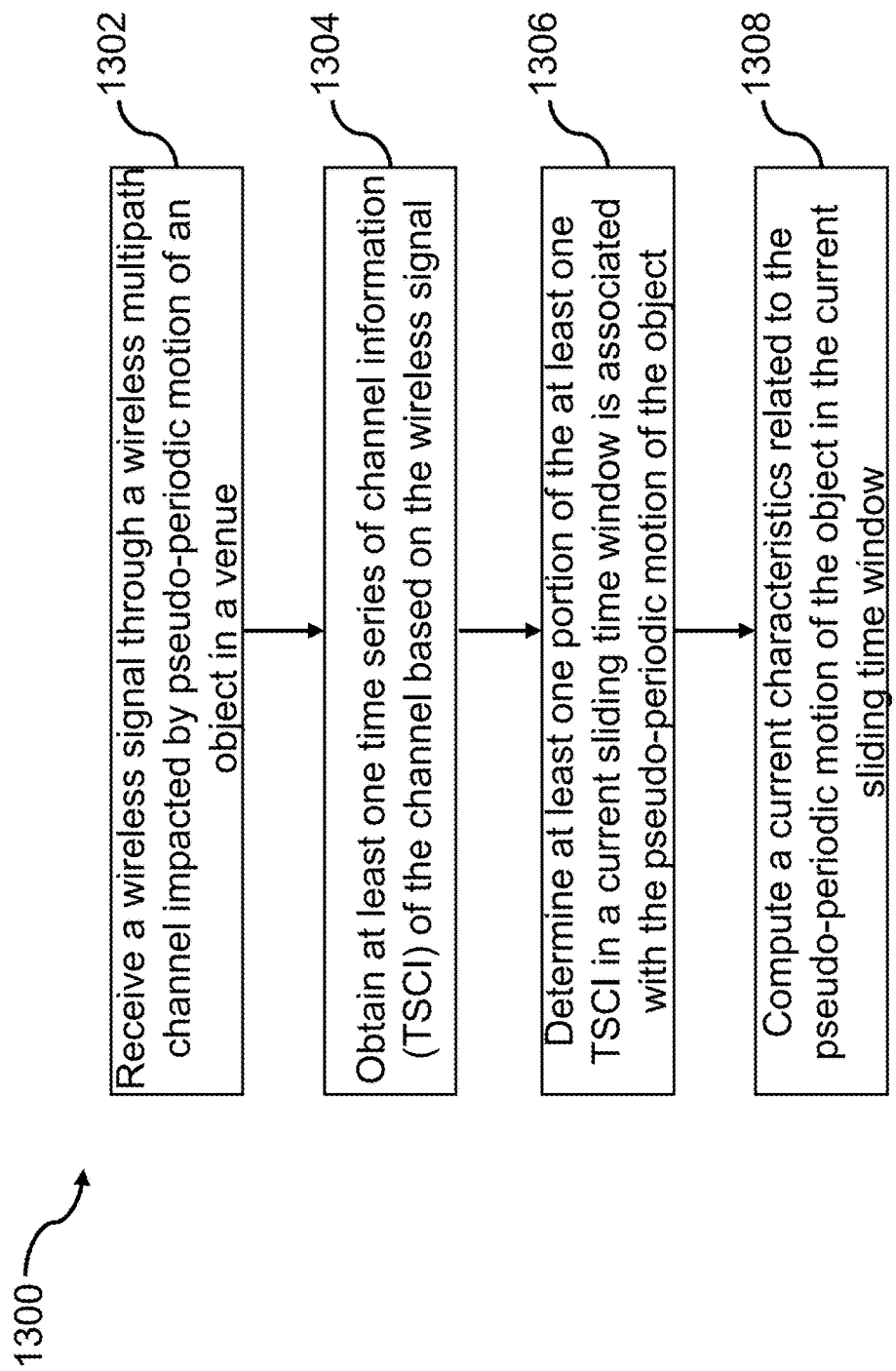
FIG. 13 illustrates an exemplary method for vital sign detection and monitoring, according to one embodiment of the present teaching.

FIG. 13 illustrates an exemplary method 1300 for vital sign detection and monitoring, according to one embodiment of the present teaching. At operation 1302, a wireless signal is received through a wireless multipath channel impacted by pseudo-periodic motion of an object in a venue. At operation 1304, at least one time series of channel information (TSCI) of the channel is obtained based on the wireless signal. At operation 1306, at least one portion of the at least one TSCI in a current sliding time window is determined to be associated with the pseudo-periodic motion of the object. At operation 1308, a current characteristics related to the pseudo-periodic motion of the object is computed in the current sliding time window.

In one embodiment, the disclosed system can estimate breathing rate of more than one people simultaneously, and can count of the amount of people. The system may include a Type 1 device which is a Bot including a transmitter, a Type 2 device which is an Origin including a receiver. The receiver can extract a time series of CSI from a wireless signal and collect CSI for a slide window (about 10-15 sec). A vital sign estimator can estimate the breathing rate based on the collected CSI. If the transmitter has M antennas and the receiver has N antennas, there are MN links. One CSI time series is obtained for each link. All MN links are used by the system to compute the breathing rate. The vital sign estimator can be located in the cloud, or in the Origin or the Type 2 device for local computing. If there are K Bots, then there can be K instances of the vital sign estimator, each serving one Bot. The breathing results of each Bot may be displayed separately on a client app of a user smart device. Results of some or all Bots may be combined to give combined results. For 1 Bot with one antenna and 1 Origin with one antenna (K=1) scenario, there is only 1 link (M=N=1). Each CSI has N1 (e.g. about 128) frequency subcarriers (called components). Each CSI is actually channel frequency response (CFR). The vital sign estimator starts by cleaning the CSI (including phase noise) and normalizing each CSI so that it has unity power. Then it does zero padding to get a vector of length N2 (e.g. 128, a power of 2). Then it performs N2-point IFFT to convert the N2-point CFR to N2-point time domain channel impulse response (CIR). The vital sign estimator then considers the sliding window of CSI (i.e. portion of the time series of CI). Suppose each window has L CSI (e.g. for a 60 seconds window with 30 samples/sec, L=60×30=1800). The vital sign estimator performs time base correction to ensure that all CSI over the sliding window are sampled at uniform sampling time. The time base correction involves resampling the CSI with some interpolation filter. Among the N2 CIR coefficients, a number (C) of significant CIR components are identified (e.g. C=5 identified among N2=128 CIR components). Then the vital sign estimator considers each CIR component of each of the L CSI and treats it as an L-point time series. As such, there are C L-point component time series formed using the C identified CIR components. Then the vital sign estimator applies bandpass filtering to each of the C component time series; and applies L2-point FFT (e.g. L2=20148 for L=1800). Then the vital sign estimator identifies local maximum (i.e. peak) in the L2-point FFT domain. The frequency corresponding to each peak is the breathing rate of a person. If it is known that K people are present, K peaks will be identified. If the amount of people is unknown, each significant peak is considered one person. By counting the significant peaks, the amount of people can be obtained.

Figure 14:
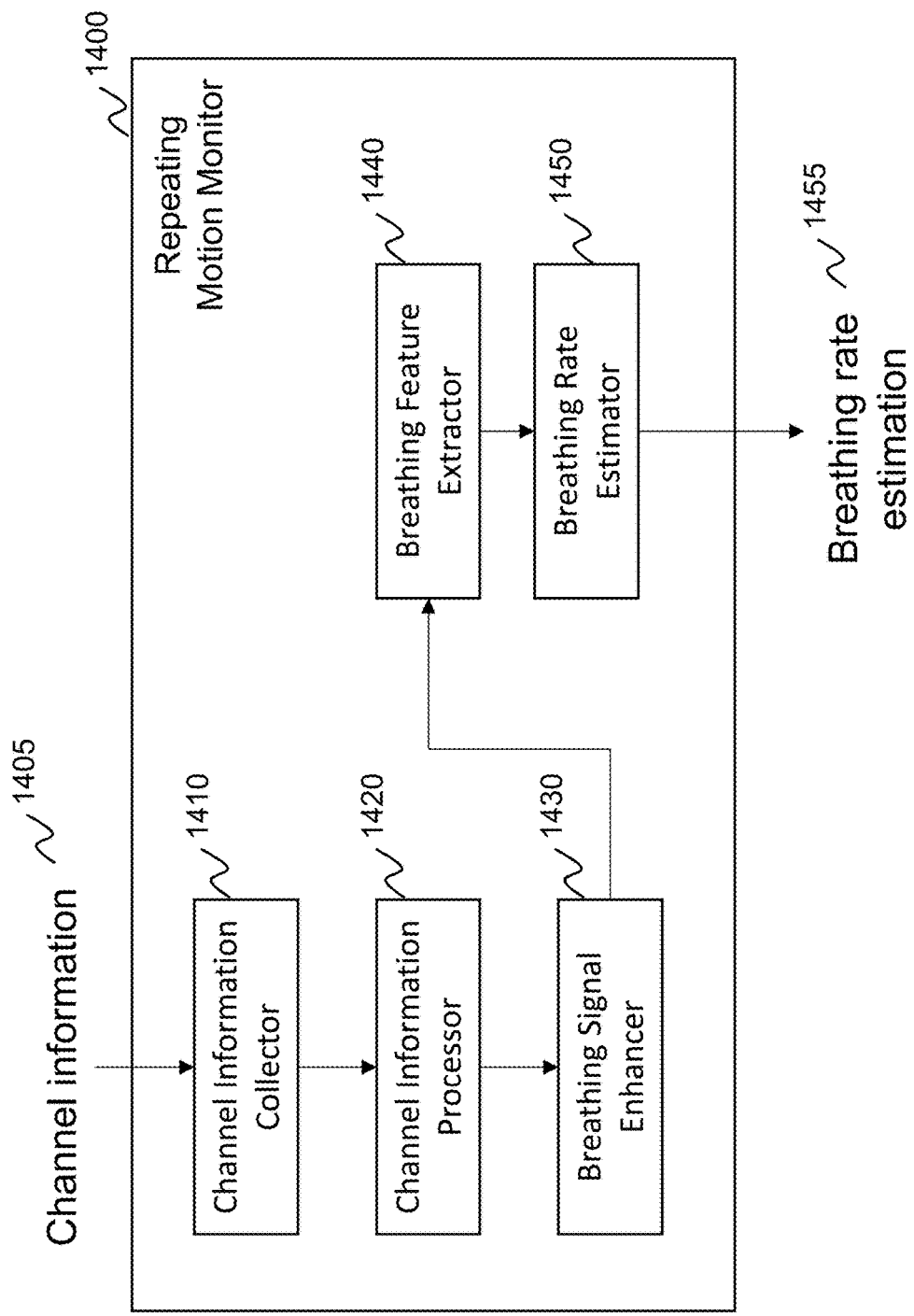
FIG. 14 illustrates an exemplary block diagram of a repeating motion monitor, according to one embodiment of the present teaching.

FIG. 14 illustrates an exemplary block diagram of a repeating motion monitor 1400, according to one embodiment of the present teaching. In one embodiment, the repeating motion monitor 1400 is in a system for monitoring a repeating motion of an object in a venue. According to various embodiments, the object may be a life (e.g. a human, a pet, an animal, etc.), a device (e.g. a fan, a machine, etc.), or a land; the repeating motion may represent: breathing, heartbeat, a periodic hand gesture, a periodic gait, a rotation, a vibration, or an earthquake; and the system can monitor periodic characteristics of the motion, e.g. a rate or frequency of the repeating motion. In one embodiment, the system comprises a transmitter (e.g. the transmitter 110), a receiver (e.g. the receiver 120) and the repeating motion monitor 1400 that is coupled to at least one of: the transmitter 110, the receiver 120, an additional transmitter, an additional receiver, a cloud server, a fog server, a local server, and an edge server.

In one embodiment, the transmitter is located at a first position in the venue and configured for transmitting a wireless signal through a wireless multipath channel impacted by a repeating motion of an object in the venue. The receiver is located at a second position in the venue and configured for: receiving the wireless signal through the wireless multipath channel impacted by the repeating motion of the object in the venue, and obtaining a time series of channel information (CI) of the wireless multipath channel based on the wireless signal. The wireless signal may be a probe signal or an acknowledge (ACK) signal in response to a probe signal.

The repeating motion monitor 1400 is configured for monitoring a periodic characteristics of the repeating motion of the object based on the time series of CI. Each CI comprises N1 components, wherein N1 is an integer greater than 1. The repeating motion monitor may be further configured for: decomposing the time series of CI into N1 component time series, each respective component time series comprising a respective one of the N1 components of each CI, computing N1 component-feature time series based on the N1 component time series, each respective component-feature time series comprises a feature of the respective component of each CI, associating a current periodic characteristic of the repeating motion of the object with a current sliding time window, compute N1 component sliding functions, each respective component sliding function being a respective transform of a respective component-feature time series in the current sliding time window, and monitoring the current periodic characteristics of the repeating motion of the object based on at least one of: the N1 component sliding functions, and a combined sliding function computed based on the N1 component sliding functions.

In one embodiment, the sliding time window for the repeating motion monitor 1400 to monitor the periodic characteristics can be very short, e.g. 10 to 15 seconds. The sliding window length is related to the initial setup and/or waiting time for the repeating motion monitor 1400. A shorter sliding window means a shorter initial setup time, which means a better user experience, since the user does not need to maintain a same breathing rate in a long sliding time window for the repeating motion monitor 1400 to capture the breathing.

In one embodiment, each CI comprises at least one of: a channel frequency response (CFR) comprising N1 complex frequency components each of which is associated with a frequency, a channel impulse response (CIR) comprising N1 complex time components each of which is associated with a time, and a decomposition with N1 components each of which is associated with an index. The feature comprises at least one of: phase, magnitude, real component, purely imaginary component, mean, mode, median, expected value, variance, square, cube, power, polynomial, exponential, derivative, and integration. The respective transform comprises at least one of: Fourier transform, Sine transform, Cosine transform, Laplace transform, wavelet transform, Hadamard transform, Hilbert transform, slant transform, sparse transform, graph-based transform, lowpass filtering, highpass filtering, bandpass filtering, finite-impulse-response (FIR) filtering, infinite-impulse-response (IIR) filtering, linear filtering, convolution, nonlinear function, statistical function, mean function, variance function, autocorrelation function (ACF), moment generating function, nonlinear filtering, signal processing, graph-based processing, particle filtering, integration, differentiation, first order derivative, second order derivative, high order derivative, neural network, learning network, feature extraction, denoising, smoothing, signal enhancement, coding, encryption, mapping, remapping, vector quantization, autoregressive (AR) filtering, moving average (MA) filtering, autoregressive moving average (ARMA) filtering, median filtering, mode filtering, ordered statistics filtering, percentile filtering, eigen-decomposition, singular-value decomposition, orthogonal decomposition, sparse approximation, principle component analysis (PCA), and independent component analysis (ICA), projection, decomposition, sampling, re-sampling, random sampling, down-sampling, up-sampling, interpolation, and extrapolation. The combined sliding function comprises at least one of: arithmetic mean, geometric mean, harmonic mean, power mean, f-mean, linear combination, weighted mean, weighted arithmetic mean, weighted geometric mean, weighted harmonic mean, weighted truncated mean, interquartile mean, and generalized mean, of the N1 component functions.

In one embodiment, as shown in FIG. 14, the repeating motion monitor 1400 includes a channel information collector 1410, a channel information processor 1420, a breathing signal enhancer 1430, a breathing feature extractor 1440, and a breathing rate estimator 1450. The channel information collector 1410 in this example collects time series of channel information (CI) 1405, e.g. channel state information or channel frequency response, which may be the channel information 125 generated by the receiver 120. According to various embodiments, the repeating motion monitor 1400 can not only monitor and estimate breathing rate, but also characteristics of any other repeating motions. In that case, the breathing signal enhancer 1430 is a repeating signal enhancer; the breathing feature extractor 1440 is a repetition feature extractor; the breathing rate estimator 1450 is a repetition rate estimator.

The channel information processor 1420 in this example processes the time series of CI by e.g. decomposing the time series of CI into N1 component time series, each respective component time series comprising a respective one of the N1 components of each CI, computing N1 component-feature time series based on the N1 component time series, each respective component-feature time series comprises a feature of the respective component of each CI, associating a current periodic characteristic of the repeating motion of the object with a current sliding time window, and computing N1 component sliding functions, each respective component sliding function being a respective transform of a respective component-feature time series in the current sliding time window. The channel information processor 1420 may further identify and remove any unallowed feature from the at least one feature. According to various embodiments, a feature outside an allowable range is identified as an unallowed feature, a feature in the allowable range is identified as an unallowed feature when it is greater than an adaptive threshold that is computed adaptively based on an adaptive background noise floor, and the adaptive background noise floor is computed based on at least one feature outside the allowable range.

In one embodiment, the breathing signal enhancer 1430 is configured for computing at least one of: N1 component frequency functions based on a frequency transform of each of the N1 respective component sliding functions, and a combined frequency function based on the frequency transform of the combined sliding function. The breathing feature extractor 1440 is configured for computing at least one feature of at least one of: the N1 component frequency functions, and the combined frequency function. The breathing rate estimator 1450 is configured for monitoring at least one of: the current periodic characteristics of the repeating motion of the object, and a current periodic characteristics of an additional repeating motion of an additional object in the venue, based on the at least one feature.

In one embodiment, the breathing feature extractor 1440 is configured for computing at least one feature of at least one of: the combined sliding function, and each of the N1 component sliding functions, wherein the at least one feature comprises at least one of: an extremum, a local maximum, a local minimum, a zero-crossing, a local maximum derivative, a local maximum high-order derivative, a local minimum derivative, a local minimum high-order derivative, a local zero derivative, a positive quantity, a negative quantity, a significant quantity, a positive maximum, a positive minimum, a negative maximum, a negative minimum, a first maximum, a first minimum, a second maximum, a second minimum, an N-th maximum, an N-th minimum, a significant maximum, a significant minimum, a significant derivative, and a significant high-order derivative. The breathing rate estimator 1450 is configured for monitoring the current periodic motion of the object based on at least one of: the at least one feature of at least one of: the combined sliding function and each of the N1 component sliding functions, and at least one domain value associated with the at least one feature of at least one of: the combined sliding function and each of the N1 component sliding functions.

In another embodiment, the breathing feature extractor 1440 is configured for computing at least one dominant periodic feature of each of the N1 component-feature time series in the current sliding time window, wherein the at least one dominant periodic feature comprises at least one of: a spectral extremum, a local spectral maximum, a local spectral minimum, a spectral zero-crossing, a local maximum spectral derivative, a local maximum spectral high-order derivative, a local minimum spectral derivative, a local minimum spectral high-order derivative, a local zero spectral derivative, a positive spectral quantity, a negative spectral quantity, a significant spectral quantity, a positive spectral maximum, a positive spectral minimum, a negative spectral maximum, a negative spectral minimum, a first spectral maximum, a first spectral minimum, a second spectral maximum, a second spectral minimum, an N-th spectral maximum, an N-th spectral minimum, a significant spectral maximum, a significant spectral minimum, a significant spectral derivative, and a significant spectral high-order derivative. The breathing rate estimator 1450 is configured for monitoring the current periodic characteristics of the repeating motion of the object based on at least one of: the dominant periodic features of the N1 component-feature time series in the current sliding time window, and at least one combined dominant periodic feature based on the dominant periodic features of the N1 component-feature time series in the current sliding time window.

In yet another embodiment, the breathing feature extractor 1440 is configured for computing at least one dominant periodic feature of each of the N1 component time series in the current sliding time window, wherein the at least one dominant periodic feature comprises at least one of: a spectral extremum, a local spectral maximum, a local spectral minimum, a spectral zero-crossing, a local maximum spectral derivative, a local maximum spectral high-order derivative, a local minimum spectral derivative, a local minimum spectral high-order derivative, a local zero spectral derivative, a positive spectral quantity, a negative spectral quantity, a significant spectral quantity, a positive spectral maximum, a positive spectral minimum, a negative spectral maximum, a negative spectral minimum, a first spectral maximum, a first spectral minimum, a second spectral maximum, a second spectral minimum, an N-th spectral maximum, an N-th spectral minimum, a significant spectral maximum, a significant spectral minimum, a significant spectral derivative, a significant spectral high-order derivative, and another periodic feature. The breathing rate estimator 1450 is configured for monitoring the periodic characteristics of the repeating motion of the object based on at least one of: the dominant periodic features of the N1 component time series in the current sliding time window, and at least one combined dominant periodic feature based on the dominant periodic features of the N1 component time series in the current sliding time window.

The breathing rate estimator 1450 generates an estimation of a periodic characteristics (e.g. a breathing rate estimation 1455) of the repeating motion of the object. In one embodiment, the breathing rate estimator 1450 may further compute at least one analytics based on the periodic characteristics of the repeating motion of the object, and transmit information of the periodic characteristics of the repeating motion of the object to a user interface. The user interface may be configured for presenting a summary of the periodic characteristics of the repeating motion of the object based on the transmitted information. The summary may comprise at least one of: an analytics, a selected time window, a subsampling, a transform, a projection, etc. The presenting may comprise presenting at least one of: a monthly view, a weekly view, a daily view, a simplified view, a detailed view, a cross-sectional view, a small form-factor view, a large form-factor view, a color-coded view, a comparative view, a summary view, an animation, a web view, a voice announcement, and another presentation related to the periodic characteristics of the repeating motion.

In one embodiment, the breathing rate estimator 1450 is configured for: processing the periodic characteristics of the repeating motion of the object; computing a time function based on the periodic characteristics of the repeating motion of the object; analyzing at least one of: the periodic characteristics of the repeating motion of the object, and the time function; and computing at least one analytics based on at least one of: the periodic characteristics of the repeating motion of the object, and the time function. The processing may comprise at least one of: doing nothing, zero-padding, time-domain processing, frequency domain processing, time-frequency processing, spatially varying processing, temporally varying processing, adaptive processing, denoising, smoothing, conditioning, enhancement, restoration, feature extraction, weighted averaging, averaging over antenna links, averaging over selected frequency, averaging over selected components, quantization, vector quantization, filtering, linear filtering, nonlinear filtering, low-pass filtering, bandpass filtering, high-pass filtering, median filtering, ranked filtering, quartile filtering, percentile filtering, mode filtering, linear filtering, nonlinear filtering, finite impulse response (FIR) filtering, infinite impulse response (IIR) filtering, moving average (MA) filtering, auto-regressive (AR) filtering, auto-regressive moving average (ARMA) filtering, thresholding, soft thresholding, hard thresholding, soft clipping, local maximization, local minimization, optimization of a cost function, neural network, machine learning, supervised learning, unsupervised learning, semi-supervised learning, transformation, mapping, transform, inverse transform, integer transform, power-of-2 transform, real transform, floating-point transform, fixed-point transform, complex transform, fast transform, Fourier transform, Laplace transform, Hadamard transform, Hilbert transform, sine transform, cosine transform, triangular transform, wavelet transform, transformation, decomposition, selective filtering, adaptive filtering, derivative, first order derivative, second order derivative, higher order derivative, integration, zero crossing, indicator function, absolute conversion, convolution, multiplication, division, another transform, another processing, another filter, another function, normalization, temporal normalization, frequency normalization, magnitude correction, phase correction, phase cleaning, cleaning a phase associated with the channel information, normalizing components associated with the channel information, cleaning a phase of frequency components of the channel information, normalizing the frequency components, re-sampling, labeling, tagging, training, sorting, grouping, folding, thresholding, matched filtering, spectral analysis, clustering, quantization, vector quantization, time correction, time base correction, time stamp correction, sampling rate up-conversion/down-conversion, upsampling, interpolation, intrapolation, extrapolation, subsampling, decimation, compression, expansion, encryption decryption, coding, storing, retrieving, transmitting, receiving, representing, merging, combining, splitting, tracking, monitoring, projection, orthogonal projection, non-orthogonal projection, over-complete projection, decomposition, eigen-decomposition, principal component analysis (PCA), sparse approximation, matching pursuit, and another operation. Any thresholds may be pre-determined, adaptively determined and/or determined by a finite state machine. The adaptive determination may be based on time, space, location, antenna, path, link, state, battery life, remaining battery life, available power, available computational resources, available network bandwidth, etc.

In another embodiment, the breathing rate estimator 1450 is configured for: estimating a missing periodic characteristics of the repeating motion of the object based on at least one of: available periodic characteristics of the repeating motion of the object computed based on the time series of CI, a different characteristics computed based on the time series of CI, and a different characteristics computed based on a different time series of CI of the wireless multipath channel.

In yet another embodiment, the breathing rate estimator 1450 is configured for: computing a trend function by lowpass filtering a time function of the periodic characteristics of the repeated motion of the object; analyzing at least one of: the time function, the trend function, and a detrended function computed by subtracting the trend function from the time function of the periodic characteristics; and monitoring the repeating motion of the object based on at least one of: the time function, the trend function, and the detrended function.

The object may be a life (e.g. a human, a baby). The breathing rate estimator 1450 may be configured to monitor sleeping of the human. Various stages of sleeping including rapid-eye-movement (REM), non-REM, awake, asleep, interruption may be identified. At least one analytics associated with the sleeping stages may be computed. Analytics associated with sleeping quality may be computed.

The object may be a device. The breathing rate estimator 1450 may be configured to monitor a repeated motion such as vibration, rotation, back-and-forth action, and/or repeated machine action. Analytics associated with normal and/or abnormal operation of the device may be computed. Analytics associated with location of machine parts in the repeated cycle may be computed.

The object may be land. The breathing rate estimator 1450 may be configured to monitor signs of earthquakes, aftershocks, shaking, and/or vibration.

In one embodiment, the system can measure more than one breathing rate simultaneously. In this case, the repeating motion monitor 1400 is further configured for: monitoring an additional periodic characteristics of an additional repeating motion of an additional object contemporaneously based on the time series of CI, wherein the wireless multipath channel is further impacted by the additional repeating motion of the additional object in the venue. The at least one feature comprises: a first feature associated with the periodic characteristics of the repeating motion of the object, and a second feature associated with the periodic characteristics of the additional repeating motion of the additional object. The periodic characteristics of the repeating motion of the object and the periodic characteristics of the additional repeating motion of the additional object are monitored contemporaneously based on the first feature and the second feature.

In one embodiment, the breathing rate is monitored in a series of overlapping time window. In this case, the repeating motion of the object is locally repeating such that, in each of a series of overlapping time windows, the locally repeating motion resembles a periodic motion; and the periodic characteristics of the locally repeating motion of the object is monitored in each of the series of overlapping time window.

In another embodiment, the system can perform not only the breathing rate detection and estimation, but also other detections and estimations for, e.g. fall-down detection, tracking monitoring, etc. In this case, the repeating motion monitor 1400 is further configured for: performing a joint analysis on the periodic characteristics of the repeating motion of the object and at least one of: a different characteristics computed based on the time series of CI, and a different characteristics computed based on a different time series of CI of the wireless multipath channel; and computing at least one joint analytics based on the joint analysis.

Figure 15:
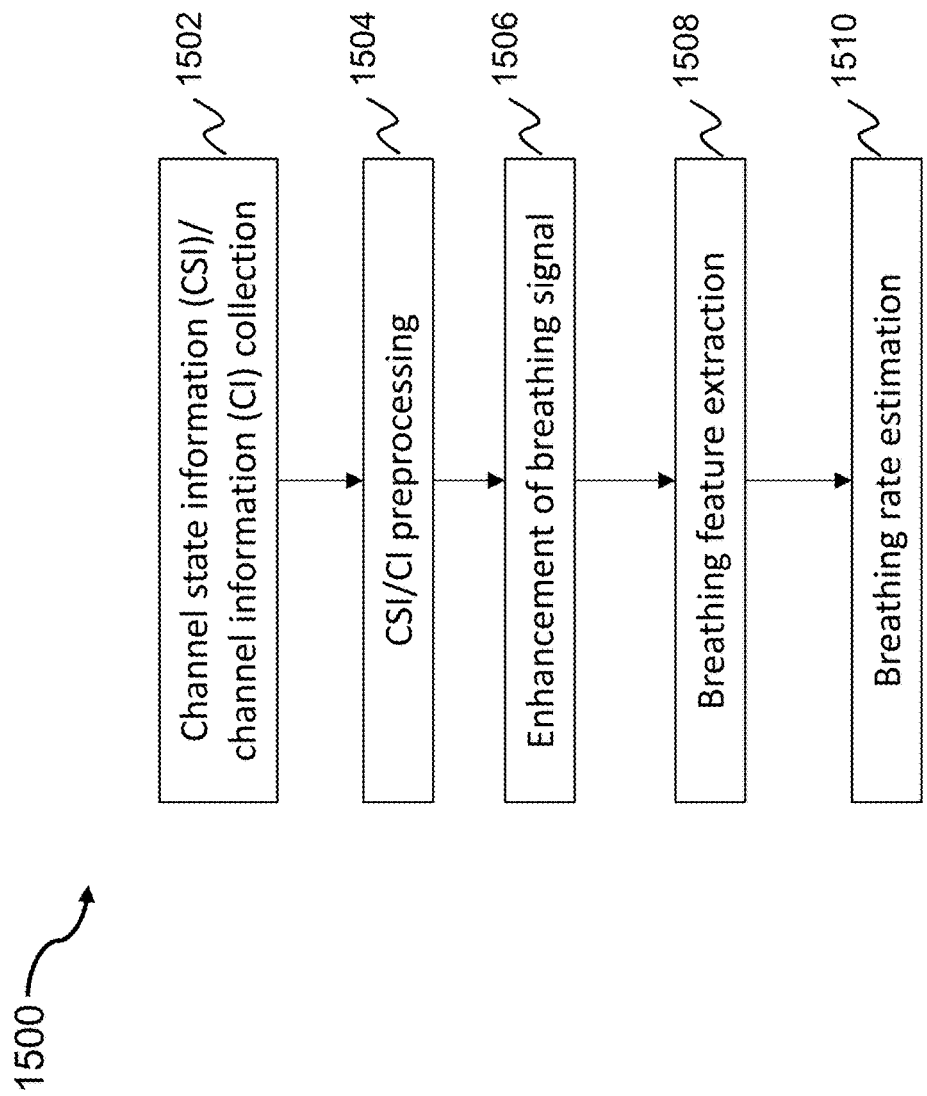
FIG. 15 illustrates a flowchart of an exemplary method for estimating and monitoring repetition rate (e.g. breathing rate), according to one embodiment of the present teaching.

FIG. 15 illustrates a flowchart of an exemplary method 1500 for estimating and monitoring a vital sign (e.g. breathing rate, heart rate), according to one embodiment of the present teaching. First, channel state information (CSI) or channel information (CI, e.g. CSI) may be obtained at operatoin 1502 by channel estimation after a radio receiver (e.g. wireless, RF, WiFi, LTE, UWB, etc) receives a wireless signal (e.g. a channel probing radio signal, a reply signal, an acknowledgement signal, a data signal, or a control signal) from a radio transmitter. The CSI/CI is preprocessed at operatoin 1504, e.g., to remove noise and/or to calculate some feature function (e.g. autocorrelation function (ACF)) from the breathing signal. Since breathing signal may be very weak, the received signal may be enhanced at operatoin 1506 to boost the signal-to-noise ratio (SNR) through some operation, e.g., maximal ratio combining (MRC). The ACF may exhibit a periodic behavior since breathing is a periodic process, and features about breathing can be extracted at operation 1508 from the ACF, e.g., detecting a (first) local maximum from the ACF. The time lag of the first local maximum correspond to the period T of breathing, and then the breathing rate estimation can be obtained at operation 1510, e.g. by 60/T breath per minute.

Figure 16:
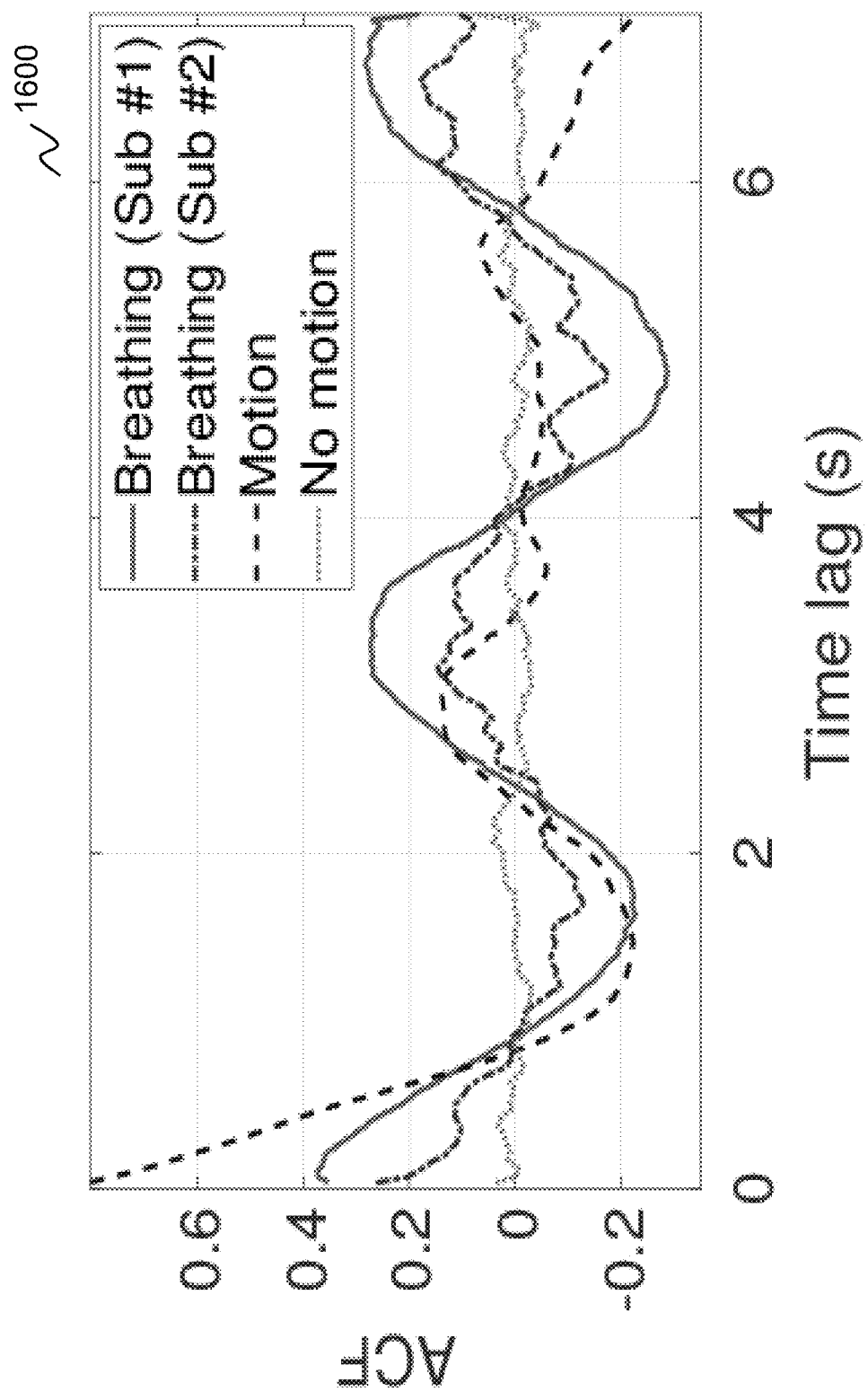
FIG. 16 illustrates exemplary autocorrelation functions of the received signals under different scenarios, according to one embodiment of the present teaching.

FIG. 16 illustrates exemplary autocorrelation functions 1600 of the received signals under different scenarios, according to one embodiment of the present teaching. As shown in FIG. 16, when there is a breathing signal, the ACF will exhibit a definite peak at a certain delay (although the peak value may differ over different subcarriers), contributed by the periodic breathing motions. On the contrary, no certain peaks can be observed on any subcarrier when there is no breathing (i.e., no periodic motions). In principle a time delay slightly longer than one breathing cycle (e.g., 5 to 7 seconds) is sufficient to pick up the first breathing rate and later on instantaneous estimates can be produced every one second.

Motion Statistics:

In prior to breathing estimation, a key step is to examine whether there exists detectable breathing signal (i.e., whether breathing exists without extra big motions). As mentioned previously, breathing will easily be buried in other large body motions, and should not be estimated if there is none. One can also investigate the property of the ACF for this purpose since, in addition to breathing, the calculated ACF actually offers indicators for detection of arbitrary motions.

Figure 17:
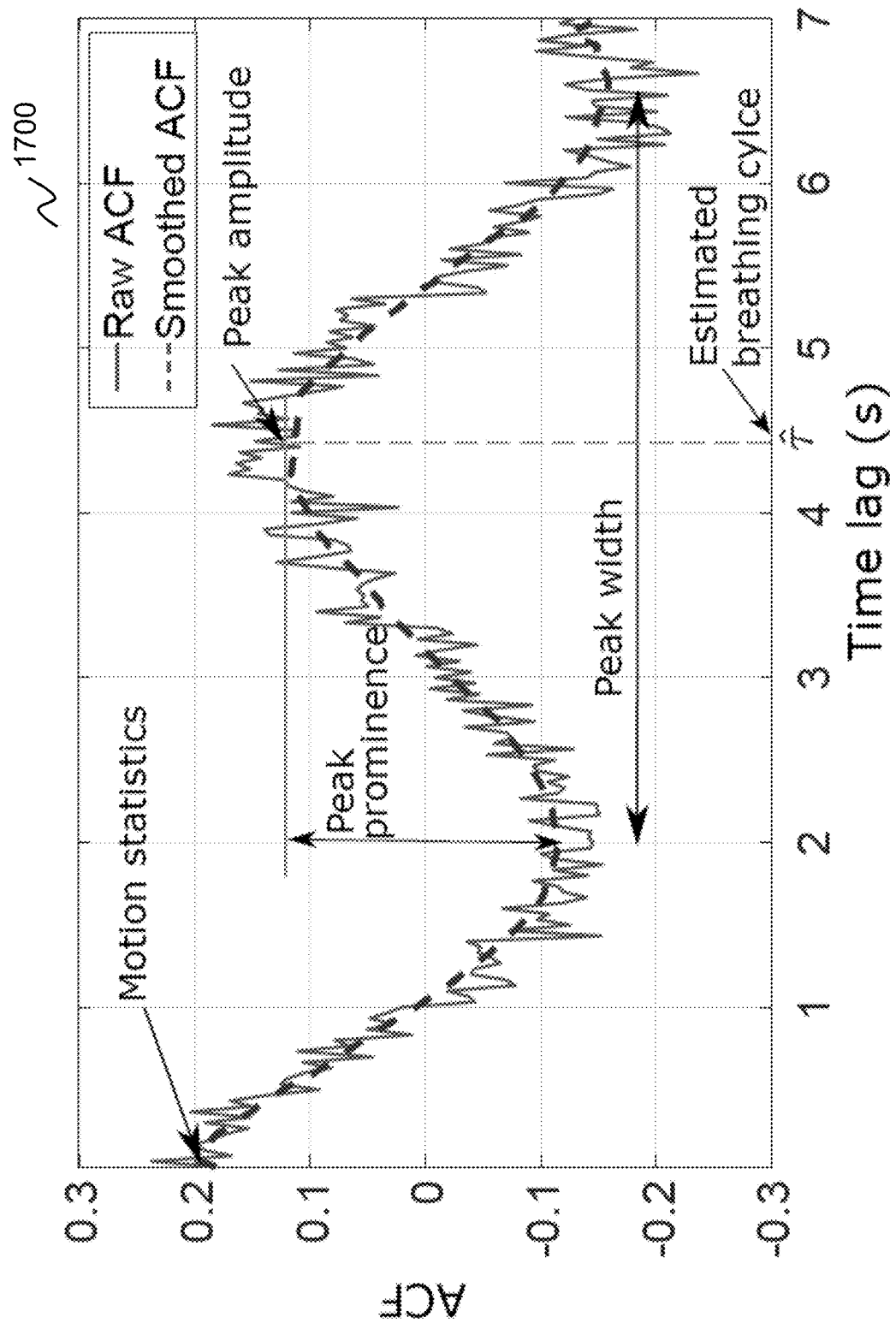
FIG. 17 illustrates exemplary features extracted from the derived autocorrelation functions for breathing detection and estimation, according to one embodiment of the present teaching.

Breathing Detection and Estimation:

Based on the calculated ACF and its inherent characteristics, the system first detects the presence and absence of breathing and, if presented, then estimates the breathing rate, accurately and instantaneously. FIG. 17 illustrates exemplary features 1700 extracted from the derived autocorrelation functions for breathing detection and estimation, according to one embodiment of the present teaching. As shown in FIG. 17, for a subcarrier with frequency f, one can extract several features from $\hat{\rho}_G(\tau, f)$ for breathing detection, in addition to the motion statistics. The first feature is Peak Prominence, which is the vertical distance between the peak value and the largest height of the adjacent valleys, which measures the likelihood of the existence of the peak. The second feature is Peak Width, which is the horizontal distance between the two adjacent valleys, which also measures the likelihood of the existence of the peak. The third feature is Peak Amplitude, which is the height of the peak, which measures the amplitude of the ACF of the breathing signal and will be comparable to the value of motion statistic in presence of only breathing motion. The fourth feature is Motion Interference Ratio, which is the ratio between the motion statistics and peak amplitude, which measures degree of the interference of the non-breathing motion, such as body movements, walking, standing up, typing keyboard, etc., in the environment. The fifth feature is Peak Location, which is the horizontal distance between the origin and the peak (i.e., time lags), which measures the breathing cycle. Other features may be computed.

In general, the larger the motion statistics, peak prominence, peak width, peak amplitude and the smaller the motion interference ratio, the more likely for the presence of the breathing signal. In one embodiment, the above features are jointly fused to claim the existence of breathing signal and the corresponding breathing rate. Once there is a breathing signal, the breathing rate can be estimated as BR=60/$\hat{\tau}$ breath per minute, where $\hat{\tau}$ is the location (i.e., time lags) of the first dominant peak of $\hat{\rho}_G(\tau, f)$.

In practice, the SNR of the breathing signal on each subcarrier modulated by minute breathing motions is very low, especially when the person being monitored is far away from the link, covered by quilts, or behind the wall, resulting in limited coverage and vulnerable estimation that prevents the applications of the existing RF-based approaches. Previous approaches attempt to select a best subcarrier among others, or to average over all to improve breathing signal do not produce reliable, not to mention optimal results.

To boost the breathing SNR, the system may combine the breathing signals measured on different subcarriers in the optimal way. In one embodiment, the disclosed design is based on Maximal Ratio Combining (MRC), a classical diversity combining method in telecommunications that maximize signal SNR by optimally combining received signals on multiple antennas.

MRC on Breathing Signal.

In the context of breathing estimation with CSI, the breathing signal b(t) denotes a periodic stationary breathing signal with zero mean, which is related to the movement of the chest and abdomen, and is measured by multiple subcarriers. Let g(f) and $\Delta t_f$ stand for the gain and the random initial phase of the breathing signal measured at the frequency f, respectively. The SNR of the breathing signal, denoted as $\gamma(f)$, measured on subcarrier with frequency f at time t is defined as $$\gamma(f) = \frac{\mathbb{E}[(g(f)b(t-\Delta t_f))^2]}{\mathbb{E}[\varepsilon^2(t,f)]} = \frac{g^2(f)\mathbb{E}(b^2(t-\Delta t_f))}{\sigma^2(f)}, \quad (13)$$

where $\mathbb{E}[\bullet]$ stands for the expectation operator and $\varepsilon(t, f)$ is defined as the noise term. For convenience, the average power of the breathing signal b(t) is normalized to unit power by definition, that is, $\mathbb{E}[b^2(t)]=1$, and thus one can have $\gamma(f)=g^2(f)/\sigma^{-2}(f)$.

Defining $$k(f) \triangleq \frac{g^2(f)}{g^2(f)+\sigma^2(f)}$$

as the normalized channel gain, it can reflect the strength of total motion existing in the monitored area. The SNR of the ACF of each subcarrier can be estimated as $N\hat{k}^2(f)$, where N is the number of samples used in the estimation of the ACF. Then the weight can be set to $\hat{\rho}_G(\tau=1/F_s, f)$, the ACF of G(t, f), where G(t, f) is the power response (i.e., the square of the magnitude of the channel frequency response H(t, f) at time t and frequency/subcarrier f).

Figure 18:
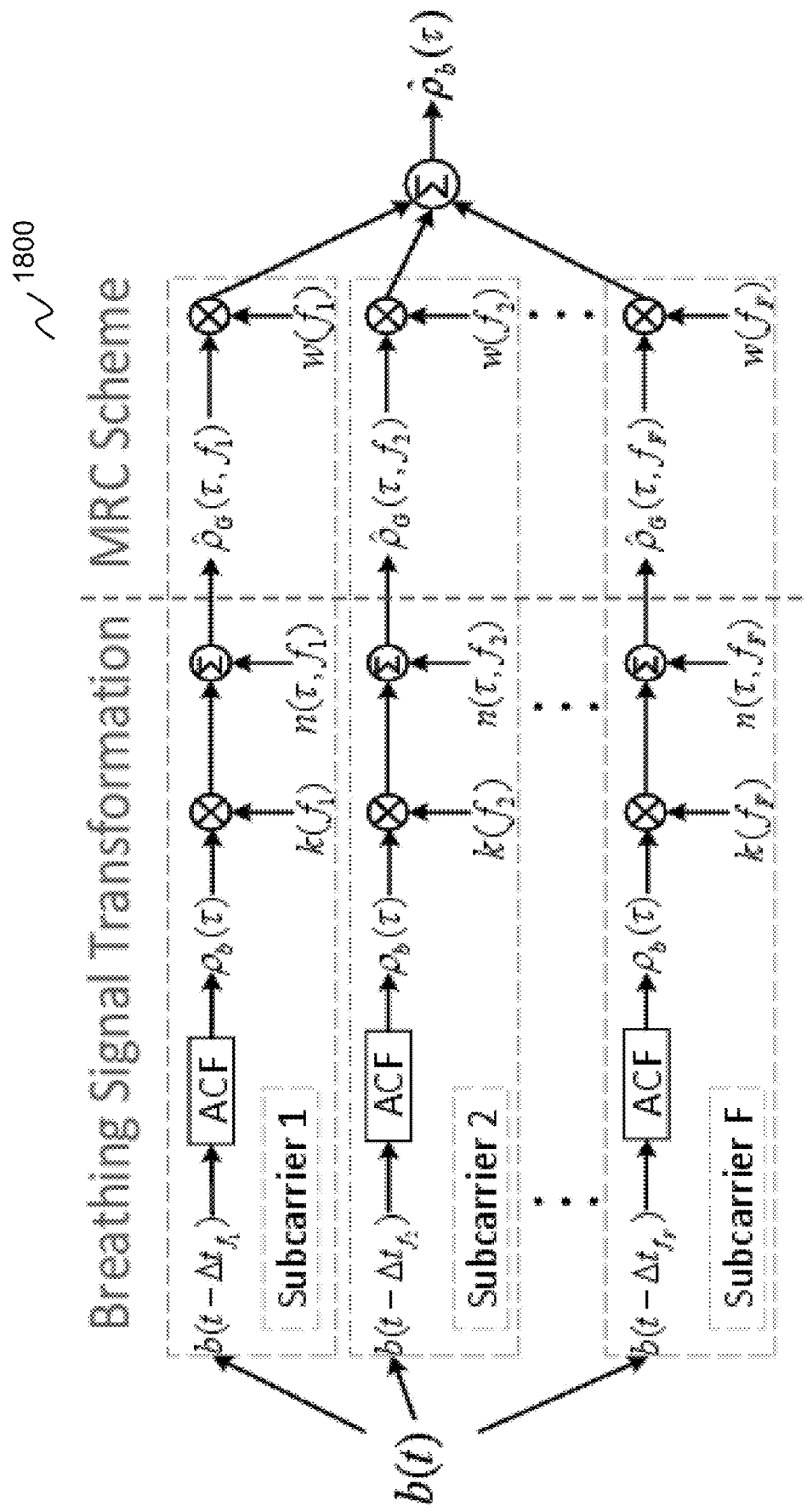
FIG. 18 illustrates an exemplary scheme for breathing signal extraction and maximization, according to one embodiment of the present teaching.

FIG. 18 illustrates an exemplary scheme 1800 for breathing signal extraction and maximization, according to one embodiment of the present teaching. The left part of the FIG. 18 shows the decomposition of the measured ACF of the channel power response when a person breathes normally in the monitored area, while the right part shows the MRC scheme for boosting the SNR of the ACF of the breathing signal.

Figure 19:
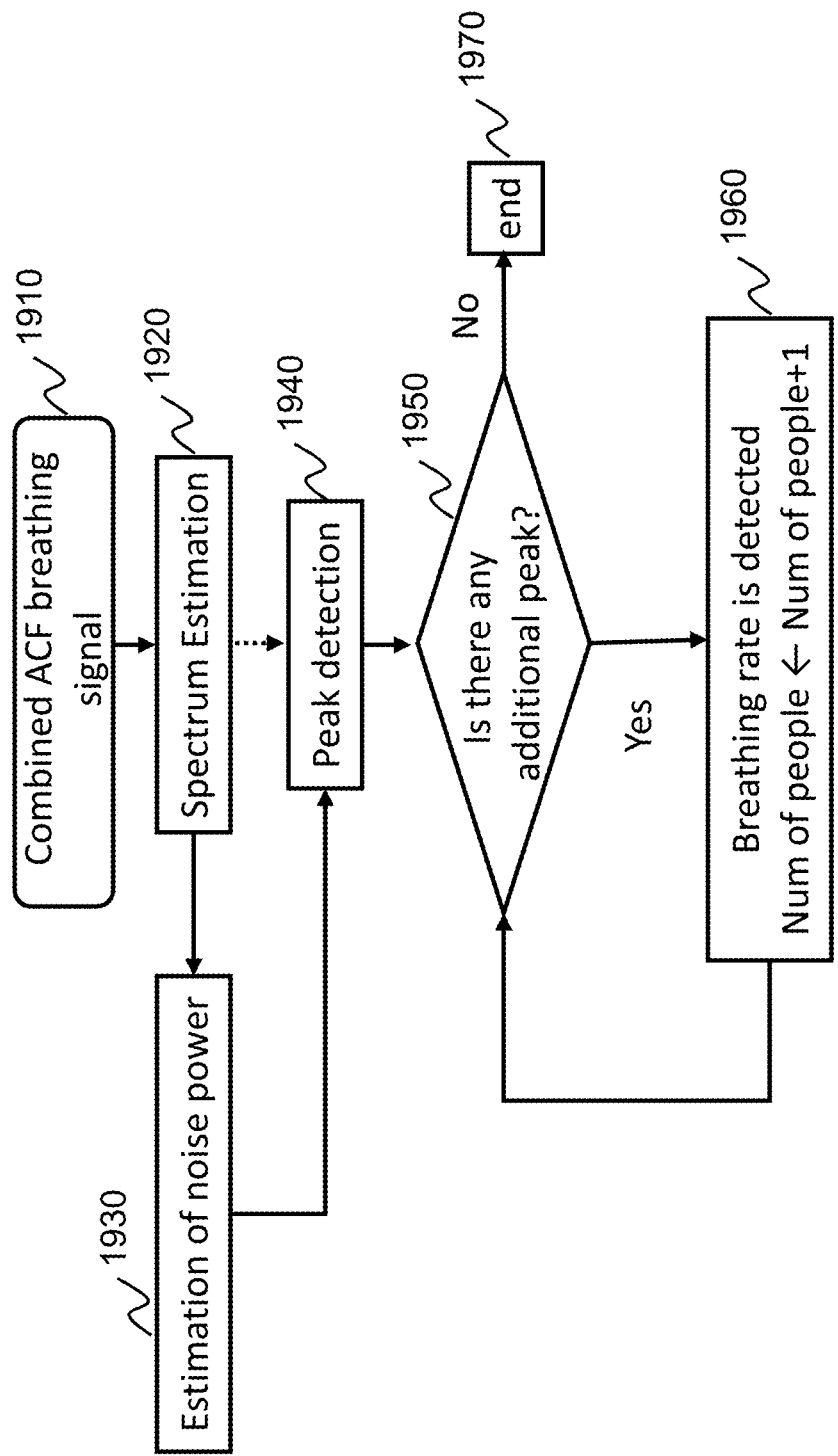
FIG. 19 illustrates an exemplary procedure of multi-person repetition rate (e.g. breathing rate) estimation, according to one embodiment of the present teaching.

FIG. 19 illustrates an exemplary procedure of multi-person breathing rate estimation, according to one embodiment of the present teaching. The input signal 1910 $\rho(\tau)$, where $0 \leq \tau \leq T$, denotes a combined ACF breathing signal, which is the ACF of the breathing signal after the MRC.

Spectrum estimation is performed at operation 1920 by calculating the power spectral density S(f), where $0 \leq f \leq F$, of the breathing signal $\rho(\tau)$. The spectrum estimation can be based on non-parametric methods, e.g., periodogram algorithm, or parametric spectrum estimators, e.g., MUSIC algorithm.

Estimation of noise power is performed at operation 1930. Let fl and fh denote the lower and upper bounds of the breathing rate of interests. The noise power n is estimated by calculating the average of the energy of the power spectral density outside the breathing range, i.e., $$n = \frac{1}{T+f_l-f_h}\sum_{f\leq f_l}S(f)+\sum_{f\geq f_h}S(f).$$

Peak detection is performed at operation 1940 by detecting all the peaks of S(f) within the range $fl \leq f \leq fh$, where a peak is defined as the point whose value is large than its neighbors. Let fi denote the i-th peak. In one embodiment, after the operation 1920, the process can go directly to the operation 1940 without perform the operation 1930.

At operation 1950, it is determined whether there is any additional peak. Each peak, e.g. the i-th peak, is examined, e.g. by comparing its value S(fi) with the estimated noise power n. If the difference is larger than a preset threshold $\eta$, i.e., $S(fi) \leq \eta$, then the peak is a valid peak and the corresponding breathing rate estimate is 60*fi. The process then goes to operation 1960 to update the number of people by adding 1 and the process goes back to operation 1950 to detect any additional peak. Otherwise, if the difference is not larger than a preset threshold, the peak is discarded. The number of people detected stays the same and the process stays at operation 1950 to detect any additional peak. When it is determined at operation 1950 that there is no additional peak, the process ends at operation 1970.

In one embodiment, the disclosed system may include a Type 1 device which is a Bot including a transmitter, a Type 2 device which is an Origin including a receiver, and the repeating motion monitor 1400. The receiver can extract a time series of CSI from a wireless signal and collect CSI for a slide window (about 10-15 sec). The repeating motion monitor 1400 can estimate the breathing rate based on the collected CSI. If the transmitter has M antennas and the receiver has N antennas, there are MN links. One CSI time series is obtained for each link. All MN links are used by the system to compute the breathing rate. The repeating motion monitor 1400 can be located in the cloud, or in the Origin or the Type 2 device for local computing. If there are K Bots, then there can be K instances of the repeating motion monitor 1400, each serving one Bot. The breathing results of each Bot may be displayed separately on a client app of a user smart device. Results of some or all Bots may be combined to give combined results. For 1 Bot with one antenna and 1 Origin with one antenna (K=1) scenario, there is only 1 link (M=N=1). Each CSI has N1 (e.g. about 128) frequency subcarriers (called components). As the phase of each subcarrier tends to be noisy, the repeating motion monitor 1400 can extract a noise-robust feature, e.g. magnitude square (i.e. square of magnitude, no phase) for each subcarrier. As each subcarrier is associated with a unique frequency, the feature is also associated with the same frequency. For a time series of CSI, the repeating motion monitor 1400 treats a respective feature associated with a respective frequency as a feature time series (called component-feature time series). Thus there are N1 component-feature time series. It computes autocorrelation function (ACF) for each component-feature time series (within the sliding window of about 10-15 sec). This is repeated for all frequency. The repeating motion monitor 1400 then computes an overall ACF as a weighted average of ACF of all frequency components. The weights are determined adaptively using an existing method called maximal ratio combining (MRC). Finally, the repeating motion monitor 1400 identifies the first positive significant local maximum. The time lag (T) associated with the identified local max gives the breathing rate (=1/T). When there are multiple persons, each person should have a corresponding peak in the overall ACF. But these peaks may be close to each other, which makes it hard to tell whether there is one peak or two or three, etc.

Figure 20:
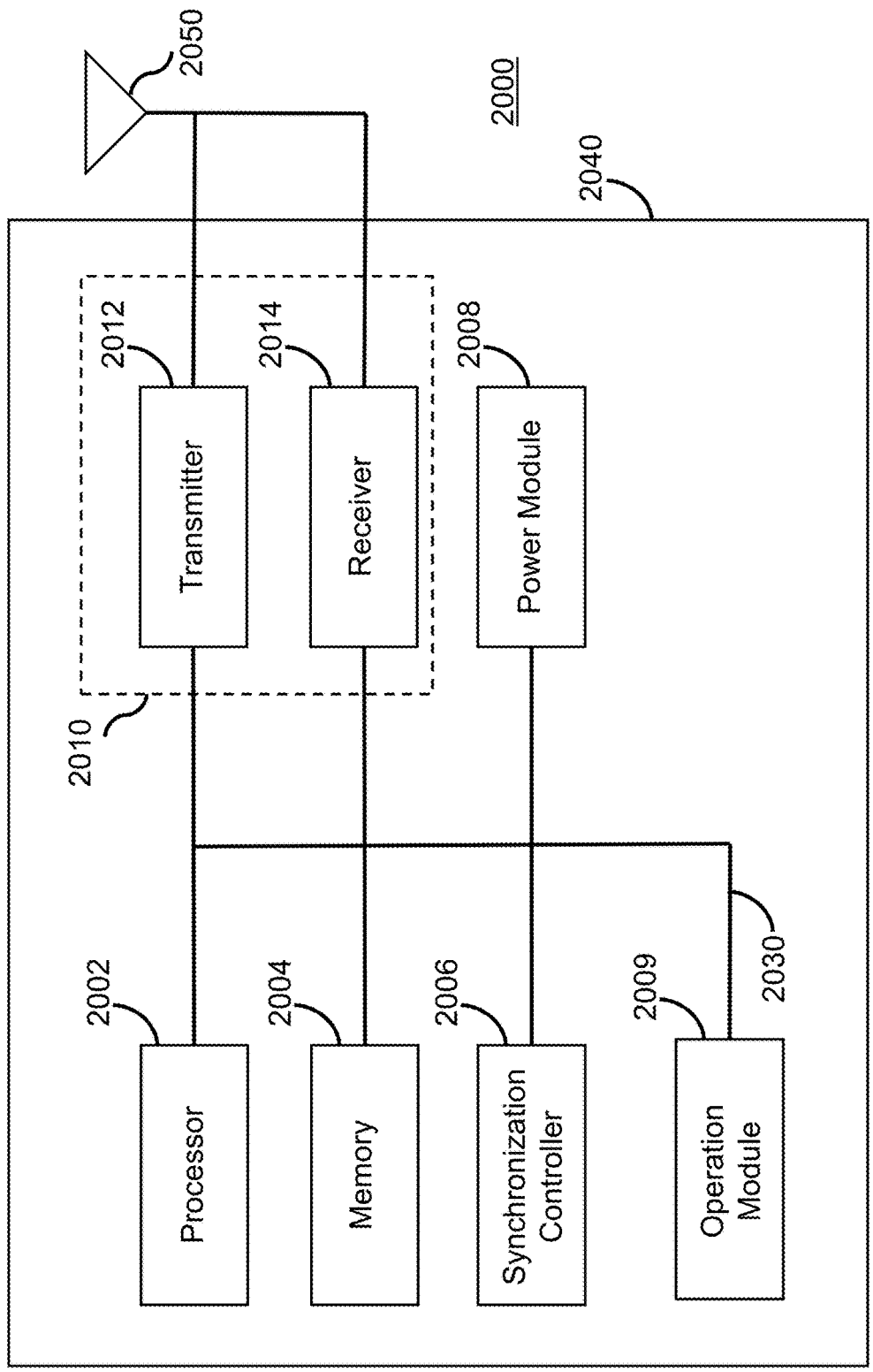
FIG. 20 illustrates an exemplary diagram of a device in a motion monitoring system, according to one embodiment of the present teaching.

FIG. 20 illustrates an exemplary diagram of a device 2000 in a motion monitoring system, according to one embodiment of the present teaching. The device 2000 is an example of a device that can be configured to implement the various methods described herein. According to various embodiments, the device may be: a Type 1 device which is a Bot including a transmitter, a Type 2 device which is an Origin including a receiver, the vital sign estimator 210, the system state controller 220, the repeating motion monitor 1400, and/or other components in FIGS. 1-19 and 21-26. As shown in FIG. 20, the device 2000 includes a housing 2040 containing a processor 2002, a memory 2004, a transceiver 2010 comprising a transmitter 2012 and a receiver 2014, a synchronization controller 2006, a power module 2008, and an operation module 2009.

In this embodiment, the processor 2002 controls the general operation of the device 2000 and can include one or more processing circuits or modules such as a central processing unit (CPU) and/or any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable circuits, devices and/or structures that can perform calculations or other manipulations of data.

The memory 2004, which can include both read-only memory (ROM) and random access memory (RAM), can provide instructions and data to the processor 2002. A portion of the memory 2004 can also include non-volatile random access memory (NVRAM). The processor 2002 typically performs logical and arithmetic operations based on program instructions stored within the memory 2004. The instructions (a.k.a., software) stored in the memory 2004 can be executed by the processor 2002 to perform the methods described herein. The processor 2002 and the memory 2004 together form a processing system that stores and executes software. As used herein, "software" means any type of instructions, whether referred to as software, firmware, middleware, microcode, etc. which can configure a machine or device to perform one or more desired functions or processes. Instructions can include code (e.g., in source code format, binary code format, executable code format, or any other suitable format of code). The instructions, when executed by the one or more processors, cause the processing system to perform the various functions described herein.

The transceiver 2010, which includes the transmitter 2012 and receiver 2014, allows the device 2000 to transmit and receive data to and from a remote device (e.g., an Origin or a Bot). An antenna 2050 is typically attached to the housing 2040 and electrically coupled to the transceiver 2010. In various embodiments, the device 2000 includes (not shown) multiple transmitters, multiple receivers, and multiple transceivers. In one embodiment, the antenna 2050 is replaced with a multi-antenna array 2050 that can form a plurality of beams each of which points in a distinct direction. The transmitter 2012 can be configured to wirelessly transmit signals having different types or functions, such signals being generated by the processor 2002. Similarly, the receiver 2014 is configured to receive wireless signals having different types or functions, and the processor 2002 is configured to process signals of a plurality of different types.

In one embodiment, the device 2000 may be a Bot or an Origin of a motion monitoring system. The motion monitoring system may comprise at least one Bot and at least one Origin. The synchronization controller 2006 in this example may be configured to control the operations of the device 2000 to be synchronized or un-synchronized with another device, e.g. another Origin or another Bot. In one embodiment, each of the device 2000 and other Bots or Origins in the system may transmit or receive the wireless signals individually and asynchronously.

The operation module 2009 in this example may perform one or more operations for vital sign detection and monitoring. The operation module 2009 may comprise one or more sub-modules to implement different methods disclosed herein. In one embodiment, the device 2000 may be the vital sign estimator 210 of a motion monitoring system, where the operation module 2009 includes one or more of the components shown in FIG. 3. In another embodiment, the device 2000 may be the repeating motion monitor 1400 of a motion monitoring system, where the operation module 2009 includes one or more of the components shown in FIG. 14.

The power module 2008 can include a power source such as one or more batteries, and a power regulator, to provide regulated power to each of the above-described modules in FIG. 20. In some embodiments, if the device 2000 is coupled to a dedicated external power source (e.g., a wall electrical outlet), the power module 2008 can include a transformer and a power regulator.

The various modules discussed above are coupled together by a bus system 2030. The bus system 2030 can include a data bus and, for example, a power bus, a control signal bus, and/or a status signal bus in addition to the data bus. It is understood that the modules of the device 2000 can be operatively coupled to one another using any suitable techniques and mediums.

Although a number of separate modules or components are illustrated in FIG. 20, persons of ordinary skill in the art will understand that one or more of the modules can be combined or commonly implemented. For example, the processor 2002 can implement not only the functionality described above with respect to the processor 2002, but also implement the functionality described above with respect to the operation module 2009. Conversely, each of the modules illustrated in FIG. 20 can be implemented using a plurality of separate components or elements.

In one embodiment, the present teaching discloses a method, apparatus, and a system for sleep monitoring. The disclosed method comprises: obtaining a time series of channel information (CI) of a wireless multipath channel using a processor, a memory communicatively coupled with the processor and a set of instructions stored in the memory, and monitoring the sleep-related motion of the user based on the time series of CI.

The time series of CI is extracted from a wireless signal transmitted between a Type 1 heterogeneous wireless device and a Type 2 heterogeneous wireless device in a venue through the wireless multipath channel. The wireless multipath channel is impacted by a sleep-related motion of a user in the venue.

Monitoring the sleep-related motion comprises monitoring at least one of the following of the user: sleep timings, sleep durations, sleep stages, sleep quality, sleep apnea, sleep problems, sleep disorders, breathing problems, gasping, choking, teeth-grinding, pause of sleep, absence of sleep, insomnia, restlessness during sleep, hypersomnia, parasomnia, day-time sleepiness, sleep locations, sleep-while-driving, sleep disruptions, nightmares, night terrors, sleep walking, REM sleep behavior disorder, Circadian rhythm disorder, non-24-hour sleep-wake disorder, periodic limb movement disorder, shift-work sleep disorder, narcolepsy, confusional arousals, sleep paralysis, another sleep-related condition, and/or another sleep-related behavior.

Sleep timings comprises timings of at least one of: go-to-bed, sleep-onset, wake-up, REM-onset, NREM-onset, onset of sleep stage transitions, sleep disorders, sleep problems, breathing problems, insomnia, hypersomnia, parasomnia, sleep hypnogram-related events, sleep disruptions, sleep apnea, snoring during sleep, sleeping-not-on-a-bed, daytime sleep, sleep-walking, sleep-related events, sleep-related condition, and/or, sleep-related behavior, etc.

Sleep stages comprises at least one of: wake-up, rapid-eye-movement (REM) and/or non-REM (NREM).

At least one of: a time function of breathing rate, and a time function of motion statistics, of the user may be computed based on the series of CI. If breathing is not detected at time t, the breathing rate at time t may be computed as zero. The sleep-related motion of the user may be monitored based on at least one of: the time function of breathing rate, and/or the time function of motion statistics, of the user.

At least one of: a time function of breathing ratio, and a time function of motion ratio, of the user may be computed based on the series of CI. The breathing ratio at time t may be computed as percentage of time when the time function of breathing rate is non-zero in a first time window comprising the time t. The motion ratio at time t may be computed as percentage of time when the time function of motion statistics is larger than a first threshold within a second time window comprising the time t. The sleep-related motion of the user may be monitored based on at least one of: the time function of breathing ratio, and/or the time function of motion ratio, of the user.

A sleep stage may be classified as "awake" if at least one of: the motion ratio is greater than a second threshold, and/or the breathing ratio is less than a third threshold. The sleep stage may be classified as "asleep" if at least one of: the motion ratio is less than the second threshold, and/or the breathing ratio is greater than the third threshold. The "asleep" stage may comprise at least one of: rapid-eye-movement (REM) stage, and/or non-REM (NREM) stage.

A breathing rate trend function may be computed by low-pass filtering the time function of breathing rate. A detrended breathing rate function may be computed by subtracting the breathing rate trend function from the time function of breathing rate. A time function of breathing rate variance may be computed by computing variance of the detrended breathing rate function within a sliding time window. The sleep-related motion of the user may be monitored based on the time function of breathing rate variance.

An average NREM breathing rate may be computed by identifying a peak of a histogram of the time function of breathing rate in "asleep" stage in an overnight period. (e.g. the whole night, or the whole night subtracting any "awake" periods). A time function of breathing rate deviation may be computed by computing a distance between the average NREM and a percentile of the breathing rate within a sliding time window. The sleep stage may be classified as at least one of: REM stage and/or NREM stage, based on the time function of breathing rate deviation.

A time function of breathing rate variance may be computed by computing variance of a detrended breathing rate function within a first sliding time window. A time function of breathing rate deviation may be computed by computing a distance between an average NREM and a percentile of the breathing rate within a second sliding time window. The sleep stage may be classified as at least one of: REM stage, and/or NREM stage, based on the time function of breathing rate variance and the time function of breathing rate deviation.

A classifier may be trained based on at least one of: breathing rate variance, and breathing rate deviation, using machine learning. The machine learning may comprise at least one of: supervised learning, unsupervised learning, semi-supervised learning, active learning, reinforcement learning, support vector machine, deep learning, feature learning, clustering, regression, and/or dimensionality reduction. The sleep stage may be classified as at least one of: REM stage, and/or NREM stage, based on the classifier.

A quantity related to the sleep-related motion of the user may be computed based on the time series of CI. The sleep-related motion of the user may be monitored based on the quantity.

The quantity may comprise at least one of: the time the user goes to bed, the time the user gets out of bed, the sleep onset time, total time it takes the user to fall asleep, the wake up time, sleep disruption time, number of sleep disruption period, mean disruption duration, variance of disruption duration, total time in bed, total time the user is asleep, time periods of REM, time periods of NREM, time periods of awake, total time of REM, total time of NREM, number of REM periods, number of NREM periods, time of toss and turn in bed, duration of tossing and turning, hypnogram, periods of apnea, periods of snore, total duration of apnea, number of apnea periods, average duration of apnea period, periods of breathing problems, sleep quality score, daytime sleep, time periods of daytime sleep, total duration of daytime sleep, number of period of daytime sleep, average duration of period of daytime sleep, and another quantity.

Figure 21:
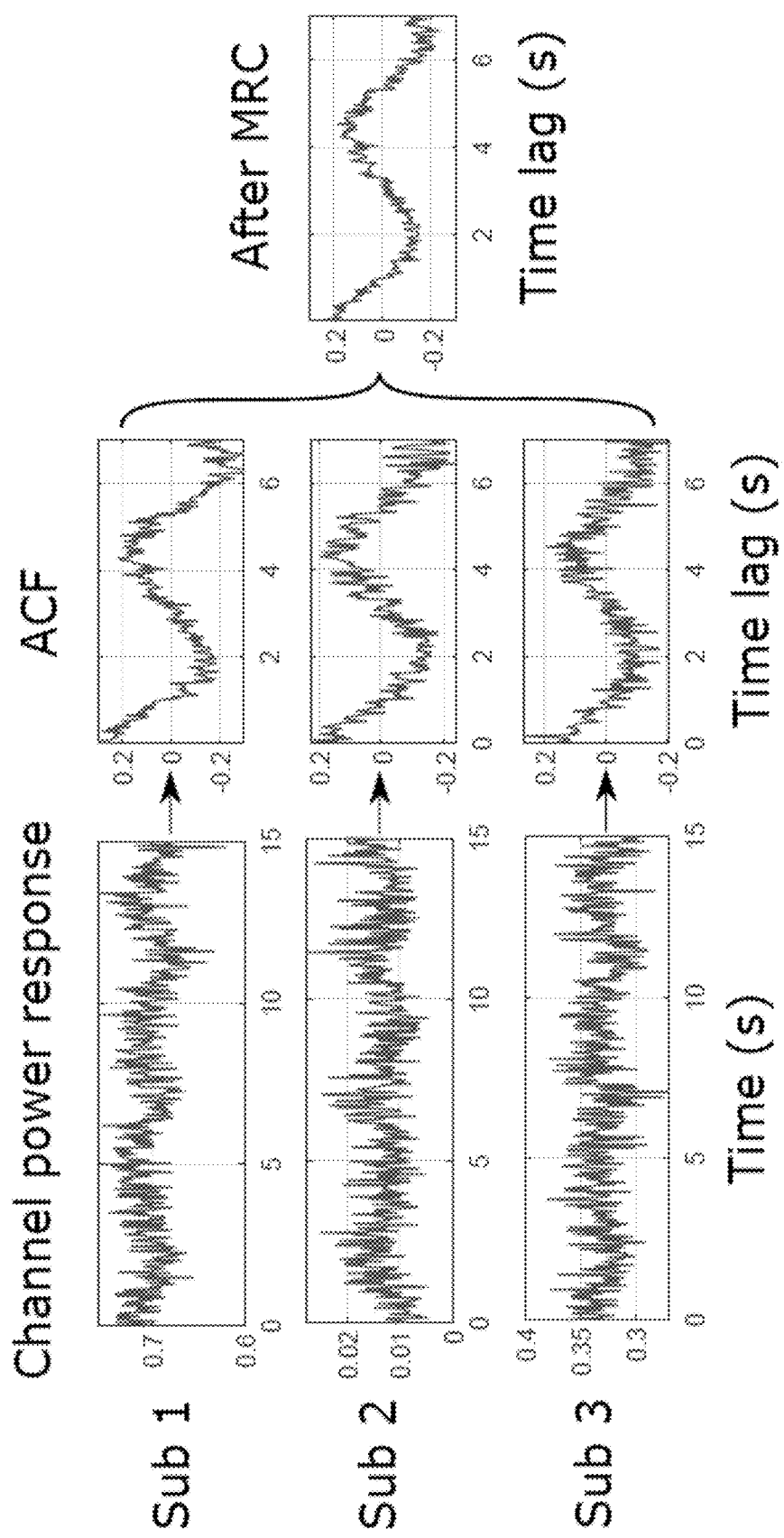
FIG. 21 illustrates an exemplary breathing signal based on real-world measurements, according to one embodiment of the present teaching.
Figure 22:
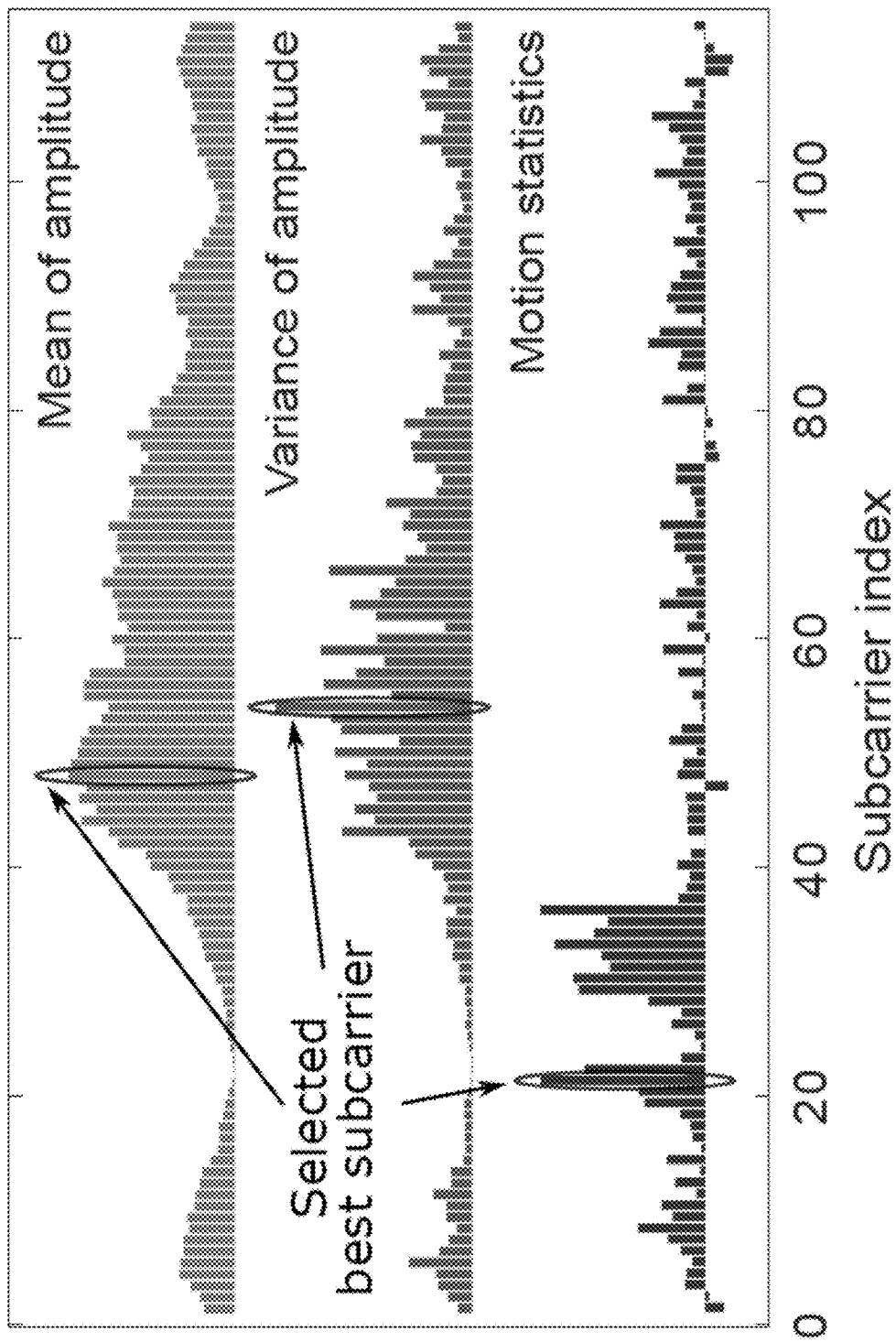
FIG. 22 demonstrates gains of a disclosed scheme for breathing signal extraction and maximization, according to one embodiment of the present teaching.

As discussed above, FIG. 18 summarizes a proposed scheme for breathing signal extraction and maximization. The left part of FIG. 18 shows the decomposition of the measured ACF of the channel power response when a person breathes normally in the monitored area, and the right part shows the MRC scheme for boosting the SNR of the ACF of the breathing signal. FIG. 21 depicts an illustrative example based on real-world measurements, where the SNR of the breathing signal is amplified by 2.5 dB compared to the best subcarrier indicated by largest variance and by 3.7 dB compared to directly averaging all subcarriers. FIG. 22 further demonstrates the gains of the disclosed ACF-based MRC scheme and confirms the observations herein that amplitudes and their variances are not effective metrics for subcarrier selection. As seen, the subcarrier that is the most sensitive to motion (i.e., holding the largest motion statistic) could experience very small amplitude and low variance.

Sleep Stage Recognition

SMARS divides the continuous motion and breathing estimates of overnight sleep into 300-second epochs. For each epoch, SMARS recognizes three different sleep stages, i.e., wake, REM sleep and NREM sleep. The staging is performed in two steps: First, SMARS differentiates wake from sleep mainly by body motions; Second, REM and NREM stages are further identified during sleep period.

Sleep/Wake Detection.

SMARS first implements a sleep-wake detector to identify the sleep and wake states. The key insight is that, more frequent body movements will be observed when a subject is awake, while mainly breathing motion presents when he/she is asleep. Since bodily movements are significantly stronger than breathing motions, and both of them can be easily captured and quantified by the motion statistic defined herein, SMARS utilizes it to distinguish between sleep and wake states.

Figure 23A:
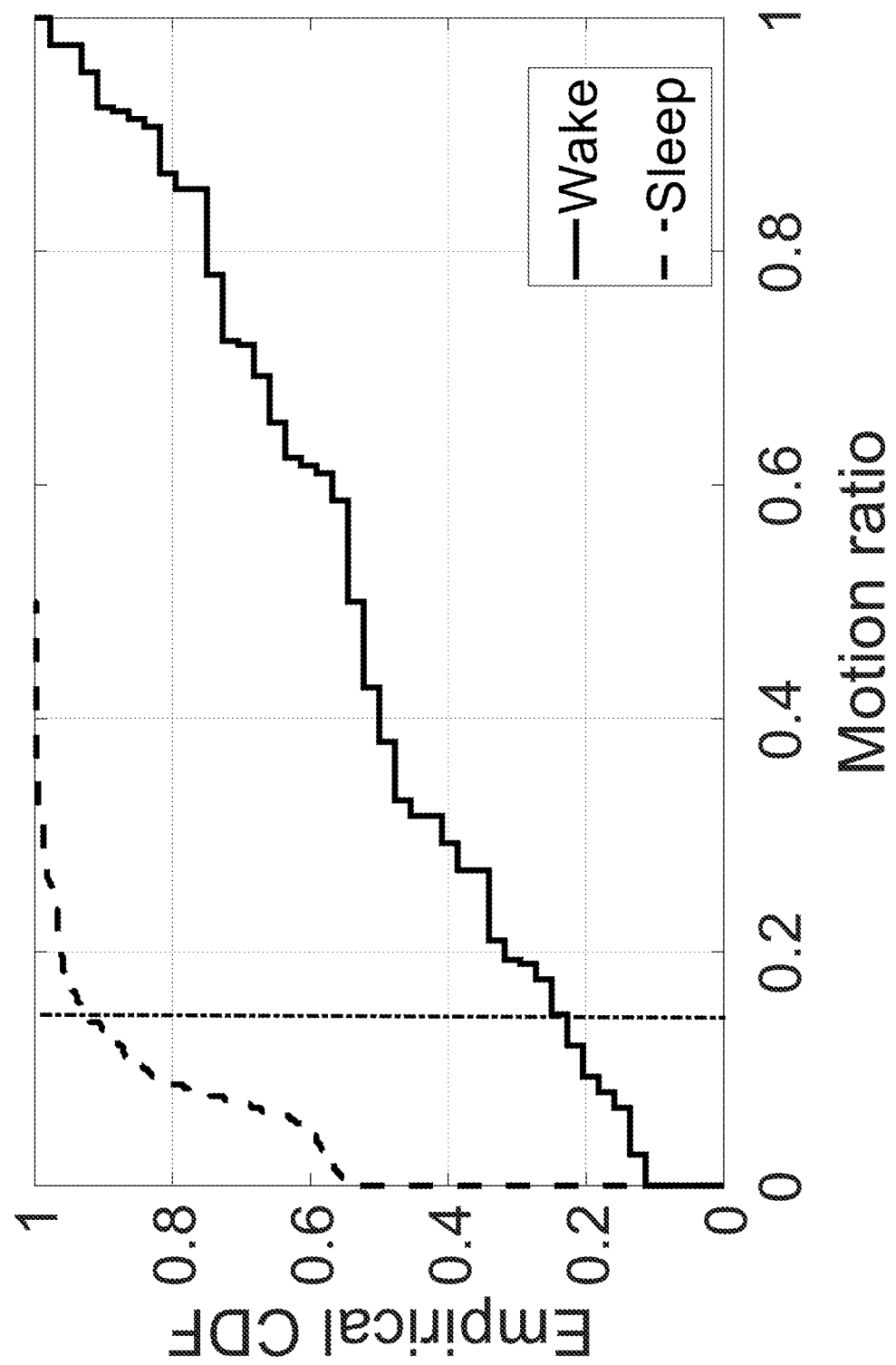
FIG. 23A and FIG. 23B illustrate comparison results between a wake state and a sleep state, according to one embodiment of the present teaching.
Figure 23B:
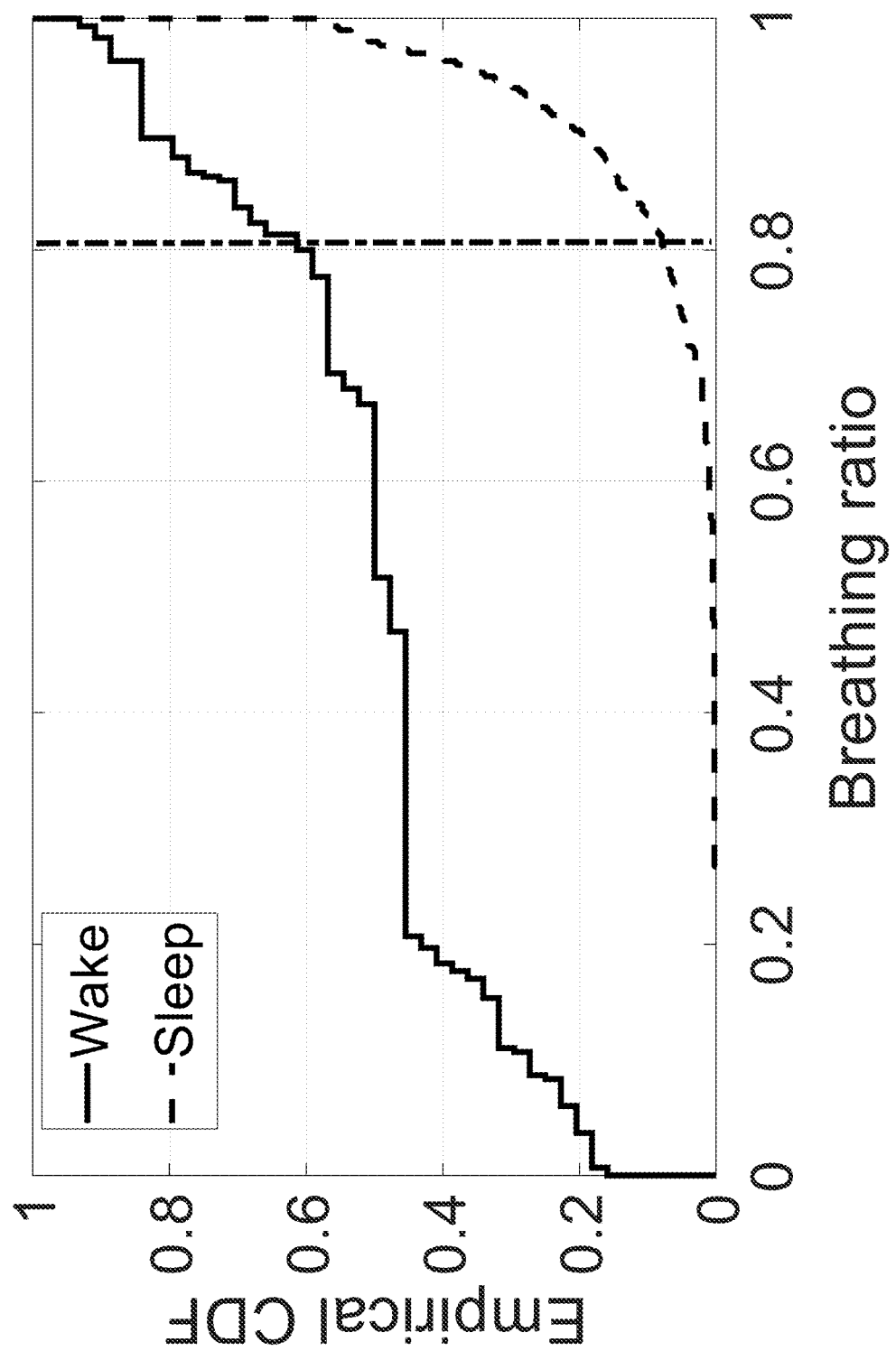

Specifically, one can define motion ratio as the percentage of time when the motion statistic, $\hat{\rho}_b(1/F_s)$, is larger than a preset threshold. Thus for the wake state, a higher motion ratio is expected, as shown in FIG. 23A. Similarly, one can also define breathing ratio as the percentage of time when the breathing signal is detected. Since bodily movements destroy the periodicity of the environmental dynamics, the breathing ratio will be lower when a subject is awake, as shown in FIG. 23B.

Combining the above two features, SMARS identifies an epoch as sleep only when the motion ratio is smaller than the predefined threshold and the breathing ratio is larger than the other threshold. Both thresholds are empirically determined as in FIG. 23A and FIG. 23B. Since the disclosed model statistically considers all multipaths indoors, the values of both thresholds generalize to different environments and subjects.

REM/NREM Recognition.

SMARS exploits the following clinical facts and accordingly extracts two distinctive features from breathing rate estimates for REM/NREM stages classification: Breathing rate is usually faster and presents higher variability and irregular patterns for REM stage, while more stable and slower for NREM stage.

Figure 24A:
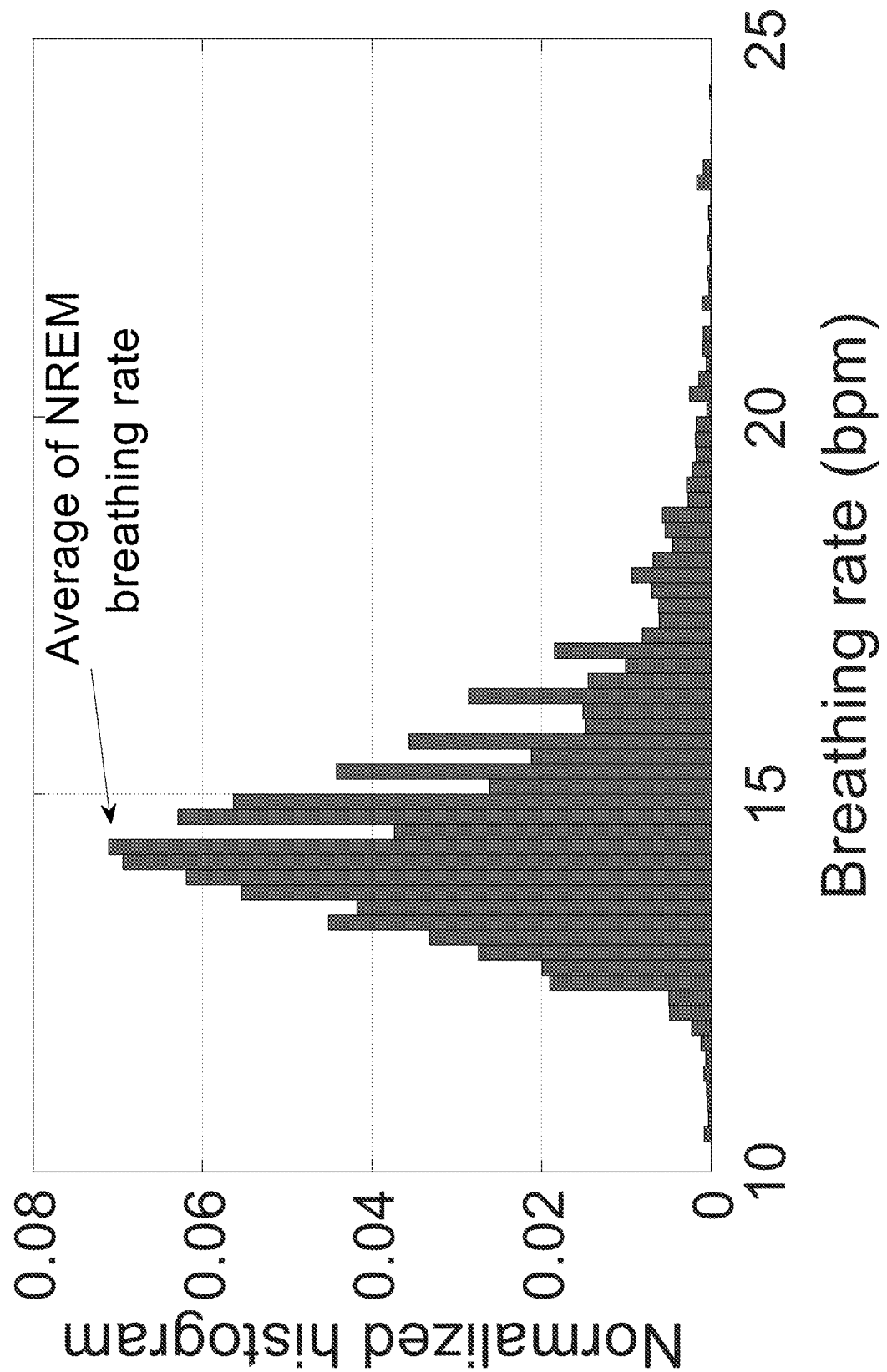
FIG. 24A and FIG. 24B illustrate breathing rate performances of different sleep stages, according to one embodiment of the present teaching.

Since NREM stage constitutes the majority (about 75% to 80%) of total sleep for typical healthy adults, the average breathing rate during NREM stage can be estimated by localizing the peak of the histogram of overnight breathing rate estimates, as shown in FIG. 24A. On this basis, one can define breathing rate deviation, the distance between the estimated average NREM breathing rate and the 90% tile of the breathing rate for each epoch, to quantify the deviation of the breathing rate during REM stage from that during NREM stage.

To extract the variability of the breathing rate for each epoch, one can first estimate the trend of breathing rate by applying a low pass filter to the breathing estimates of the whole night, and obtain the detrended breathing rate estimates by subtracting the trend from the original breathing rate estimates. Then, the breathing rate variability is defined and calculated for each epoch as the variance of the detrended estimates normalized by the length of epoch.

Figure 24B:
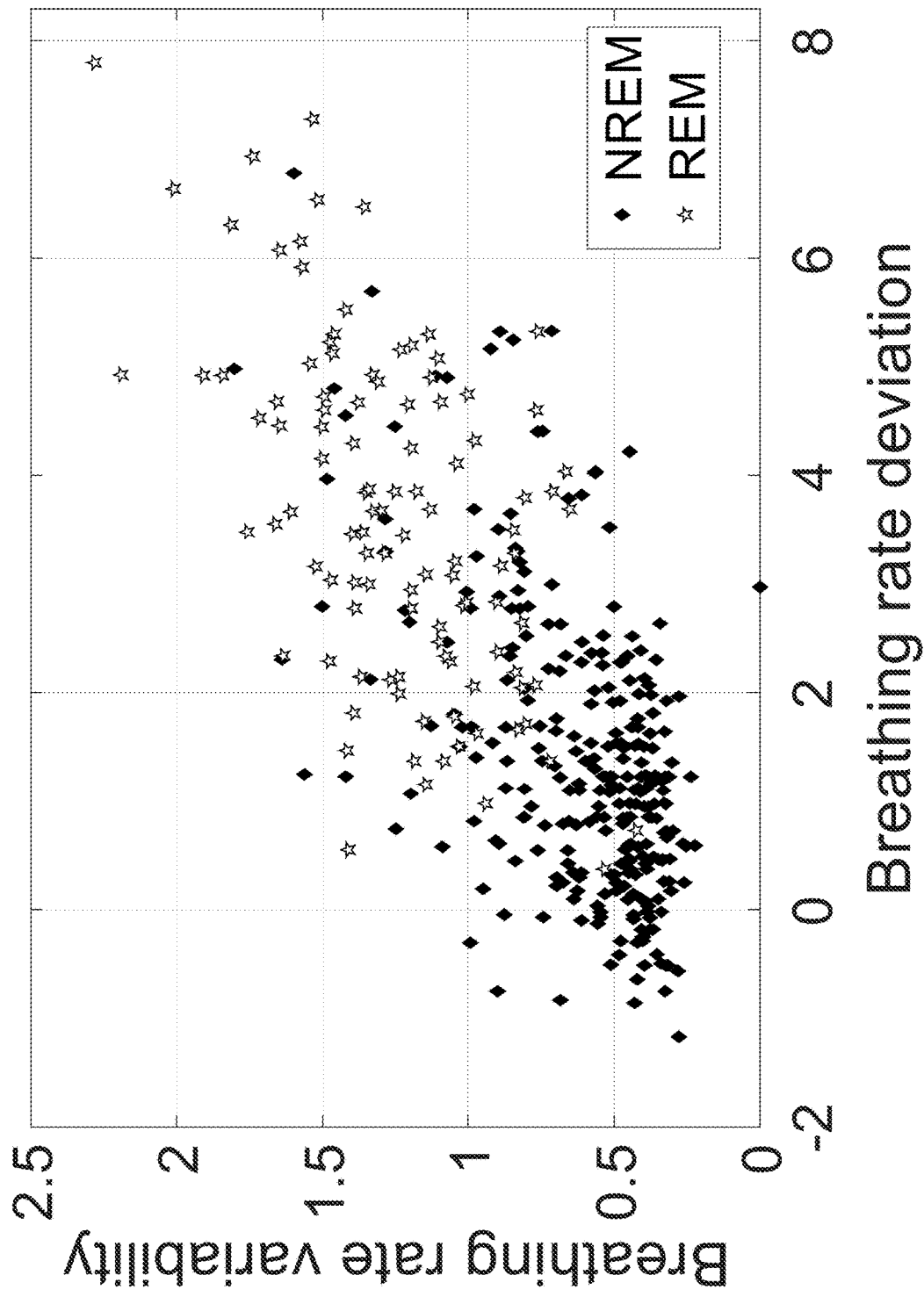

FIG. 24B visualizes the distribution of the proposed two features under NREM and REM sleep, respectively. As one can see from FIG. 24B, the majority of the breathing rate variability and breathing rate deviation of NREM sleep are much smaller than those of REM sleep. Based on these two features, one can train a support vector machine (SVM), a widely used binary classifier, to differentiate between REM and NREM sleep.

Sleep Quality Assessment

When one obtains the estimates of wake, REM, and NREM stages of a whole sleep, one can assess the elusive sleep quality for a user by following standard approach used in clinical practice. In particular, one can calculate the sleep score for each night based on the recognized sleep stages as follows. Let $T_N$, $T_R$ and $T_W$ denote the durations (measured in hours) of NREM sleep, REM sleep and wake, respectively. Since there is no standard formula for sleep score calculation, a simple formula for the sleep score is applied in SMARS:

$$S=10*T_N+20*T_R-10*T_W, \qquad (14)$$

which means that the more you sleep, the more you have REM sleep, the less you keep awake in the bed, the better your sleep score is. According to recent research, REM sleep is crucial for mental recovery, and thus a higher weight has been assigned to REM sleep.

SMARS envisions a practical sleep monitoring for daily in-home use. Although it does not make much sense to compare the sleep score among different users, the trend or history of the sleep score for a particular user would reflect the changes of his/her sleep quality. Such results provide clinically meaningful evidences to help diagnose sleep disorders and manage personal health, in an attractive way.

Figure 25:
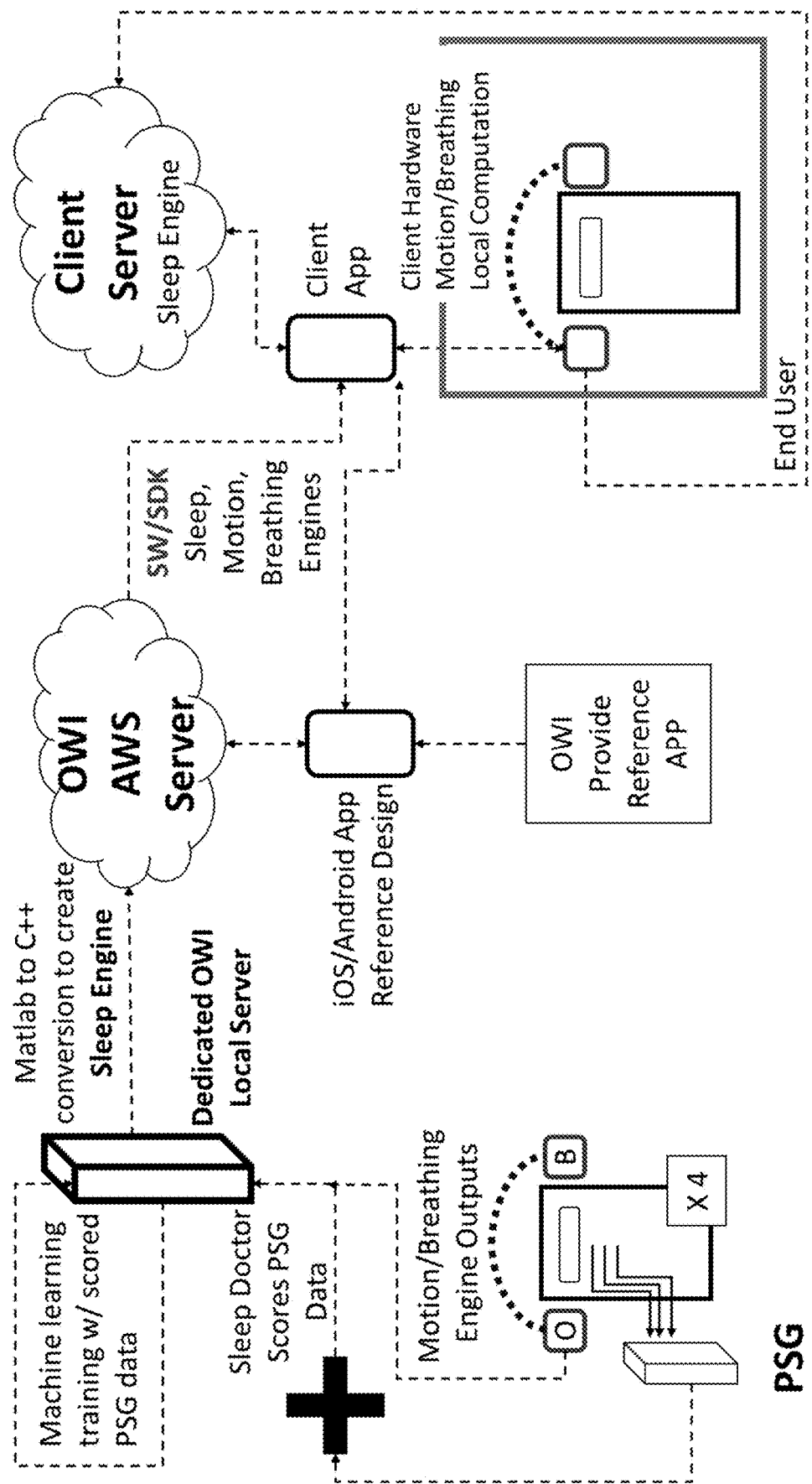
FIG. 25 illustrates an exemplary network environment for sleep monitoring, according to one embodiment of the present teaching.
Figure 26:
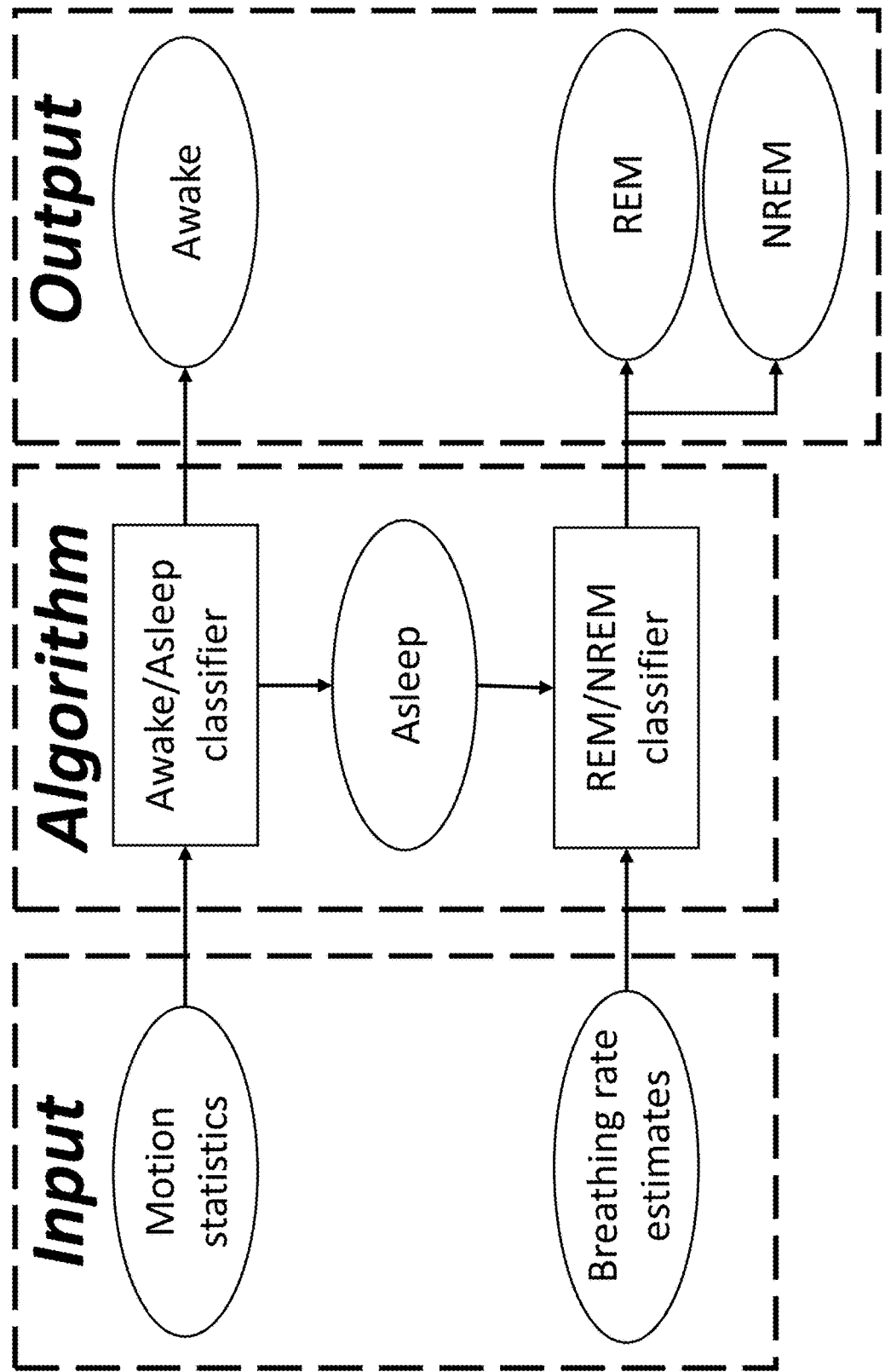
FIG. 26 illustrates an exemplary algorithm design for sleep monitoring, according to one embodiment of the present teaching.

FIG. 25 illustrates an exemplary network environment for sleep monitoring, according to one embodiment of the present teaching. FIG. 26 illustrates an exemplary algorithm design for sleep monitoring, according to one embodiment of the present teaching.

Figure 27:
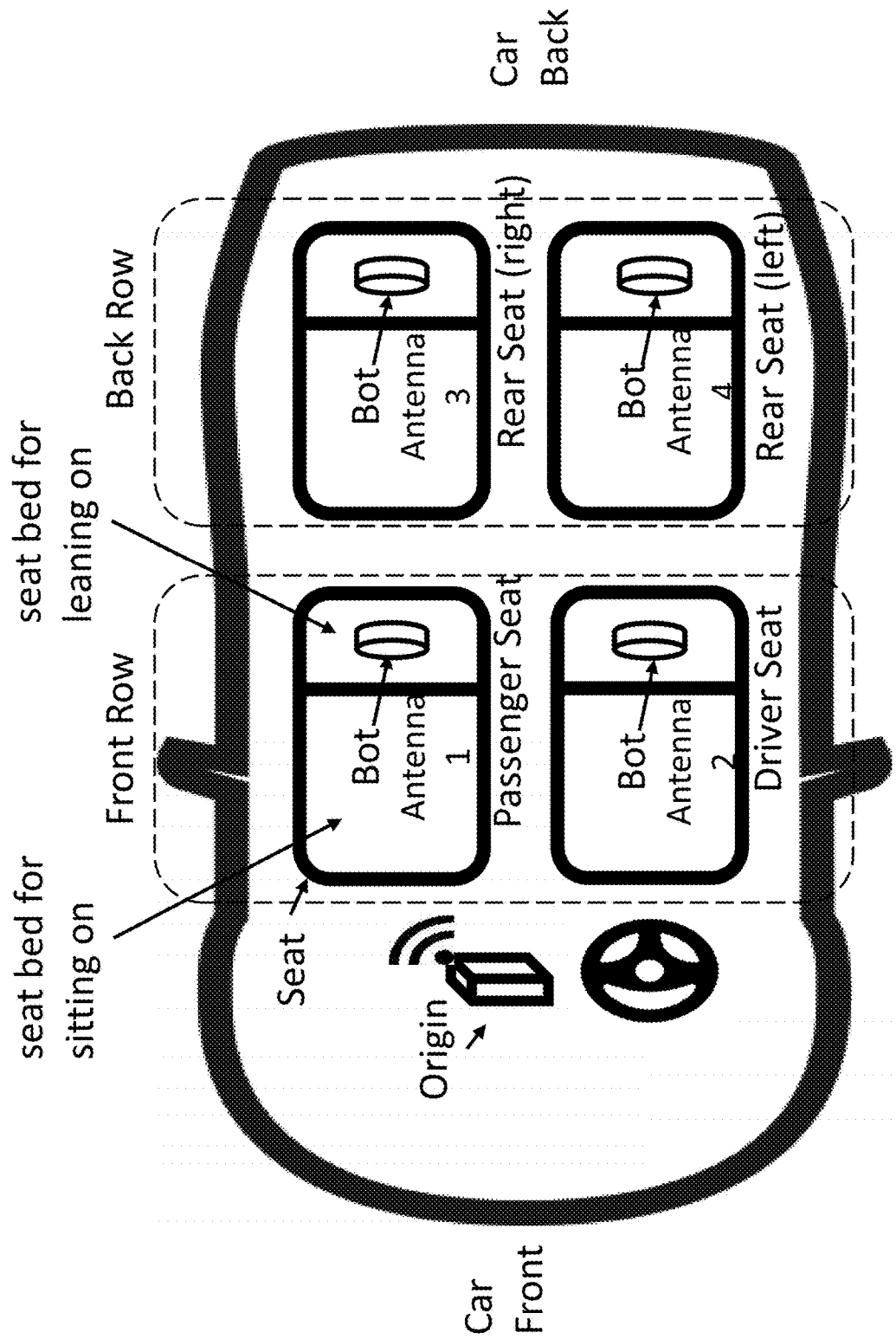
FIG. 27 illustrates an exemplary interior bird-view of a car for seat occupancy detection and people counting, according to one embodiment of the present teaching.

FIG. 27 illustrates an exemplary interior bird-view of a car for seat occupancy detection and people counting, according to one embodiment of the present teaching. In an example, one or more Type 1 devices and multiple Type 2 devices (e.g. N=4) may be placed in a confined area (e.g. closed area such as a car, a conference room, a bus, an airplane, or a cinema, semi-open area such as a bus with windows open, or a balcony with 8 outdoor chairs around an outdoor table) with multiple "seats" at fixed locations (may be a space for standing, sitting, kneeling, lying down, etc.,) that may hold a person. A presence of a person at one or more "seats" may be detected based on time series of CI extracted from wireless signals sent from the Type 1 devices to the Type 2 devices.

FIG. 27 shows a particular example of a car with 4 seats, two in front row and two in back row. Note that each seat has a "seat bed" for a person to sit on and a "seat back" for a person to lean back on. The Type 1 device may be placed in the front, on the dash board. Four Type 2 devices may be deployed, one at each of the 4 seats (e.g. in/on/under the seat bed, or in/on/under the seat bed). When a seat A (e.g. driver seat, or right seat on front row, or back row left seat, etc.) is occupied by the driver or a passenger or a baby in a car-seat, the CI (channel information) associated with the occupied seat A may behave differently (e.g. become smaller or bigger) from the CI associated with an empty seat A. Thus one can detect the seat occupancy of each seat by examining the CI. By performing such test for all the seats, one can count the amount of people in the car. If a person sits at non-standard locations (e.g. between two seats, in the center of back row, in the center of front row, or a baby in a car seat), CI associated multiple Type 2 devices can be analyzed jointly to determine if there is a person there. As signature of a baby in car-seat may be different from an adult or a children, adult/children/baby classification may be performed based on the CI.

A task may be performed based on the seat occupancy described above. For example, the task may be to arm an air-bag if a seat is occupied, but disarm the airbag if the seat is not occupied. If a small size person (e.g. a child) instead of a regular-size adult is detected, an air-bag designed for adults may not be armed. The heating/air-condition setting may be adjusted. The task may be to control windows, lighting, audio system, entertainment system (e.g. video), noise cancelling, shock-absorbing system, stabilizing size, car avoidance system, safety features, tire pressure, any other car subsystems, etc. For example, if a passenger is detected at the front right seat, the temperature at that region (front, right) may be controlled to a preset level. If the seat is empty, the temperature may be adjusted differently.

Figure 28A:
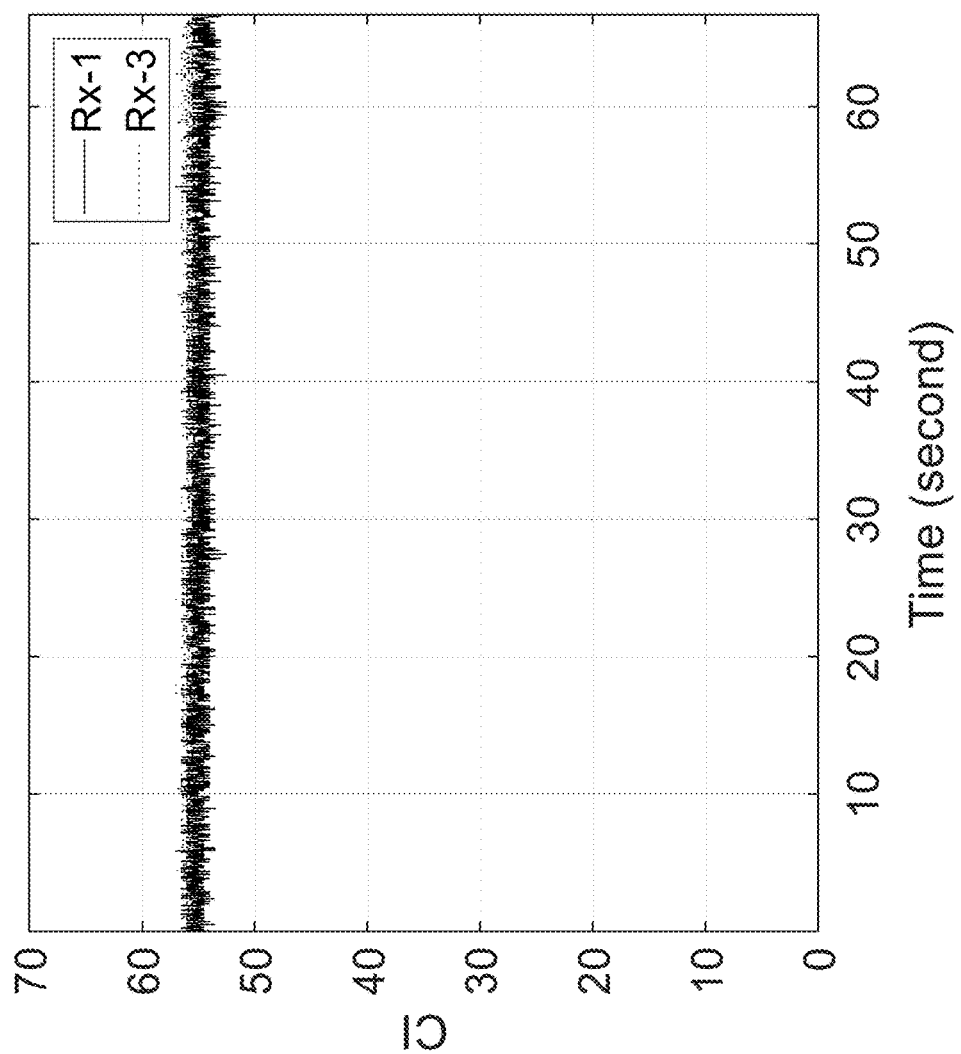
FIGS. 28A-28D illustrate changes of channel information according to various seat occupancy situations in a car, according to one embodiment of the present teaching.
Figure 28B:
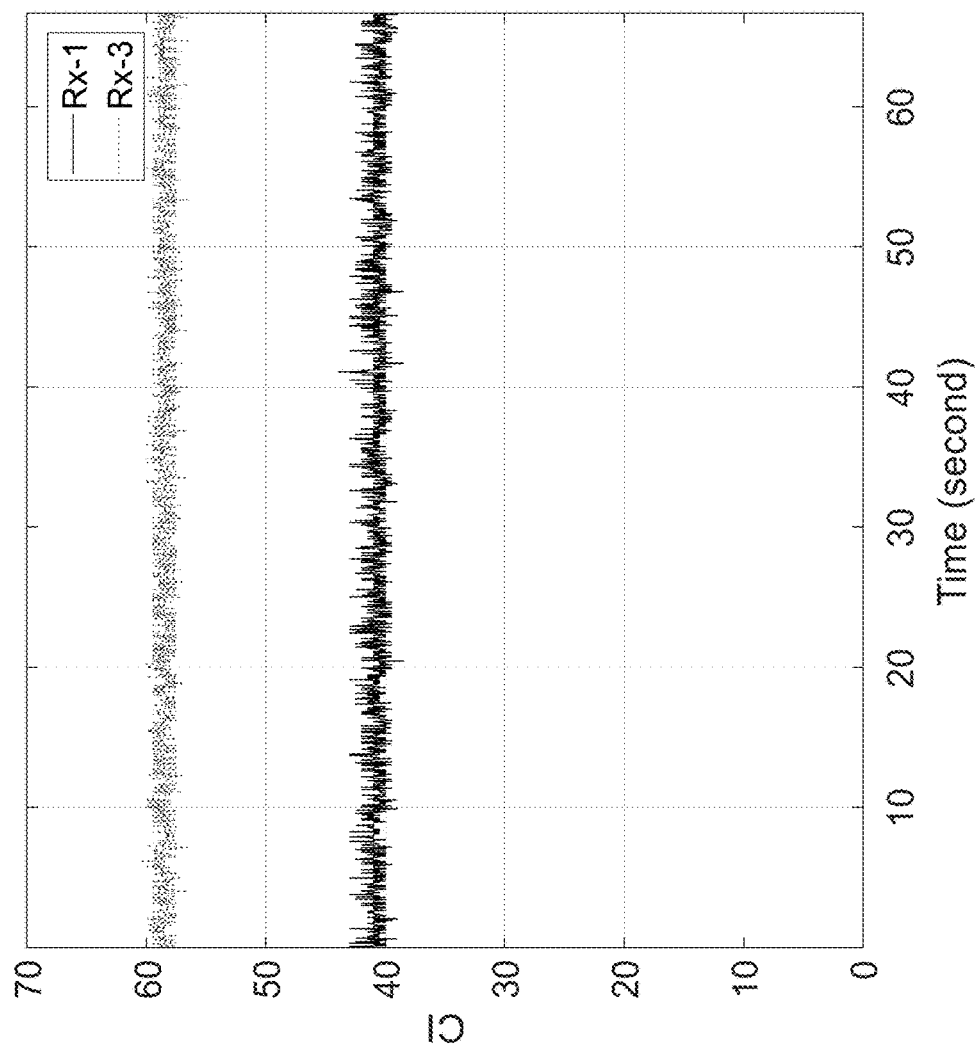
Figure 28C:
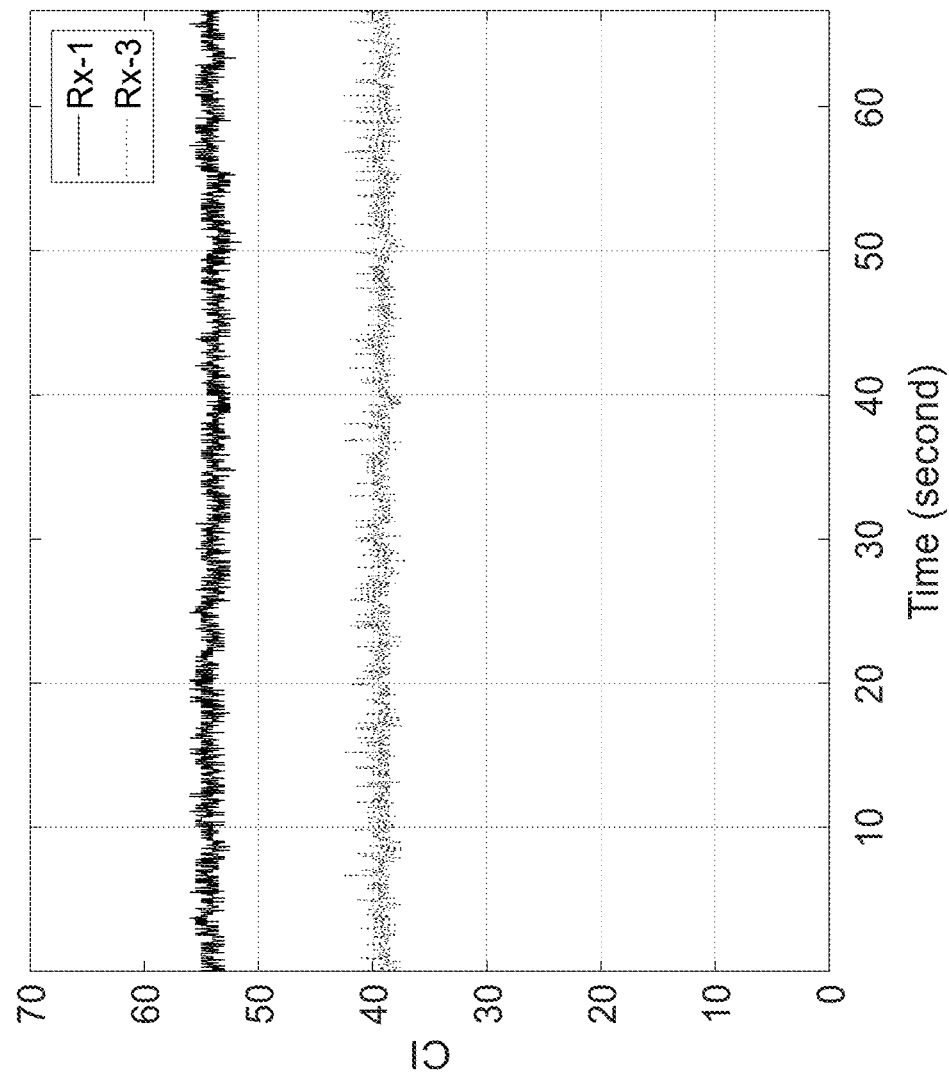
Figure 28D:
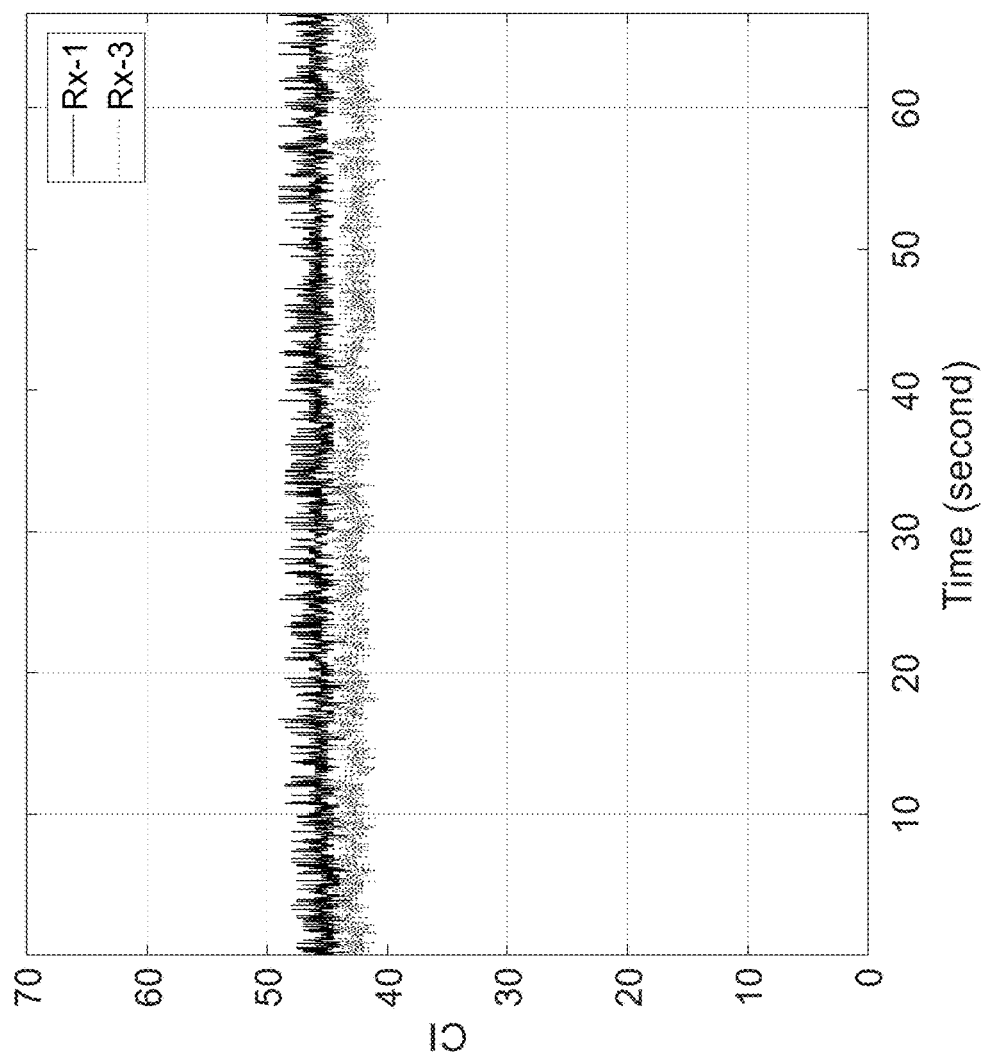

FIGS. 28A-28D illustrate changes of channel information (CI) according to various seat occupancy situations in a car, according to one embodiment of the present teaching. FIG. 28A shows CI when no seat is occupied. FIG. 28B shows CI when seat 1 (e.g. seat with Bot antenna 1 in FIG. 27) is occupied. FIG. 28C shows CI when seat 3 (e.g. seat with Bot antenna 3 in FIG. 27) is occupied. FIG. 28D shows CI when both seat 1 and seat 3 are occupied.

The features described above may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language (e.g., C, Java), including compiled or interpreted languages, and it may be deployed in any form, including as a stand-alone program or as a module, component, subroutine, a browser-based web application, or other unit suitable for use in a computing environment.

Suitable processors for the execution of a program of instructions include, e.g., both general and special purpose microprocessors, digital signal processors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, ASICs (application-specific integrated circuits).

While the present teaching contains many specific implementation details, these should not be construed as limitations on the scope of the present teaching or of what may be claimed, but rather as descriptions of features specific to particular embodiments of the present teaching. Certain features that are described in this specification in the context of separate embodiments may also be implemented in combination in a single embodiment. Conversely, various features that are described in the context of a single embodiment may also be implemented in multiple embodiments separately or in any suitable sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

Particular embodiments of the subject matter have been described. Any combination of the features and architectures described above is intended to be within the scope of the following claims. Other embodiments are also within the scope of the following claims. In some cases, the actions recited in the claims may be performed in a different order and still achieve desirable results. In addition, the processes depicted in the accompanying figures do not necessarily require the particular order shown, or sequential order, to achieve desirable results. In certain implementations, multitasking and parallel processing may be advantageous.

We claim:

1. A system for monitoring object motion in a venue, comprising:
   a transmitter located at a first position in the venue and configured for transmitting a first wireless signal through a wireless multipath channel, wherein the wireless multipath channel is impacted by a pseudo-periodic motion of an object in the venue;
   a receiver located at a second position in the venue and configured for:
      receiving a second wireless signal through the wireless multipath channel, wherein the second wireless signal is determined based on both the wireless multipath channel impacted by the pseudo-periodic motion of the object in the venue and the first wireless signal, and
      extracting at least one time series of channel information (CI) of the wireless multipath channel from the second wireless signal,
      wherein each CI comprises at least one of: a channel state information (CSI), a frequency domain CSI, a frequency domain CSI associated with at least one sub-band, a time domain CSI, a channel impulse response (CIR), a channel frequency response (CFR), a channel characteristics, and a channel filter response, of the wireless multipath channel; and
   a vital sign estimator configured for:
      determining that at least one portion of the at least one time series of CI (TSCI) in a current sliding time window is associated with the pseudo-periodic motion of the object in the venue, and
      computing a current characteristics related to the pseudo-periodic motion of the object in the current sliding time window based on at least one of: the at least one portion of the at least one TSCI in the current sliding time window, at least one portion of the at least one TSCI in a past sliding time window, and a past characteristics related to the pseudo-periodic motion of the object in the past sliding time window.

2. The system of claim 1, wherein:
   the object is at least one of: a life, a device, and a land;
   the pseudo-periodic motion represents at least one of the following of the object:
      breathing, heartbeat, periodic hand gesture, periodic gait, rotation, vibration, and earthquake; and
   the current characteristics represents a frequency of the pseudo-periodic motion.

3. The system of claim 1, wherein:
   the vital sign estimator is coupled to at least one of: the transmitter, the receiver, an additional transmitter, an additional receiver, a cloud server, a fog server, a local server, and an edge server; and at least one of the current characteristics and the past characteristics comprises information related to at least one of: a frequency of pseudo-periodic motion, a frequency characteristics, a frequency spectrum, a time period of pseudo periodic motion, a temporal characteristics, a temporal profile, a timing of pseudo-periodic motion; a starting time, an ending time, a duration, a history of motion, a motion type, a motion classification, a location of the object, a speed; a displacement, an acceleration, a rotational speed, a rotational characteristics, a gait cycle of the object, a transient behavior of the object, a transient motion, a change in pseudo-periodic motion, a change in frequency of pseudo-periodic motion, a change in gait cycle, an event associated with pseudo-periodic motion, an event associated with transient motion, a sudden-motion event, and a all-down event.

4. The system of claim 1; wherein the vital sign estimator comprises:
   a channel information processor, a spectral analyzer, and an energy spectrum normalizer that are configured for processing the at least one TSCI in the current sliding time window on both time domain and frequency domain; and
   a peak detector configured for detecting at least one peak in the frequency domain,
   wherein the current characteristics related to the pseudo-periodic motion of the object is computed based on the at least one peak in the frequency domain.

5. The system of claim 1, wherein the vital sign estimator comprises a channel information processor configured for, for each CI of a particular portion of the at least one TSCI in the current sliding time window:
   obtaining N1 frequency domain components of the CI;
   determining a timestamp associated with the CI; and
   preprocessing the N1 frequency domain components, wherein the preprocessing comprises:
      cleaning phases of the N1 frequency domain components, and
      normalizing the N1 frequency domain components such that the N1 frequency domain components have a unity total power,
   wherein the current characteristics related to the pseudo-periodic motion of the object is computed based on the preprocessed N1 frequency domain components of the CI of the particular portion of the at least one TSCI in the current sliding time window.

6. The system of claim 1, wherein the vital sign estimator comprises a spectral analyzer configured for:
   for each CI of a particular portion of the at least one TSCI in the current sliding time window:
      converting N1 frequency domain components of the channel information using an inverse frequency transform to N2 time domain coefficients of the channel information, wherein: each channel information is associated with a timestamp, N2 is not smaller than N1, each of the N2 coefficients is associated with a time delay, and the inverse frequency transform comprises at least one of: inverse Fourier transform, inverse Laplace transform, inverse Hadamard transform, inverse Hilbert transform, inverse sine transform, inverse cosine transform, inverse triangular transform, inverse wavelet transform, inverse integer transform, inverse power-of-2 transform, combined zero padding and transform, and inverse Fourier transform with zero padding, and
      retaining first C of the N2 time domain coefficients, wherein C is not larger than N2; and
   correcting timestamps of all channel information of the particular portion of the at least one TSCI in the current sliding time window so that the corrected timestamps of time-corrected channel information are uniformly spaced in time, wherein correcting the timestamps comprises:
      identifying a particular CI with a particular timestamp to be replaced by a time-corrected CI with a corrected timestamp, and
      computing the time-corrected CI by computing the C retained time domain coefficients of the time-corrected CI at the corrected timestamp using an interpolation filter associated with the corrected timestamp,
   wherein the current characteristics related to the pseudo-periodic motion of the object is computed based on the C retained time domain coefficients of the CI of the particular portion of the at least one TSCI in the current sliding time window.

7. The system of claim 6, wherein the spectral analyzer is further configured for:
   for each of the C retained time domain coefficients:
      identifying a corresponding retained time domain coefficient of each CI of the particular portion of the at least one TSCI in the current sliding time window,
      applying bandpass filtering to all the corresponding identified retained time domain coefficients, and
      applying a frequency transform to all the corresponding identified retained time domain coefficients, wherein a length of the frequency transform is not smaller than a length of the portion,
   wherein the current characteristics related to the pseudo-periodic motion of the object is computed based on outputs of the frequency transform applied to each corresponding retained time domain coefficient of the CI of the particular portion of the at least one TSCI in the current sliding time window.

8. The system of claim 7, wherein the vital sign estimator further comprises an energy spectrum normalizer, and wherein the spectral analyzer and the energy spectrum normalizer are configured for:
   processing the outputs of the frequency transform applied to each corresponding retained time domain coefficient of the CI of the particular portion of the at least one TSCI in the current sliding time window,
   wherein the frequency transform comprises at least one of: Fourier transform, Laplace transform, Hadamard transform, Hilbert transform, sine transform, cosine transform, triangular transform, wavelet transform, integer transform, power-of-2 transform, combined zero padding and transform, and Fourier transform with zero padding,
   wherein the processing comprises at least one of: preprocessing, processing, post-processing, filtering, linear filtering, nonlinear filtering, folding, grouping, energy computation, low-pass filtering, bandpass filtering, high-pass filtering, matched filtering, enhancement, restoration, de-noising, spectral analysis, inverse linear transform, nonlinear transform, feature extraction, machine learning, recognition, labeling, training, clustering, grouping, sorting, thresholding, comparison with time-corrected channel information of another portion of another time series of channel information in another sliding time window, similarity score computation, vector quantization, compression, encryption, coding, storing, transmitting, representing, merging, combining, splitting; restricting to selected frequency band, spectrum folding, averaging, averaging over selected frequency, averaging over selected time domain coefficients, and averaging over antenna links.

9. The system of claim 8, wherein:
the transmitter has at least one antenna;
the receiver has at least one antenna;
each of the at least one TSCI is associated with one of the at least one antenna of the transmitter and one of the at least one antenna of the receiver;
the averaging over antenna links is weighted averaging over the at least one TSCI; and
the averaging over selected time domain coefficients is weighted averaging over the C retained time domain coefficients.

10. The system of claim 9, wherein the vital sign estimator further comprises a peak detector configured for:
identifying at least one local maximum and at least one local minimum the frequency domain;
computing at least one local signal-to-noise-ratio-like (SNR-like) parameter for each pair of a local maximum and a local minimum adjacent to each other;
identifying significant local peaks each being at least one of: a local maximum with SNR-like parameter greater than a first threshold T1 and a local maximum with an amplitude greater than a threshold T2.

11. The system of claim 10, wherein:
the at least one local maximum and the at least one local minimum are identified in the frequency domain using a peak detection approach.

12. The system of claim 10, wherein the vital sign estimator further comprises a breathing rate estimator configured for:
selecting a set of selected significant local peaks from the set of identified significant local peaks based on a selection criterion,
wherein the current characteristics related to the pseudo-periodic motion of the object is computed based on the set of selected significant local peaks and frequency values associated with the set of selected significant local peaks.

13. The system of claim 12, wherein the breathing rate estimator is further configured for:
computing information associated with a remaining spectrum with the set of selected significant local peaks removed; and
detecting an event associated with the current characteristics related to the pseudo-periodic motion of the object based on at least one of: a remaining spectral energy of the remaining spectrum, an adaptive threshold, and a finite state machine, where the event comprises at least one of: a presence, an absence, an appearance, a disappearance, a steady behavior and a non-steady behavior of at least one of: non-periodic motion, transient motion, strong motion, weak motion; strong background interference and another periodic motion.

14. The system of claim 13, further comprising a system state controller configured for:
computing adaptively at least one of: decision thresholds, threshold T1, threshold T2, lower bound associated with frequency of the selected significant local peaks, upper bound associated with frequency of the selected significant local peaks, search range, and a parameter associated with a selection of the selected significant local peaks, based on a finite state machine (FSM), wherein the FSM comprises at least one of: an Initiation (DIT) state, a Verification state, a PeakFound state, and a Motion state.

15. The system of claim 14, wherein the system state controller is further configured for:
entering the INIT state of the FSM in at least one predetermined way;
computing the thresholds adaptively in a first way in the INIT state;
detecting an event based on the thresholds;
transitioning from the INIT state to a different state of the FSM based on at least one transition criterion; and
computing the thresholds adaptively in a second way in the different state.

16. The system of claim 14, wherein the system state controller is further configured for:
entering the INIT state of the FSM;
computing the thresholds adaptively in a first way;
detecting an event based on the thresholds and at least one of: the set of selected significant local peaks and related characteristics;
detecting excessive background interfering motion based on the thresholds and the remaining spectral energy;
staying in the INIT state when the event is concluded to be "not detected" and the excessive background interfering motion is concluded to be "not detected;"
transitioning from the INIT state to the Verification state when the event is concluded to be "detected" preliminarily and the detected event needs to be verified; and
transitioning from the INIT state to the Motion state when the excessive background interfering motion is concluded to be "detected."

17. The system of claim 16, wherein the system state controller is further configured for:
in the Verification state:
computing the thresholds adaptively in a second way;
accumulating and computing at least one statistics based on sets of selected significant local peaks and related characteristics in at least one adjacent sliding time window for verification of the detected event that is detected preliminarily;
staying in the Verification state while the at least one statistics is being accumulated until sufficient statistics is collected for the verification;
verifying the preliminarily detected event based on the thresholds and the at least one statistics;
transitioning from the Verification state to the PeakFound state when the preliminarily detected event is concluded as "verified;"
transitioning from the Verification state to the INIT state when verification is concluded to be "not verified;" and
staying in the Verification state when verification is not concluded.

18. The system of claim 17, wherein the system state controller is further configured for:
in the PeakFound state:
computing the thresholds adaptively in a third way;
detecting the verified event based on the thresholds and the at least one of: the set of selected significant local peaks and related characteristics;
detecting the excessive background interfering motion based on the thresholds and the remaining spectral energy;
staying in the PeakFound state when the verified event is concluded as "detected;"

transitioning from the PeakFound state to the INIT state when the verified event is concluded as "not detected" for a number of time instances; and transitioning from the PeakFound state to the Motion state when the excessive background interfering motion is concluded as "detected" for a number of time instances.

19. The system of claim 16, wherein the system state controller is further configured for:

in the Motion state:

computing the thresholds adaptively in a fourth way;

detecting the excessive background interfering motion based on the thresholds and the remaining spectral energy;

staying in the Motion state when the excessive background interfering motion is concluded as "detected;" and transitioning from the Motion state to the INIT state when the excessive background interfering motion is concluded as "not detected" for a number of time instances.

20. The system of claim 1, wherein the vital sign estimator further comprises a spectral analyzer configured for:

determining a timestamp associated with each channel information of the at least one TSCI;

correcting timestamps of all channel information of a particular portion of the at least one TSCI in the current sliding time window so that the corrected timestamps of time-corrected channel information are uniformly spaced in time; and performing an operation on the time-corrected channel information with respect to the corrected timestamps, wherein the current characteristics related to the pseudo-periodic motion of the object is computed based on an output of the operation, wherein the operation comprises at least one of: preprocessing, processing, post-processing, filtering, linear filtering, nonlinear filtering, low-pass filtering, band-pass filtering, high-pass filtering, matched filtering, enhancement; restoration, de-noising, spectral analysis, frequency transform, inverse frequency transform, linear transform, nonlinear transform, feature extraction, machine learning, recognition, labeling, training, clustering, grouping, sorting, thresholding, peak detection, comparison with time-corrected channel information of another portion of another time series of channel information in another sliding time window, similarity score computation, vector quantization, compression, encryption, coding, storing, transmitting, representing, merging, combining, fusion, linear combination, non-linear combination, and splitting.

21. The system of claim 1, wherein the vital sign estimator is further configured for:

making the current characteristics related to the pseudo-periodic motion of the object available in real time; and moving the current sliding time window by a shift-size as time progresses.

22. The system of claim 1, further comprising:

an additional transmitter located at a third position in the venue and configured for transmitting a third wireless signal through the wireless multipath channel impacted by the pseudo-periodic motion of the object in the venue;

an additional receiver located at a fourth position in the venue and configured for:

receiving a fourth wireless signal through the wireless multipath channel, wherein the fourth wireless signal is determined based on both the wireless multipath channel and the third wireless signal, and obtaining an additional TSCI of the wireless multipath channel based on the fourth wireless signal, wherein the vital sign estimator is further configured for:

determining that at least one portion of the additional TSCI in the current sliding time window is associated with the pseudo-periodic motion of the object in the venue, and computing the current characteristics related to the pseudo-periodic motion of the object in the current sliding time window based on at least one of: the at least one portion of the additional TSCI in the current sliding time window, at least one portion of the additional TSCI in an additional past sliding time window, and a past characteristics related to the pseudo-periodic motion of the object in the additional past sliding time window.

23. The system of claim 1, wherein the vital sign estimator is further configured for:

determining that at least one portion of the at least one TSCI in the current sliding time window is associated with an additional pseudo-periodic motion of an additional object in the venue, wherein the wireless multipath channel is further impacted in the current sliding time window by the additional pseudo-periodic motion of the additional object; and computing a current characteristics related to the additional pseudo-periodic motion of the additional object in the current sliding time window based on at least one of: the at least one portion of the at least one TSCI in the current sliding time window, the at least one portion of the at least one TSCI in the past sliding time window, and a past characteristics related to the additional pseudo-periodic motion of the additional object in the past sliding time window.

24. The system of claim 23, wherein the vital sign estimator is further configured for:

determining that the wireless multipath channel is impacted in the current sliding time window by pseudo-periodic motions of a plurality of objects;

computing current characteristics related to pseudo-periodic motions of the plurality of objects in the current sliding time window based on at least one of: the at least one portion of the at least one TSCI in the current sliding time window, the at least one portion of the at least one TSCI in the past sliding time window, and a past characteristics related to the pseudo-periodic motions of the plurality of objects in the past sliding time window; and estimating a quantity of the plurality of objects based on the current characteristics.

25. A method for monitoring object motion in a venue, comprising:

receiving a wireless signal as an output of a wireless multipath channel, wherein the wireless multipath channel is impacted by a pseudo-periodic motion of an object in the venue;

extracting at least one time series of channel information (CI) of the wireless multipath channel from the wireless signal, wherein each CI comprises at least one of: a channel state information (CSI), a frequency domain CSI, a frequency domain CSI associated with at least one sub-band, a time domain CSI, a channel impulse response (CIR), a channel frequency response (CFR), a channel characteristics, and a channel filter response, of the wireless multipath channel;

determining that at least one portion of the at least one time series of CI (TSCI) in a current sliding time window is associated with the pseudo-periodic motion of the object in the venue; and computing a current characteristics related to the pseudo-periodic motion of the object in the current sliding time window based on at least one of: the at least one portion of the at least one TSCI in the current sliding time window, at least one portion of the at least one TSCI in a past sliding time window, and a past characteristics related to the pseudo-periodic motion of the object in the past sliding time window.

26. The method of claim 25, further comprising:

processing the at least one TSCI in the current sliding time window on both time domain and frequency domain; and detecting at least one peak in the frequency domain, wherein the current characteristics related to the pseudo-periodic motion of the object is computed based on the at least one peak in the frequency domain, wherein at least one of the current characteristics and the past characteristics comprises information related to at least one of: a frequency of pseudo-periodic motion, a frequency characteristics, a frequency spectrum, a time period of pseudo periodic motion, a temporal characteristics, a temporal profile, a timing of pseudo-periodic motion, a starting time, an ending time, a duration, a history of motion, a motion type, a motion classification, a location of the object, a speed, a displacement, an acceleration, a rotational speed, a rotational characteristics, a gait cycle of the object, a transient behavior of the object, a transient motion, a change in pseudo-periodic motion, a change in frequency of pseudo-periodic motion, a change in gait cycle, an event associated with pseudo-periodic motion, an event associated with transient motion, a sudden-motion event, and a fall-down event.

27. The method of claim 25, further comprising:

determining a timestamp associated with each channel information of the at least one TSCI;

correcting timestamps of all channel information of a particular portion of the at least one TSCI in the current sliding time window so that the corrected timestamps of time-corrected channel information are uniformly spaced in time; and performing an operation on the time-corrected channel information with respect to the corrected timestamps, wherein the current characteristics related to the pseudo-periodic motion of the object is computed based on an output of the operation, wherein the operation comprises at least one of: preprocessing, processing, post-processing, filtering, linear filtering, nonlinear filtering, low-pass filtering, band-pass filtering, high-pass filtering, matched filtering, enhancement, restoration, de-noising, spectral analysis, frequency transform, inverse frequency transform, linear transform, nonlinear transform, feature extraction, machine learning, recognition, labeling, training, clustering, grouping, sorting, thresholding, peak detection, comparison with time-corrected channel information of another portion of another time series of channel information in another sliding time window, similarity score computation, vector quantization, compression, encryption, coding, storing, transmitting, representing, merging, combining, fusion, linear combination, nonlinear combination, and splitting.

28. A receiver of a motion monitoring system, comprising:

a wireless circuitry configured to receive a wireless signal as an output of a wireless multipath channel, wherein the wireless multipath channel is impacted by a pseudo-periodic motion of an object in a venue, wherein an input signal of the wireless multipath channel is transmitted asynchronously by a transmitter of the motion monitoring system, wherein the transmitter is different from the receiver and different from the object;

a processor communicatively coupled with the wireless circuitry;

a memory communicatively coupled with the processor; and a set of instructions stored in the memory which, when executed, causes the processor to extract at least one time series of channel information (CO of the wireless multi path channel from the wireless signal, wherein:

at least one portion of the at least one time series of CI (TSCI) in a current sliding time window is associated with the pseudo-periodic motion of the object in the venue, and the at least one portion of the at least one TSCI in the current sliding time window is to be used by a vital sign estimator of the motion monitoring system to compute a current characteristics related to the pseudo-periodic motion of the object in the current sliding time window based on at least one of: the at least one portion of the at least one TSCI in the current sliding time window, at least one portion of the at least one TSCI in a past sliding time window, and a past characteristics related to the pseudo-periodic motion of the object in the past sliding time window.

29. The receiver of claim 28, wherein the vital sign estimator is coupled to the receiver and configured for:

processing the at least one TSCI in the current sliding time window on both time domain and frequency domain; and detecting at least one peak in the frequency domain, wherein the current characteristics related to the pseudo-periodic motion of the object is computed based on the at least one peak in the frequency domain, wherein at least one of the current characteristics and the past characteristics comprises information related to at least one of: a frequency of pseudo-periodic motion, a frequency characteristics, a frequency spectrum, a time period of pseudo periodic motion, a temporal characteristics, a temporal profile, a timing of pseudo-periodic motion, a starting time, an ending time, a duration, a history of motion, a motion type, a motion classification, a location of the object, a speed, a displacement, an acceleration, a rotational speed, a rotational characteristics, a gait cycle of the object, a transient behavior of the object, a transient motion, a change in pseudo-periodic motion, a change in frequency of pseudo-periodic motion, a change in gait cycle, an event associated with pseudo-periodic motion, an event associated with transient motion, a sudden-motion event, and a fall-down event.

30. An estimator of a motion monitoring system, comprising:

a processor;

a memory communicatively coupled with the processor; and a set of instructions stored in the memory which, when executed, causes the processor to perform:

obtaining at least one time series of channel information (TSCI) of a wireless multipath channel extracted by a receiver of the motion monitoring system from a wireless signal received as an output of the wireless multipath channel, wherein the wireless multipath channel is impacted by a pseudo-periodic motion of an object in a venue, and wherein an input signal of the wireless multipath channel is transmitted by a transmitter of the motion monitoring system, wherein the transmitter is different from the receiver and different from the object, determining that at least one portion of the at least one TSCI in a current sliding time window is associated with the pseudo-periodic motion of the object in the venue, and computing a current characteristics related to the pseudo-periodic motion of the object in the current sliding time window based on at least one of: the at least one portion of the at least one TSCI in the current sliding time window, at least one portion of the at least one TSCI in a past sliding time window, and a past characteristics related to the pseudo-periodic motion of the object in the past sliding time window.

\* \* \* \* \*